US007004174B2

(12) United States Patent
Eggers et al.

(10) Patent No.: US 7,004,174 B2
(45) Date of Patent: Feb. 28, 2006

(54) ELECTROSURGERY WITH INFILTRATION ANESTHESIA

(75) Inventors: Philip E. Eggers, Dublin, OH (US); Michael W. Jopling, Columbus, OH (US)

(73) Assignee: Neothermia Corporation, Natick, MA (US)

( * ) Notice: Subject to any disclaimer, the term of this patent is extended or adjusted under 35 U.S.C. 154(b) by 369 days.

(21) Appl. No.: 10/243,028

(22) Filed: Sep. 13, 2002

(65) Prior Publication Data

US 2003/0225401 A1 Dec. 4, 2003

Related U.S. Application Data

(60) Provisional application No. 60/385,236, filed on May 31, 2002.

(51) Int. Cl.
*A61B 19/00* (2006.01)
(52) U.S. Cl. .................. 128/898; 600/565; 600/564; 606/45
(58) Field of Classification Search ............. 606/41, 606/45–47, 49–52; 600/564–568
See application file for complete search history.

(56) References Cited

U.S. PATENT DOCUMENTS 6,261,241 B1    7/2001  Burbank et al.
6,277,083 B1    8/2001  Eggers et al.
6,331,166 B1   12/2001  Burbank et al.
6,471,659 B1   10/2002  Eggers et al.
6,565,561 B1 *  5/2003  Goble et al. ................. 606/41

OTHER PUBLICATIONS

J. A. Pearce, PHD, *Electrosurgery*, John Wiley & Sons, New York, pp 68-77 (1986).
*0.4% and 0.8% Lidocaine Hydrochloride and 5% Dextrose Injection, USP*, Abbott Laboratories, North Chicago, IL, publication 58-6335-R12-Rev Dec. 2000.
J. E. Tetzlaff, *Clinical Pharmacology of Local Anesthetics*, Butterworth Heinemann, Woburn, MA, pp 15-23, 85-95.

* cited by examiner

*Primary Examiner*—Rosiland Rollins
(74) *Attorney, Agent, or Firm*—Mueller and Smith, LPA

(57) ABSTRACT

Method for carrying out the recovery of an intact volume of tissue wherein a delivery cannula tip is positioned in confronting adjacency with the volume of tissue to be recovered. The electrosurgical generator employed to form an arc at a capture component extending from the tip is configured having a resistance-power profile which permits recovery of the specimen without excessive thermal artifact while providing sufficient power to sustain a cutting arc. For the recovery procedure, a local anesthetic employing a diluent which exhibits a higher resistivity is utilized and the method for deploying the capture component involves an intermittent formation of a cutting arc with capture component actuation interspersed with pauses of duration effective to evacuate any accumulation or pockets of local anesthetic solution encountered by the cutting electrodes.

31 Claims, 26 Drawing Sheets

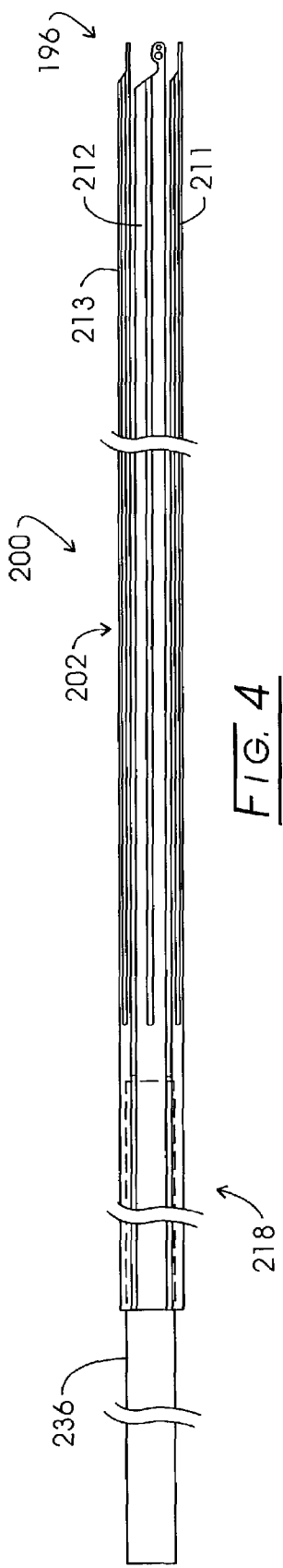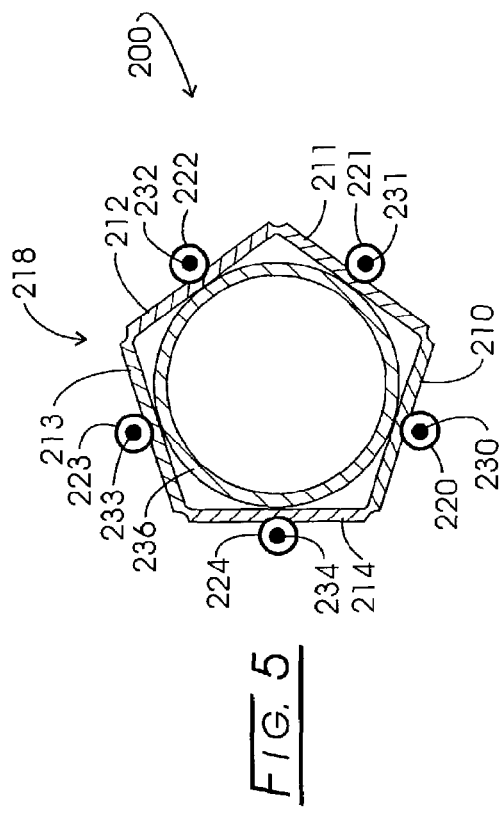

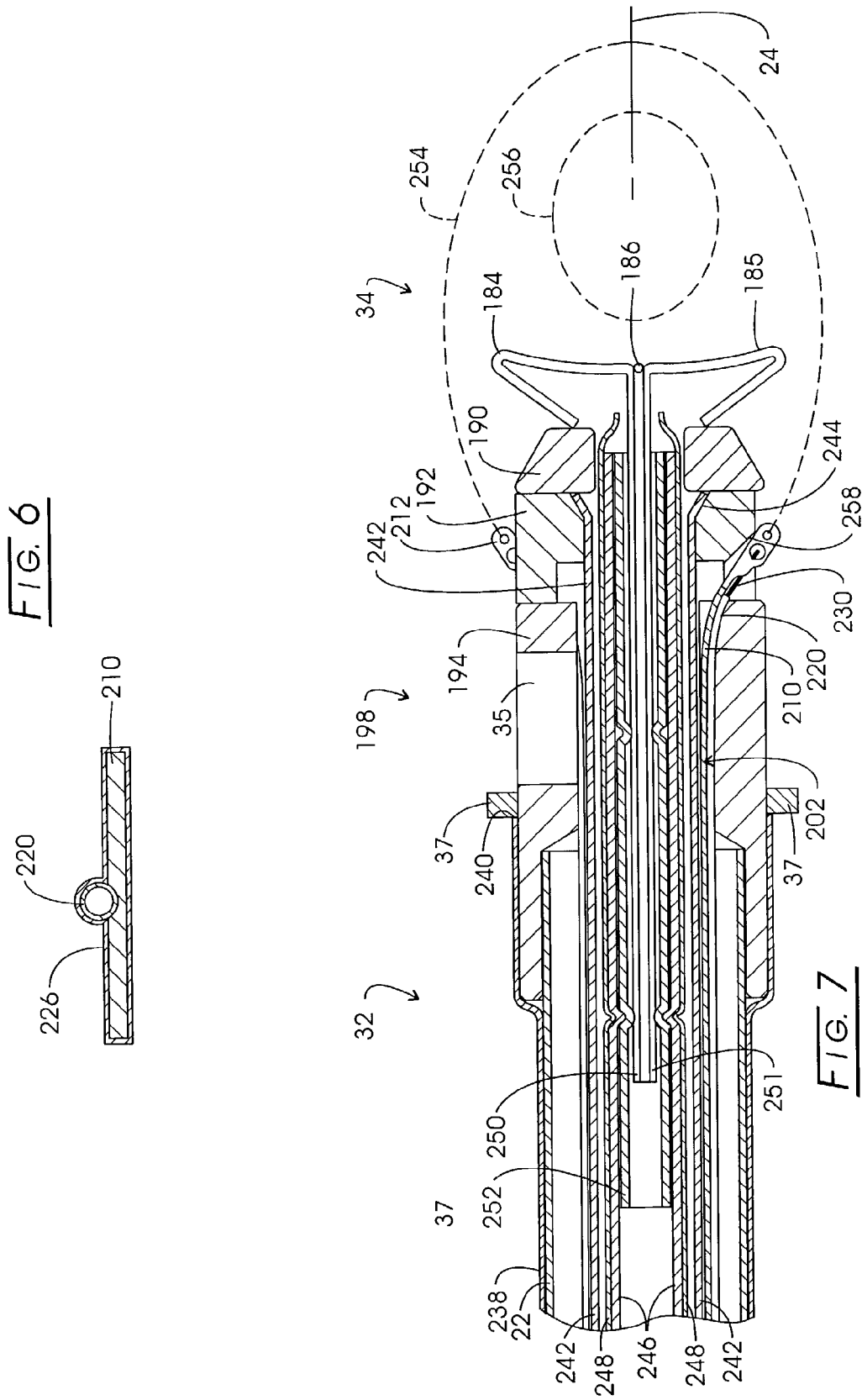

TIME (seconds)

TIME (seconds)

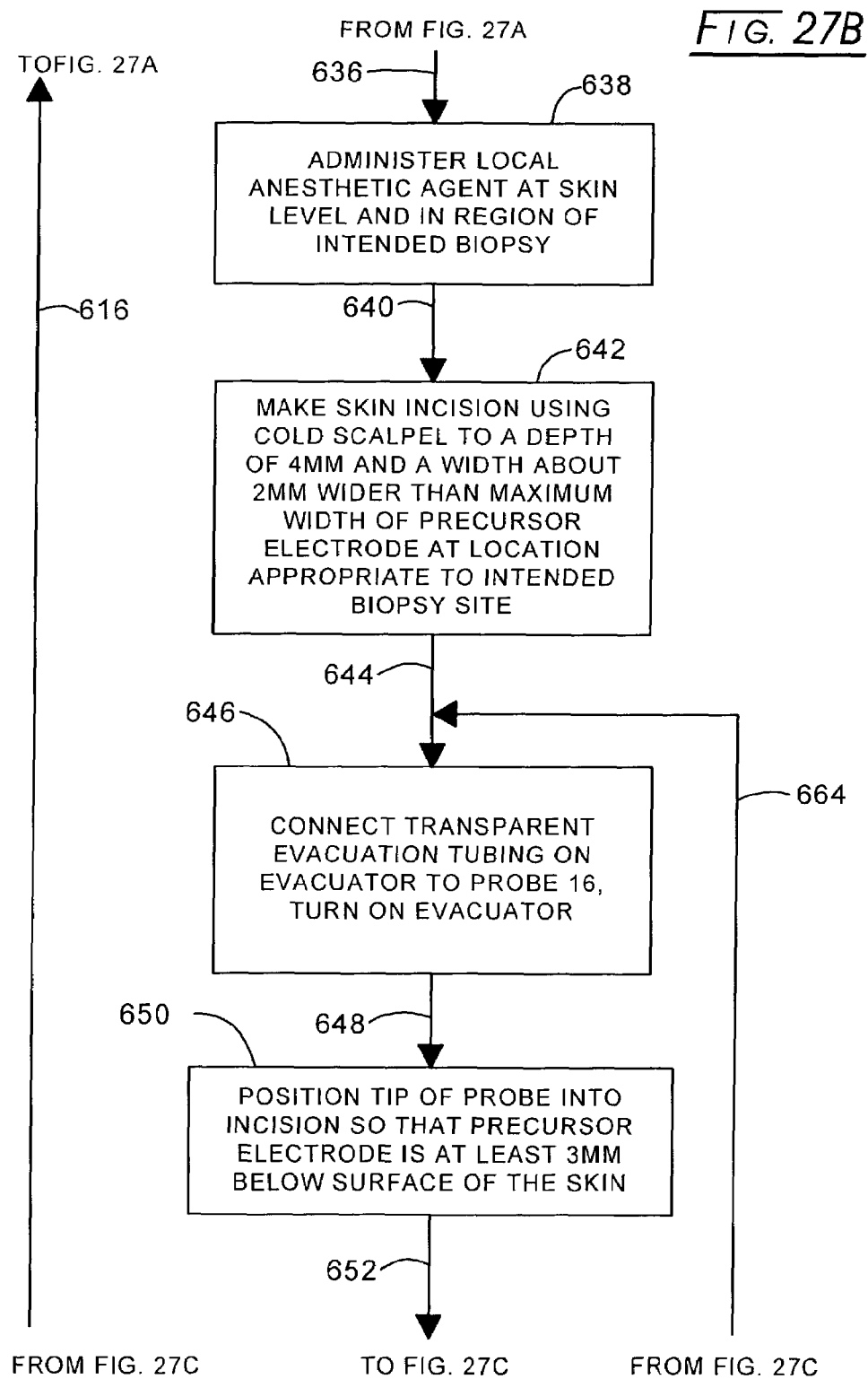

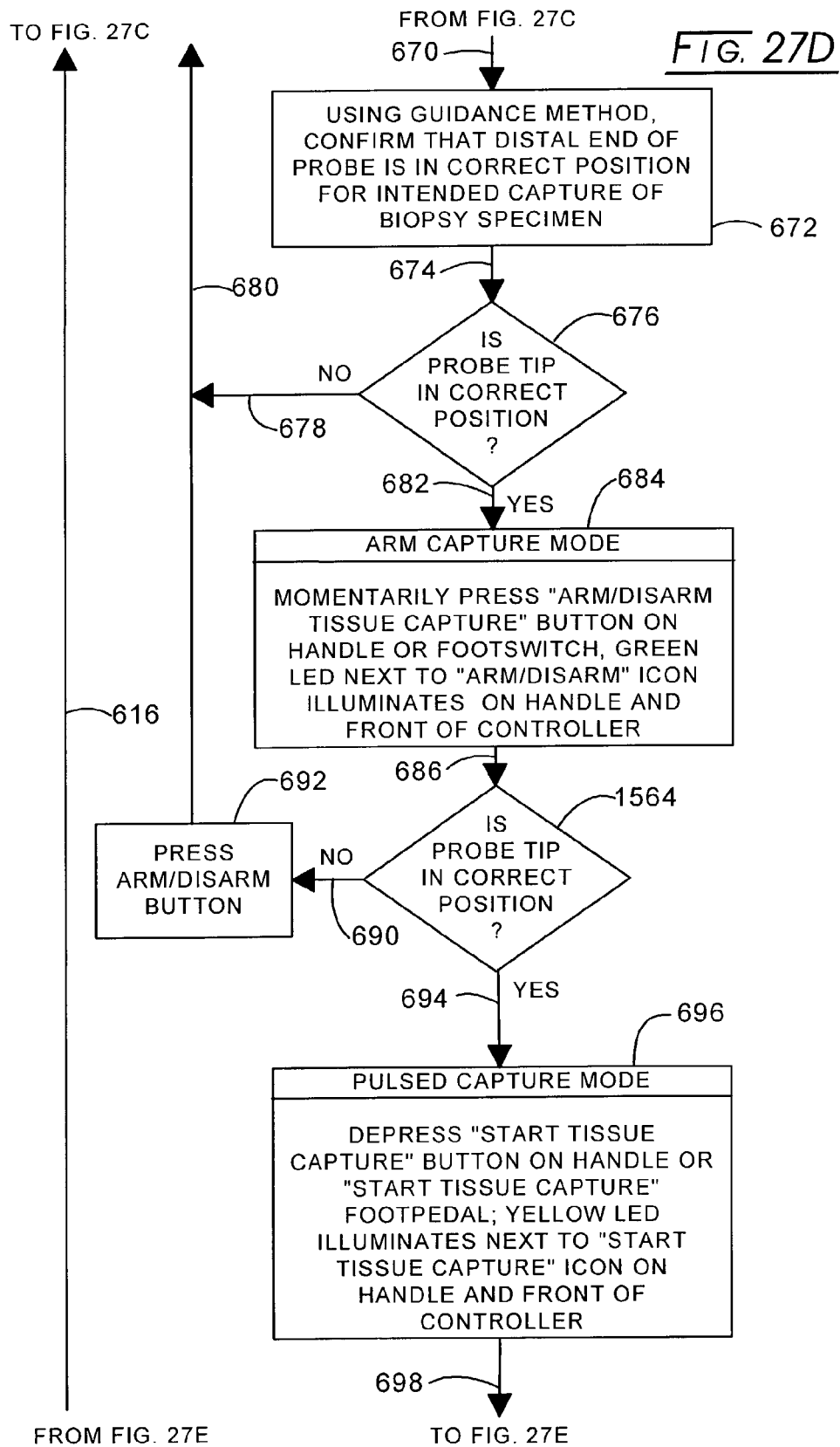

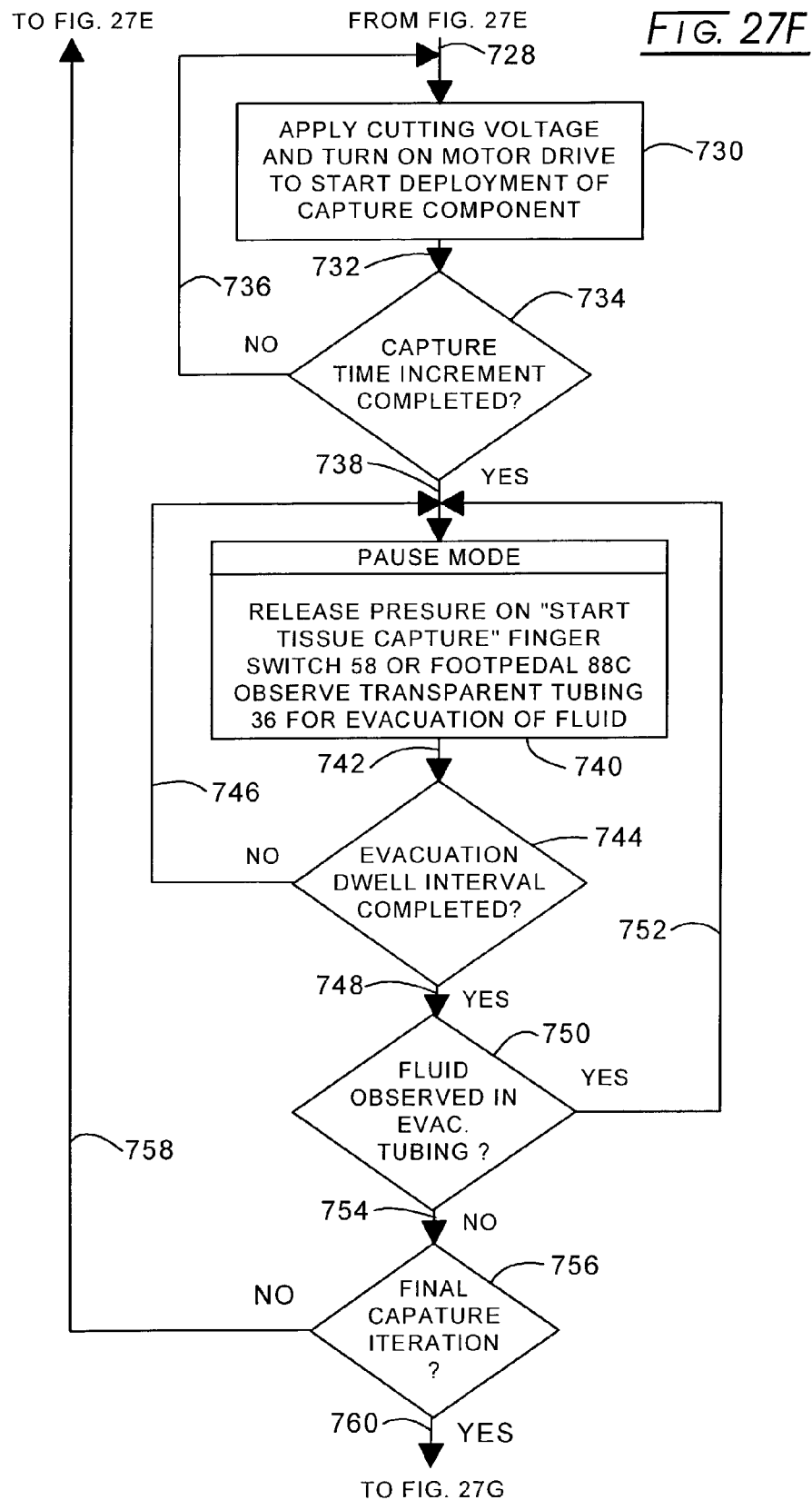

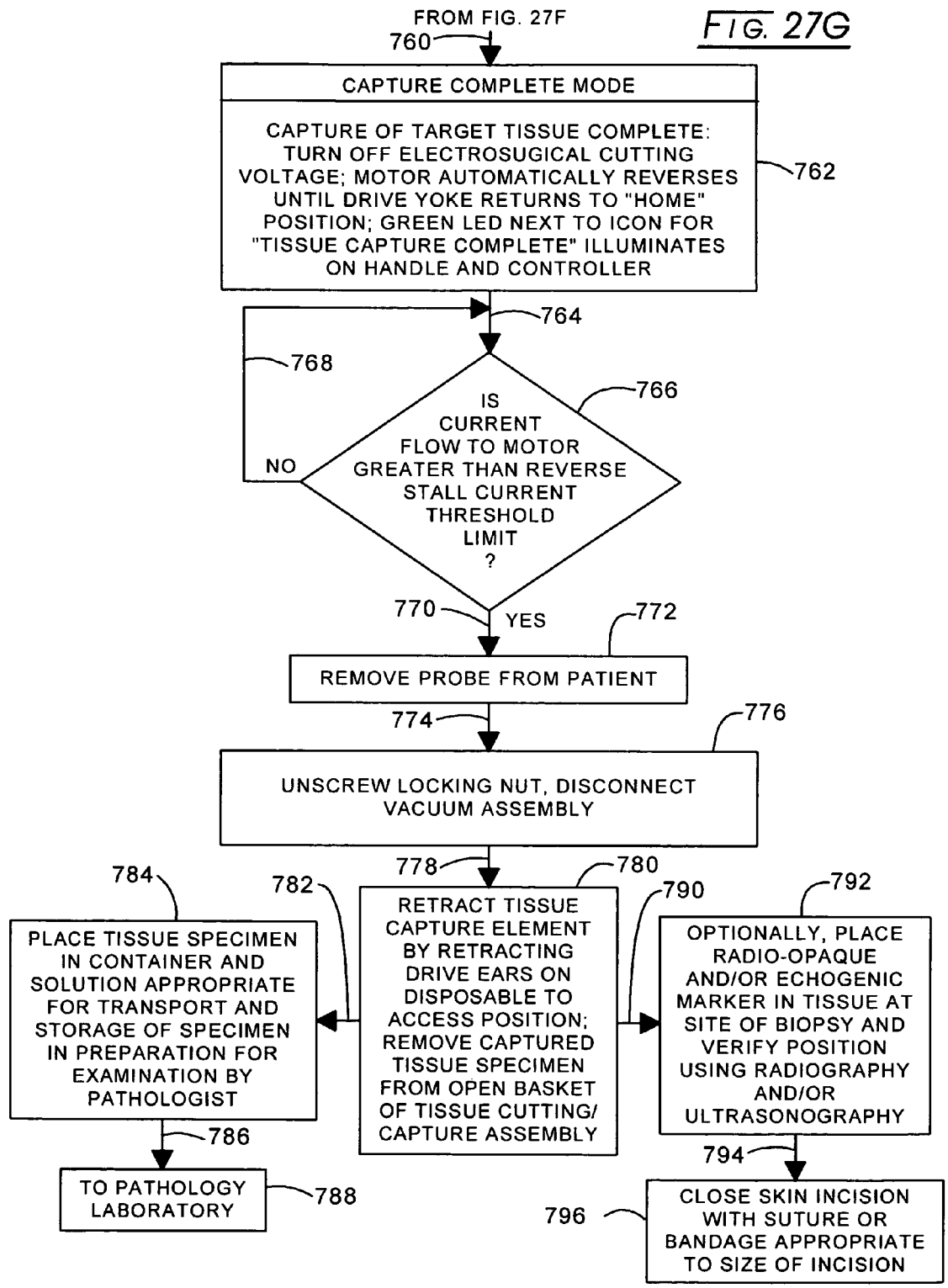

ELECTROSURGERY WITH INFILTRATION ANESTHESIA

CROSS-REFERENCE TO RELATED APPLICATIONS

This application claims the benefit of U.S. Provisional Application No. 60/385,236, filed May 31, 2002, is a continuation-in-part of U.S. application Ser. No. 09/904,396 filed Jul. 12, 2001, now U.S. Pat. No. 6,471,659 issued Oct. 29, 2002, which, is a continuation-in-part of application Ser. No. 09/472,673 filed Dec. 27,1999, now U.S. Pat. No. 6,277,083.

STATEMENT REGARDING FEDERALLY SPONSORED RESEARCH

Not applicable.

BACKGROUND OF THE INVENTION

The use of electrotherapy by medical investigators historically reaches back to the eighteenth century. In that era, electrotherapy static generators were the subject of substantial interest. As the twentieth century was approached, experimentation applying high frequency currents to living tissue took place, d'Arsonal being considered the first to use high frequency currents therapeutically. The use of high frequency currents for the purpose of carrying out electrosurgical cutting and the like was actively promoted in the 1920s by Cushing and Bovie. In the 1970s, solid state electrosurgical generators were introduced, and a variety of such generators now are available in essentially all operating theatres.

When high frequency currents are used for cutting and coagulating, the tissue at the surgical site is subjected to controlled damage. Cutting is achieved by disrupting or ablating the tissue in immediate apposition to the excited cutting electrode, i.e., slightly spaced before it so as to confront a gap and tissue resistance combination which will support the formation of a cutting arc. Continuous sine waveforms generally are employed to carry out the cutting function where tissue cells adjacent to the electrode are vaporized. An advantage of this electrosurgical cutting procedure over the use of the cold scalpel resides both in an ease of cutting and a confinement of tissue damage to very small and shallow regions. In the latter regard, cells adjacent the cutting electrode arc are vaporized and cells only a few layers deeper are essentially undamaged. These cutting systems, in general, are employed in a monopolar manner wherein the cutting electrode is considered the active one and surgical current is returned from a large, dual component dispersive electrode coupled with the skin of the patient at a remote location.

Coagulation also may be carried out using a high frequency generator source and is accomplished by denaturation of tissue proteins due to thermal damage. Interrupted or discontinuous waveforms typically are employed to carry out coagulation. Coagulation is considered generically as including:

(1) fulguration in which tissue is carbonized by arc strikes,
(2) desiccation in which the cells are dehydrated, and
(3) white coagulation in which tissue is more slowly heated to a coagulum. The interrupted wave based coagulation procedure has been carried out with both monopolar and bipolar systems.

In order to obtain cutting with hemostasis to arrest bleeding, present day electrosurgical generators may be controlled to blend cutting and coagulating waveforms. To achieve this blend, for instance, a lower amplitude continuous sine waveform is combined with higher amplitude coagulate pulses prior to output voltage elevation by power amplification procedures or the like.

The electrosurgical cutting reaction has been the subject of considerable study. In this regard, some investigators observed that cutting is achieved as the electrical conduction of current heats the tissue up to boiling temperatures and the cells are basically exploded as a result of the phase change. Another, parallel mechanism has been described wherein, as an intense electromagnetic field impinges on absorbing tissue, an acoustic wave is generated by the thermal elastic properties of the tissue. The origin of the pressure wave lies in the inability of the tissue to maintain thermodynamic equilibrium when rapidly heated. See generally:

"Electrosurgery" by J. A. Pierce, John Wiley & Sons New York, N.Y.

Paramount to the cutting procedure is the generation of an arc within the evoked vapor phase. When cutting is being performed, the cutting electrode is not in mechanical contact with tissue, but rather rides on a vapor film as it is moved through the tissue. Thus, it is the separation between the cutting electrode and tissue which allows the possibility for arc formation while cutting. With the existence of this arc, current flow is highly confined, arcs by their nature being quite localized in both space and time, consisting of very short high current density discharges.

Electrosurgical generators generally are configured to derive a requisite arc formation with an active electrode of fixed geometry. For instance, the active electrodes may take the shape of a rod or spade-shaped scalpel. Arc formation requires technique on the part of the surgeon, the electrode being gradually moved toward target tissue until the spacing-based impedance is suited for striking an arc. The energy creating the arc typically is generated by a resonant inverter operating at an RF frequency. Control over such inverters is problematic, inasmuch as the arc represents a negative dynamic impedance. In general, some regulation of voltage feeding the RF inverters is carried out, however, overall output control is based upon a power level selection. Inverter control by output voltage feedback generally has been avoided due principally to the above-noted load characteristics of the necessary arc. Such attempted control usually evolves an oscillatory instability. Accordingly, power-based control is employed with marginal but medically acceptable output performance. In this regard, the environment of the arc sustaining electrode-tissue gap may change in the course of forming an incision. Upon loss of the arc, correction is made by backing the electrode away to increase or reestablish requisite tissue-gap resistance and/or by manually adjusting a generator knob to turn up its power output. However, there are limits to the latter adjustment. Should the tissue/arc resistance encountered by the generator drop excessively, to avoid excessive power generation, the generators will, in effect, turn off. This is a characteristic of all electrosurgical generators since there is a well-known relationship between output power (P), applied voltage (V) and tissue and gap resistance (R) which may be expressed as follows:

$$P = V^2/R$$

As resistance (R) continues to decrease voltage (V) must decrease to prevent output power (P) from increasing to such impractical or power cutoff levels to defeat an electrosurgical procedure. A somewhat common reaction to an apparently unrecoverable loss of cutting arc has been to fault the equipment and return to the procedure with replacement generators and cutting electrodes.

Currently developing electrosurgically implemented medical instrumentation often involves active cutting electrodes of highly elaborate configuration with a geometry which alters active surface areas in the course of a procedure, for example, isolating and then capturing a target lesion. One such instrument is described in U.S. Pat. No. 6,277,083 by Eggers, et al., entitled "Minimally Invasive Intact Recovery of Tissue", issued Aug. 21, 2001. This instrument employs an expandable metal capture component supporting forwardly disposed, arc sustaining electrosurgical cutting cables. Those cutting cables, upon passing over a target lesion, carry out a pursing activity to close about the target tissue establishing a configuration sometimes referred to as a "basket". To initially position the forward tip of the involved instrument in confronting adjacency apposite the targeted tissue, an assembly referred to as a "precursor electrode" is employed. In the latter regard, the forwardmost portion of the instrument tip supports the precursor electrode assembly. That electrode assembly is initially positioned within a small incision at the commencement of the procedure, whereupon it is electrosurgically excited and the instrument tip then is advanced to a target confronting position.

An improved design for the instrument, now marketed under the trade designation "en-bloc" by Neothermia Corporation of Natick, Mass., is described in co-pending application for United States patent by Eggers, et al., entitled "Minimally Invasive Intact Recovery of Tissue", Ser. No. 09/904,396, filed Jul. 12, 2001 and assigned in common herewith now U.S. Pat. No. 6,471,659, issued Oct. 29, 2002. To accommodate for the arc-to-tissue resistance variations encountered by an electrosurgical generator in driving the dynamically altering cutting surface, an improved electrosurgical generator was developed by Eggers, et al. Described in application for U.S. patent application Ser. No. 09/904,412 entitled "Electrosurgical Generator", filed Jul. 12, 2001, now U.S. Pat. No. 6,740,079, issued May 25, 2004, and assigned in common herewith, the generator exhibits constant voltage and variable power attributes addressing the requirement for sustaining an arc at a dynamic electrode assembly. The generator design also recognizes the operational aspect of initially creating or "striking" an arc both at the precursor electrode assembly and at the capture component cutting cables at the outset of a procedure. At this initial part of a procedure, the electrodes will be embedded or in direct contact with tissue. The conventional surgical technique of spacing the cutting electrode from tissue to start an arc thus is not a practical approach to arc formation. To create an arc at procedure commencement or restart, the generator elevates a control voltage to an extent effecting arc creation at an elevated power level for a boost interval of time which is relatively short but heretofore elected to assure arc creation. For example, the enabling boost control signal has been sustained for 375 milliseconds. The generator is marketed as a "Model 3000 Controller" by Neothermia Corporation (supra).

Studies also have revealed that the electrical resistance characteristics encountered by electrosurgical generators and their associated instruments will vary quite widely in dependence upon the resistivity characteristics of involved tissue. Accordingly, for given electrosurgically based systems, optimization of the power vs. resistance profile is called for to avoid loss of arc on one hand, and to avoid tissue specimen damage due to excessive power application on the other hand.

Surgical procedures, including those described above, are increasingly being performed using local anesthesia in place of general anesthesia with the benefit of shorter post-surgery recovery time, shorter hospital stay, lower risks to patients associated with general (total body) anesthesia and lower associated procedure and/or hospitalization costs. Local anesthetic agents are weakly basic tertiary amines, which are manufactured as chloride salts. The molecules are amphipathic, and have the function of the agents and their pharmacokinetic behavior can be explained by the structure of the molecule. Each local anesthetic has a lipophilic side; a hydrophilic-ionic side; an intermediate chain, and, within the connecting chain, a bond. That bond determines the chemical classification of the agents into esters and amides. It also determines the pathway for metabolism. Local anesthesia is commonly administered (1) in the spine (caudal and epidural anesthesia), (2) between the ribs (inter costal anesthesia), (3) into the dental pulp (intra pulpal), (4) intravenous regional anesthesia (where a tourniquet is used to prevent anesthetic from entering systemic circulation, Bier block), (5) regionally injected anesthetic which forms "walls" of anesthesia encircling the operative field (field block) and (6) highly localized injection of the anesthetic close to the nerves located within the operative field (nerve block). In each of these approaches, the active anesthetic drug is administered for the purposes of intentionally interrupting neural function and thereby providing pain relief.

A variety of local anesthetics have been developed, the first agent for this purpose being cocaine which was introduced at the end of the nineteenth century. Lidocaine is the first amide local anesthetic and the local anesthetic agent with the most versatility and thus popularity. It has intermediate potency, toxicity, onset, and duration, and it can be used for virtually any local anesthetic application. Because of its widespread use, more knowledge is available about metabolic pathways than of any other agent. Similarly, toxicity is well known.

Vasoconstrictors have been employed with the local anesthetics. In this regard, epinephrine has been added to local anesthetic solutions for a variety of reasons throughout most of the twentieth century to alter the outcome of conduction blockaid. Its use in conjunction with infiltration anesthesia consistently results in lower plasma levels of the agent. See generally:

"Clinical Pharmacology of Local Anesthetics" by Tetzlaff, J. E., Butterworth-Heinemann, Woburn, Mass. 2000

To minimize the possibility of irreversible nerve injury in the course of using local anesthetics, the drugs necessarily are diluted. By way of example, the commonly used anesthetic drug is injected intramuscularly to effect a nerve block or field block using concentrations typically in the range of 0.4% to 2.0% (weight percent). The diluent contains 0.9% sodium chloride. Such isotonic saline is used as the diluent due to the fact that its osmolarity at normal body temperature (for example 37° C.) is 286 milliOsmols/liter which is close to that of cellular fluids and plasma which have an osmolarity of 310 milliOsmols/liter. As a result, the osmotic pressure developed across the semipermeable cell membranes is minimal when isotonic saline is injected intramuscularly and extracellularly. Consequently, there is no injury to the tissue's cells surrounded by this diluent since there is no significant gradient which can cause fluids to either enter or leave the cells surrounded by the diluent. It is generally accepted that diluents having an osmolarity in the range 240 to 340 milliOsmols/liter are isotonic solutions and therefore can be safely injected intramuscularly.

BRIEF SUMMARY OF THE INVENTION

The present invention is addressed to a method for carrying out surgical procedures wherein a target tissue is accessed through use of an electrosurgical cutting electrode assembly. Such electrode employment calls for a reliable formation of a cutting arc, and importantly, a sustaining of that cutting arc as it is advanced through animal tissue. The method described is one predicated upon a studied recognition of the significant resistance load variations encountered by an electrosurgical system in the course of its use. Such significant load variations may be witnessed in the course of very minor advancement increments of an electrode as it cuts through tissue. Power-resistance characteristics or profiles have been investigated with a purpose of generating arc sustaining power at variational load resistances while, at the same time, avoiding power application of an excessive extent which would otherwise damage the tissue being incised or a recovered tissue specimen for use in subsequent pathological examination. Recovery of undamaged, intact tissue volume specimens is essential for subsequent effective analysis in pathology.

Electrosurgically-based tissue specimen recovery, for example, from the female breast region conventionally has been carried out in conjunction with a preliminary administration by injection of a local anesthetic. Some benefits of this form of anesthesia are noted above. Currently most popular among the local anesthetic agents is lidocaine with or without minor additions of a vasorestrictive component such as epinephrine. These agents are combined with an isotonic diluent heretofore somewhat universally elected as an aqueous normal saline solution. Studies undertaken to evolve the instant methodology have indicated that the high conductivity of the conventional diluent serves in an excessive number of cases to defeat critical electrosurgical arc formation at otherwise electrically excited cutting electrodes. The noted studies have indicated that local anesthetic solutions with isotonic saline-based diluents, when infiltrated into tissue will lower the involved tissue electrical resistance in many instances to an extent causing electrosurgical generator shutdown due to excessive power involvement or inadequately high generator output voltage to sustain the electrosurgical arc essential to tissue "cutting". Minimum voltages are generally believed to be about 300 volts to about 600 volts, peak-to-peak, depending upon the geometry of the electrode and its contact area. In this regard, animal tissue exhibits a somewhat extensive range of resistivities. For such resistivities which are encountered during an electrosurgical procedure which are at the lower end of that range and for involved tissue which is infiltrated with a low resistivity anesthetic solution, procedural failures may be witnessed.

Where the subject of biopsy involves female breast tissue, the gland and duct anatomical characteristics encountered may tend to cause a collection and retention of accumulations or pockets of the local anesthetic solution. Where that solution is isotonic saline-based, cutting arc formation generally will be defeated with a failure of arc reformation when the solution containing pocket has been traversed by the advancing electrosurgical electrode.

The method of the invention addresses these consequences involved with the use of a local anesthetic with a saline-based diluent by substituting a diluent exhibiting significantly higher resistivity or, inversely, lower conductivity. Encountered tissue load resistances have been observed to significantly and advantageously elevate with the use of the latter diluent. Where the noted accumulations or pockets of a local anesthetic solution are encountered, for example, in the female breast glandular structure, while the electrode-supported arc may quench within the pocket of anesthetic solution, it reappears upon engaging tissue following a traverse of that pocket.

Studies herein described have been carried out utilizing the electrosurgical generator and capture component-based instrumentation described above. The procedural method has been altered with respect to this instrumentation, particularly with respect to the retrieval of tissue specimens from the female breast. A fluid evacuation system is employed with the instrumentation having a vacuum port assembly located in adjacency with the tip of the instrument. Deployment of the capture component is carried out in a pulsed or intermittent fashion wherein an arc is caused to be formed and the capture component is deployed or advanced for an incremental distance or time interval. Then a pause mode is entered into by the system which permits the evacuation system to remove any encountered pockets or accumulations of local anesthetic solution. The cutting arc is then reestablished and the capture component is advanced again on an intermittent basis until such time as full specimen capture is completed. Transparent conduiting is employed with the evacuation system such that the practitioner may observe whether fluids are being evacuated from the situs of the capture. As long as those fluids are seen to egress through the conduiting, the pause interval or mode is maintained.

Other objects of the invention will, in part, be obvious and will, in part, appear hereinafter.

The invention, accordingly, comprises the method possessing the steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 4 is a top view of a leaf assembly employed with the instrument of FIG. 2;

FIG. 5 is a general sectional view of a capture component and associated drive tube;

FIG. 6 is a sectional view of a leaf employed with the capture component shown in FIG. 5;

FIG. 7 is a partial sectional view of the forward region of the instrument of FIG. 2;

FIGS. 27A–27G combine as labeled thereon to provide a flow chart describing the method of the invention.

DETAILED DESCRIPTION OF THE INVENTION

The present invention addresses a method for carrying out surgical procedures utilizing an arc-creating electrosurgical electrode assembly. Such method looks in one aspect to the isolating and retrieving of a tissue sample volume, for the most part, evolved in the course of carrying out animal studies and trials with the above-identified surgical system of Neothermia Corporation. Accordingly, in the discourse to follow, the salient aspects of that system are described to afford an enhanced understanding of test data revealed herein. Certain of that test data is set forth in Appendices A and B annexed hereto, while other such data is assembled in tabular as well as graphic form.

Figure 1:
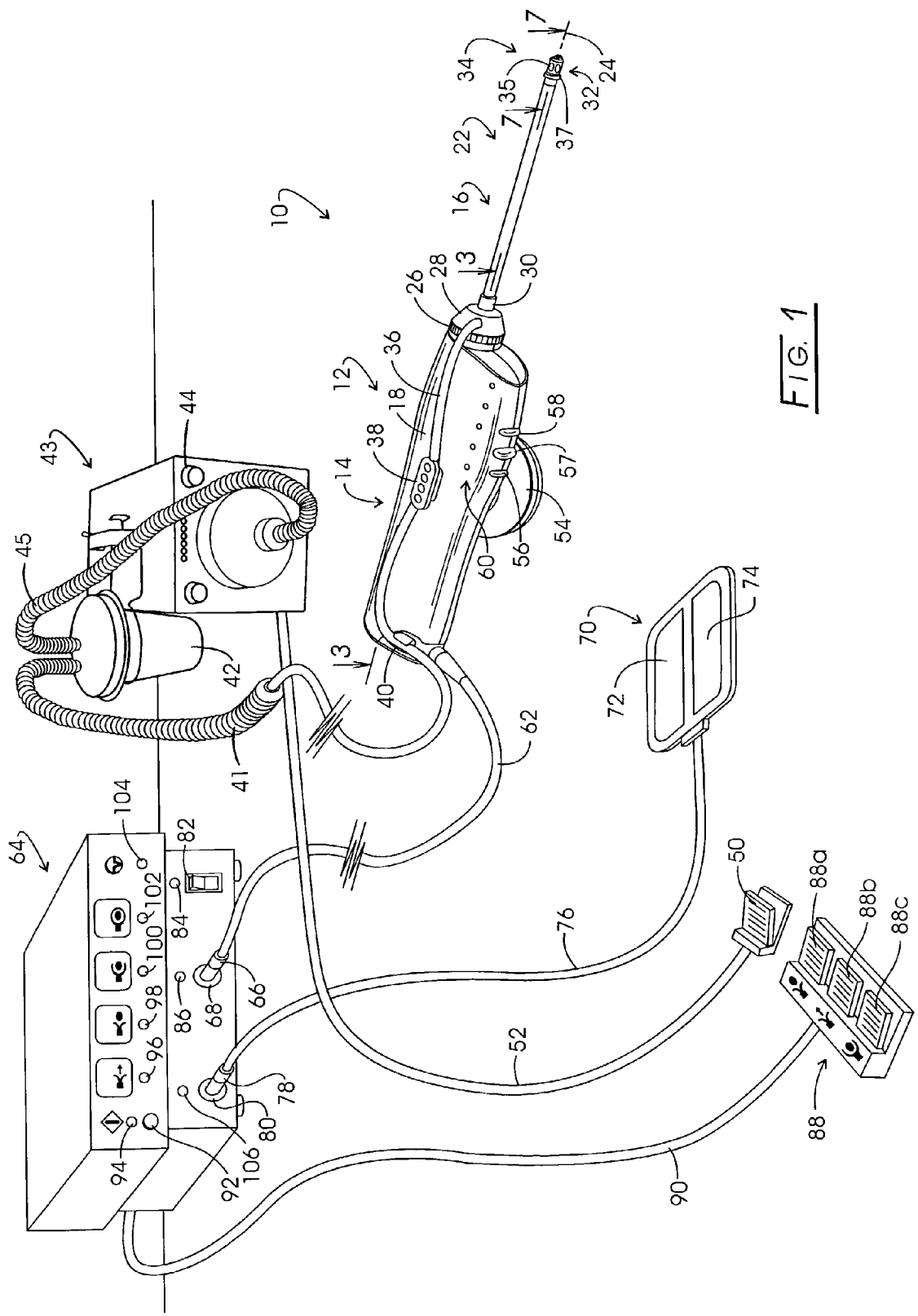
FIG. 1 is a perspective view of a system employing the method of the invention.

Referring to FIG. 1, the noted system for isolating and retrieving a target tissue volume is illustrated in general at 10. System 10 comprises a tissue retrieval instrument represented generally at 12 which includes a reusuable component represented generally at 14. Component 14 sometimes is referred to herein as the "handle". Instrument 12 additionally includes a disposable component represented generally at 16, the rearward portion of which is removably mounted within the polymeric housing 18 of reusable component 14.

Disposable component 16 includes an elongate delivery cannula represented generally at 22 which extends along a longitudinal cannula or instrument axis 24. The distal end of delivery cannula 22 extends through a rotatable, externally threaded connector 26. Connector 26 is threadably engaged within the housing 18. Delivery cannula 22 further extends through a suction manifold 28 which is a component of an evacuation system. Manifold 28 is retained in position on cannula 22 by a collar 30. The forward region of the cannula 22, as represented at 32, extends to a distal end or tip represented generally at 34. Suction or vacuum manifold 28 is in vacuum conveying and fluid receiving relationship through delivery cannula 22 with four intake ports identified at 35 at forward region 22. Two of those four intake ports 35 are revealed in the figure. Located adjacent intake ports 35 is a blocking ring 37 which functions to block any migration of steam or smoke along the outer surface of delivery cannula 22. Vacuum is conveyed to and fluid is received from suction manifold 28 via a flexible transparent polymeric tube 36. Tube 36 is shown to extend from manifold 28 into press fit connection with connectors 38 and 40, flexible tube or hose of larger diametric extent being shown at 41. Hose 41 extends to a fluid trap 42 which is in vacuum communication via flexible hose 45 with the suction input of a suction pump assembly 43. Vacuum or suction pump assembly 43 can be of a type marketed under the trade designation "VersaVac 2" by Stackhouse, Inc. of Palm Springs, Calif. Pump assembly 43 may be actuated into operation from a switch arrangement shown generally at 44 or through utilization of a foot switch 50 coupled to the pump assembly 43 via a cable 52.

Connectors as at 38 are positioned on each side of the housing 18 and function additionally to support a stabilizer handgrip, for example, the annulus-shaped grip represented at 54. Positioned at the forward portion of the housing 18 are three button switches 56–58 which function, respectively as an arm/disarm switch; an energize position switch; and a start tissue capture switch. Immediately above the switches 56–58 on each side of housing 18 are linear arrays of LED based indicator or cueing lights, one such array being represented generally at 60. The visual cues provided by the indicators at 60, from the forward region of housing 18 toward the rear region thereof provide a start/reset cue as a green light; a tissue capture complete cue provided as a green light; a start tissue capture cue (above switch 58) provided as a yellow light; an energize position cue (above switch 57) provided as a yellow light; and an arm/disarm tissue capture cue (above switch 56) provided as a green light. Energization and control is provided to the instrument 12 via a multi-strand cable 62 which connects with a combined control assembly and electrosurgical generator console represented generally at 64. Connection of the cable 62 with the console 64 is shown at a multi-lead connector 66 which is coupled to a console connector 68. The electrosurgically active electrode assembly of the instrument 12 performs in monopolar fashion. Thus, a conventional, relatively large, dispersive return electrode assembly as shown in general at 70 is positioned against the skin surface of the patient. Assembly 70 is configured as having two electrode components 72 and 74 which are connected via cable 76 and connector 78 to console connector 80. Alternatively, a return electrode may be positioned at the surface of delivery cannula 22 near its distal end in place of the illustrated use of return 70.

Power is supplied to the circuitry at console 64 upon actuation of an on/off switch 82. When switch 82 is in an "on" orientation, a green visual indicator LED 84 located above the switch is energized. Proper connection of the cable 62 and connector 66 with console connector 68 is indicated by an illuminated green LED 86 positioned above connector 68. This connection test is carried out by directing current to a coding resistor within housing 18. A three-pedal foot switch represented generally at 88 is coupled via a cable 90 to the rear panel of console 64. The three pedals, 88a–88c of switch 88 emulate and provide alternative switching with respect to button switches 56–58.

Visual cueing corresponding with that at housing 18 LED arrays as at 60 also is provided at the console 64. In this regard, a start/reset switch 92 is operationally associated with an LED indicator light 94 which illuminates in a green color upon actuation of that switch. A yellow position mode visual cue LED representing an energization of a precursor electrode at tip 34 is shown at 96. This LED provides a yellow output during the electrosurgical advancement of delivery cannula tip 34 into confronting adjacency with a targeted tissue volume. Next, a green, arm capture mode visual cue is provided by an LED 98 to represent an arming of the tissue capture feature of instrument 12. Once an arm/disarm switch as at 56 or 88a is depressed, the energize position switches as at 57 or 88b are no longer activatable. However, the practitioner may return to the position mode by again depressing an arm/disarm switch. A yellow capture mode visual cue is provided by an LED 100 to represent the start of and carrying out a tissue capture procedure and upon completion of such capture, a green capture complete mode visual cue is provided by a green LED 102. A pause mode condition is represented by the energization of a green LED 104. In general, the pause mode is entered during a procedure by releasing capture switch 58 or foot switch 88c. When in a pause mode, the active capture electrodes of the instrument 12 are not energized and deployment of the capture component is halted. Similarly, to reenter the capture mode the practitioner again depresses footswitch 88c or capture switch 58. Upon such reactuation of the chosen switch, the capture mode continues, in effect, from the orientation where it left off.

The importance of the evacuation system as above discussed will become apparent as the methods and techniques of the invention are descriptively unfolded. An assurance that the vacuum system is working, at least to the extent that the vacuum pump 43 is active, can be accomplished with a vacuum actuated switch (not shown) attached within a conduiting extending between pump 43 and the instrument 12. For example, unless such switch is actuated, the commencement of a procedure can be logically blocked by the control assembly within console 64.

At the time connector 78 of the return electrode 70 is coupled to console connector 80 and switch 82 is in a power on condition, a patient circuit safety monitor circuit (PCSM) carries out a self test. On subsequent actuation of start/reset switch 94, a fault test with respect to the two electrode components 72 and 74 is performed. In the event the latter test fails, then both visual and aural pulsating warning cues are activated, the visual cue being provided at a red LED 106 located adjacent connector 80.

Figure 2:
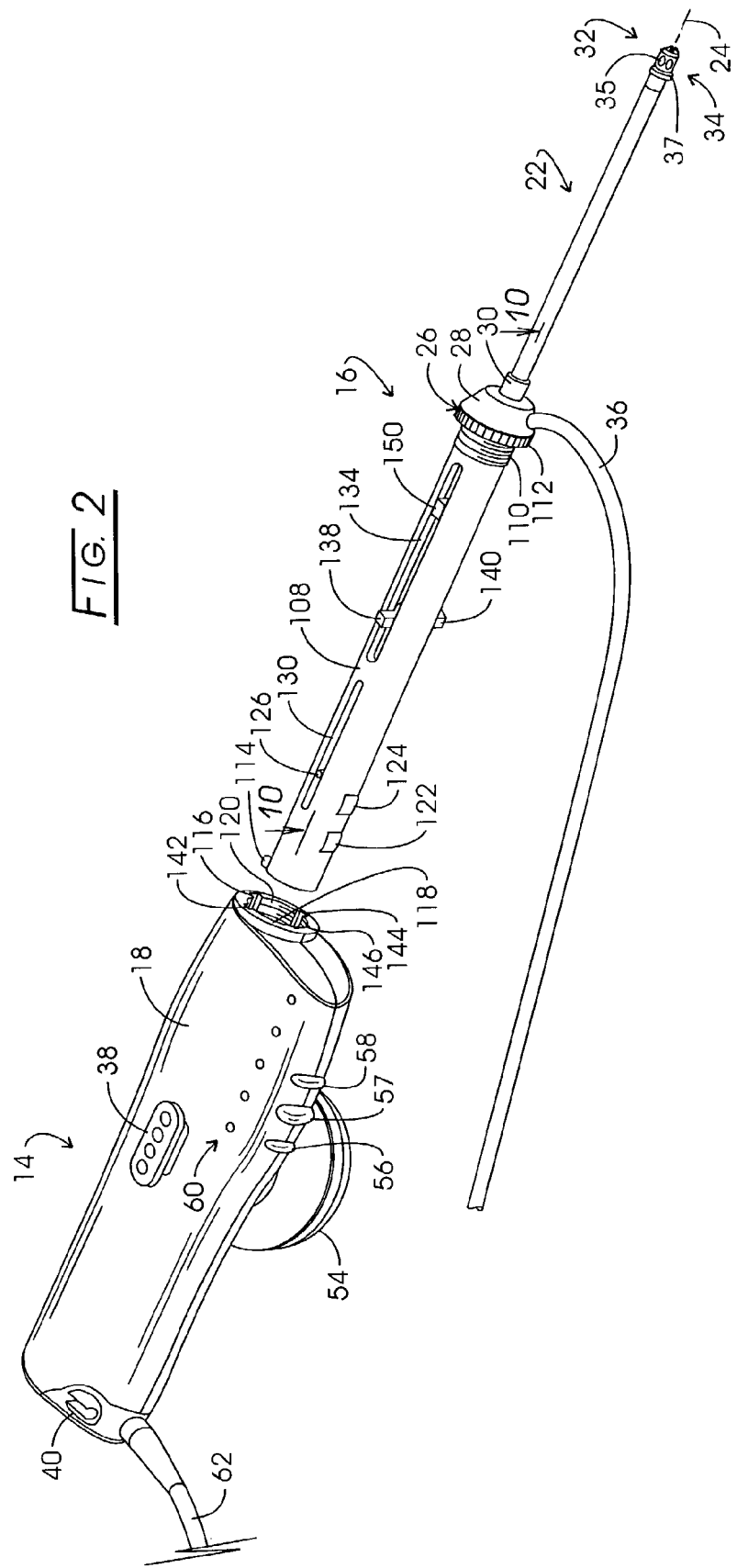
FIG. 2 is a perspective view of the instrument shown in FIG. 1 with a disposable component being shown removed from a reusable component.

Referring to FIG. 2 the disposable component 16 of instrument 12 is revealed in an orientation prior to insertion within the housing 18 of reusable component 14. This disposable component 14 is sometimes referred to herein as the "probe". In the figure, delivery cannula 22 is seen extending forwardly from a cylindrically-shaped support housing 108. The forward region of support housing 108 supports the rotatable connector 26. In this regard, it may be observed that the connector 26 is configured with external threads 110 which are fixed for rotation with a knurled flange 112. At the rearward end of support housing 108 there is located an upstanding indexing pin 114 which, during installation of the disposable component 16 is slidably received within an upwardly disposed elongate slot 116 extending internally along an elongate receiving cavity 118. Internal threads 120 within cavity 118 threadably engage the external threads 110 of connector 26 when the disposable component 16 is inserted within the reusable component 14.

Positioned opposite indexing pin 114 on support housing 108 are two, spaced apart electrical contacts 122 and 124 which are oriented to make wiping contact with corresponding electrical terminals disposed within housing 18 upon insertion of support housing 108 within the receiving cavity 118. Contacts 122 and 124 selectively receive electrosurgical cutting current which is applied respectively to a precursor electrode assembly at tip 32 and the electrosurgical cutting and pursing cables associated with a capture component retained within delivery cannula 22. Those pursing cables extend from the capture component within delivery cannula 22 to a cable terminator component, having guidance tabs or ears, one of which is revealed at 126 slidably mounted within an elongate stabilizer slot 130 arranged in parallel with axis 24. A corresponding guidance tab and slot combination is found at the opposite side of support housing 108. Located forwardly of the slots as at 130 are two additional elongate drive slots, one of which is shown at 134 similarly arranged in parallel with axis 24. The outwardly extending ears or guide tabs of a drive assembly drive member extend from these slots and are seen at 138 and 140. These ears or tabs 138 and 140 support rearwardly disposed driven surfaces which are used to impart forward movement to the drive assembly. This forward movement functions to deploy a capture component from delivery cannula 22. When the support housing 108 is installed within the receiving cavity 118 of housing 18, these tabs 138 and 140 pass through oppositely disposed notches shown respectively at 142 and 144 provided at the forward portion of housing 18. Similarly, a notch 146 is located forwardly within reusable housing 18 to permit passage of the electrical terminals 122 and 124. As is apparent, the procedure for installing the disposable component 16 within the reusable component 14 involves the sliding of disposable support housing 108 within the receiving cavity 118 and rotating knurled portion 112 of connector 26 to provide the engagement of threads 110 with threads 120. Finally, a tab 150 is seen extending through a forward portion of the drive slot 134. This tab is a component of a drive assembly safety stop 304 (FIG. 10) functioning to limit the extent of forward travel permitted by the drive member with ears 138 and 140 in accordance with a pre-selected capture component diametric extent.

Figure 3:
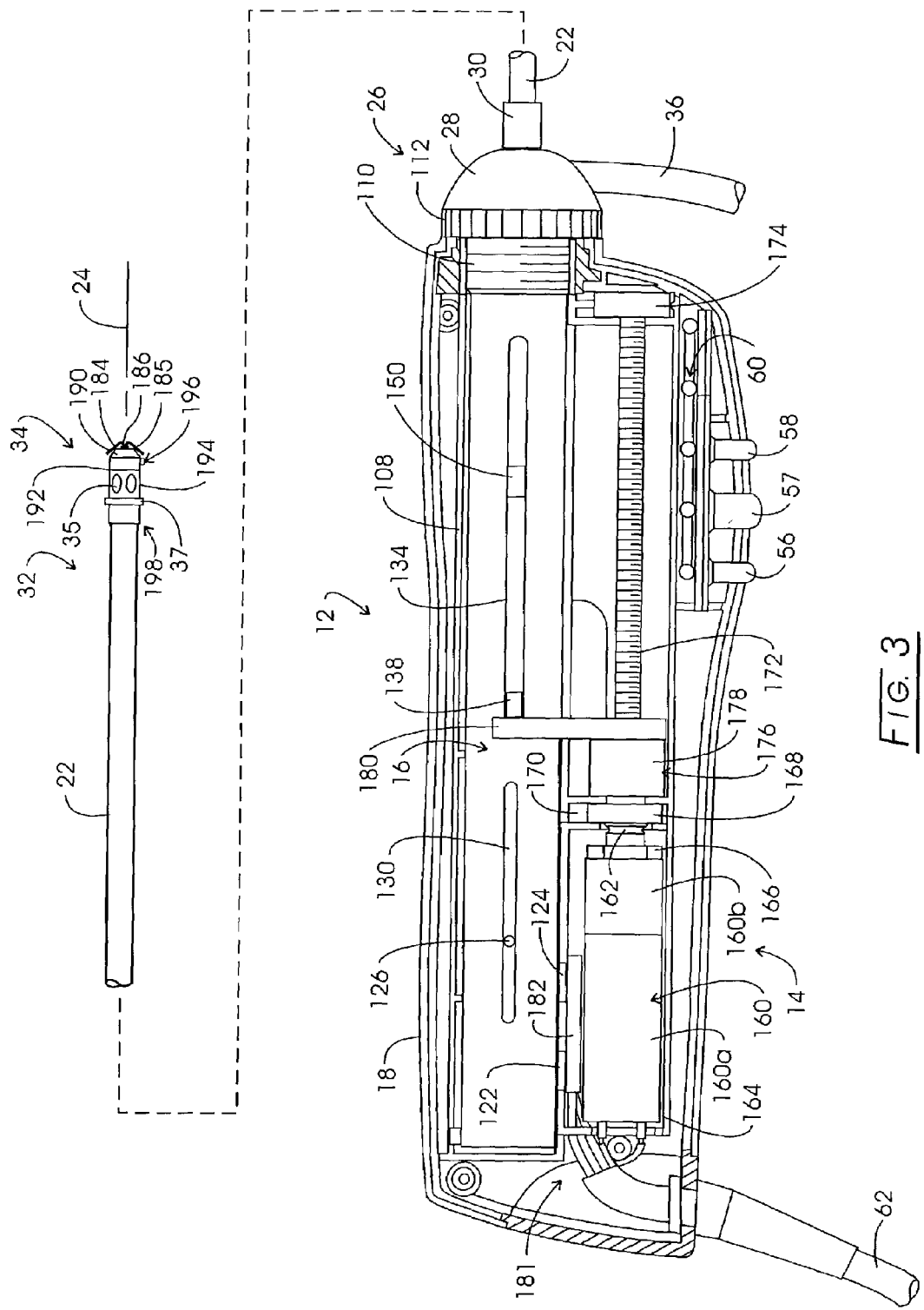
FIG. 3 is a partial sectional view of the instrument of FIG. 2.

Referring to FIG. 3, a sectional view is presented illustrating the operative association with the drive features retained within reusable component 14 and the driven features of the disposable component 16. In the figure, a motor assembly is represented generally at 160. Assembly 160 is formed of a d.c. electric motor 160a which is combined with a planetary gear assembly 160b. Assembly 160 provides a rotational output at a stainless steel bellows-shaped somewhat flexible coupler 162 and is located within a motor mount chamber 164. Within that chamber 164 the motor assembly 160 is permitted some self-aligning movement but is restrained from rotational movement by a torque stop component 166. For the instant embodiment, coupler 162 extends through a taurus-shaped fluid seal 168 located within a sealed chamber 170. This flexible seal 168 does not constrain the coupler 162 and permits the noted self-alignment of the motor assembly 160 with respect to an elongate rod-shaped translation component 172. Component 172 is seen extending forwardly to a rotatable and fixed connection with a thrust bearing 174. Bearing 174 provides support against all of the driving forces imposed from the motor assembly 160. In this regard, the rod-shaped threaded translation component 172 is threadably engaged with a transfer assembly represented generally at 176. Transfer assembly 176 comprises a ball screw or nut component 178 threadably engaged with the threads of component 172 and a generally Y-shaped yoke 180 which is configured having spaced apart drive members formed to extend to a position spaced from but aligned for driven engagement with the tabs or ears 138 and 140 (FIG. 2) of a drive member when the support housing 108 initially is inserted in the receiving cavity 118. To assure non-binding performance of the above drive components, it is necessary to avoid axial creep phenomena and the like which may be manifested as a compression of bellows 162. In general, a sleeve is provided over the output drive shaft of assembly 160, while a corresponding stepped-down diameter at component 172 provides a shoulder against which the coupler 162 abuts.

Electrosurgical cutting current as well as control inputs and outputs are introduced from cable 62 to the housing 18. Two of the multi-lead components, certain of which are revealed at 181, extend to a contact clamp 182 which retains two contacts for supplying electrosurgical cutting energy to contacts 122 and 124 of the disposable component 16.

FIG. 3 also reveals some details of the tip 34 of delivery cannula 22. That tip 34 is depicted as it is utilized for relatively smaller tissue volumes, for example, encompassed within a diametric extent of about 10mm. The tip incorporates four precursor electrode components arranged in a cross-shape symmetrically about longitudinal axis 24. Three of the electrosurgical cutting portions of the precursor electrodes are revealed at 184–186 located just forwardly of a truncated cone-shaped ceramic (alumina) protective tip 190. Tip 190 functions to provide an arc-resistant or arc isolating tip portion preventing its thermal breakdown. Rearwardly of ceramic tip 190 are polymeric tip components 192 and 194 which are coupled to delivery cannula 22. These tip components 192 and 194 are referred to in certain of the data compilations as "plastic". Component 194 is seen to carry the earlier-described suction ports 35 and blocking ring 37. Component 192 provides a ramp structure for a sequence of five thin stainless steel leafs of a capture component, the tips of which carry braided stainless steel pursing cables which are electrosurgically excited to create an arc for cutting purposes and which create a pursing action while cutting to form a cage-like structure around a targeted tissue volume. Alternatively, the precursor electrodes, leafs, pursing cable and cannula may be constructed of non-ferromagnetic material (e.g., titanium, nitinol) to enable use of this device with magnetic resonance image guidance of a biopsy procedure. Drive imparted to these capture component leafs emanates from the yoke 180 and drive member ears 138 and 140. Each of these leafs terminates in eyelets at its leading edge, one of which is represented generally at 196. The polymeric tip components 192 and 194 cooperate to form a guidance assembly represented generally at 198 which functions to direct the leafs, appropriately spaced apart and at a proper attack angle, in a capture maneuver. That attack angle for the instant embodiment is 45°.

Delivery cannula 22 has a relatively small diametric extent, for example, about 5 mm. Within its forward portion 32 there is disposed an earlier-noted capture component comprised of a pentagonally-shaped stainless steel elongate leaf structure with a leading edge formed with dual eyelets which carry a five pursing cable assembly. Referring to FIG. 4, the capture component is represented generally at 200 at a stage in its fabrication prior to the attachment of the noted pursing cables along with polymeric guide tubes. As revealed in the sectional view of FIG. 5, the capture component 200 has a generally pentagonal cross-sectional configuration initially chemically milled from flat stainless steel stock such that the forward portion 202 is formed with a sequence of five leafs having a thickness of 0.003 inch and a widthwise extent of 0.080 inch. The five leafs are shown in these figures at 210–214 and extend from a pentagonal base portion 218 (FIG. 4) to the noted dual eyelet tips 196. Each of the leafs 210–214 is chemically milled with a somewhat centrally disposed groove extending longitudinally along its length. Within each groove, as seen in FIG. 5, there is adhered a polyamide flexible guide tube. These guide tubes are quite small, having, for example, an outside diameter of about 0.020 inch and a wall thickness of about 0.0015 inch. The guide tubes are shown in FIG. 5 at 220–224 as being adhesively attached to respective leafs 210–214. Each of the guide tubes 220–224 slidably guides a pursing cable as shown respectively at 230–234. These multi-strand stainless steel cables have a diameter of about 0.005 inch. The polyamide guide tubes 220–224 are attached by initially adhesively coupling them to the noted troughs. Then, the tubes are bonded to a corresponding leaf within the chemically milled groove utilizing an electrically insulating coating material and process which achieves bonding and provides requisite electrical insulation for the entire capture component assembly 200. The coating, which has a thickness of about 0.001 inch, is a vapor-phase polymerized conformal coating marketed under the trade designation "Parylene". Parylene is the generic name for members of a polymer series. The basic member of the series, called Parylene C is poly-para-xylene, a completely linear, highly crystalline material. Such coatings are available from parylene coating service companies such as Specialty Coating Systems, of Indianapolis, Ind. Looking momentarily to FIG. 6, a cross sectional view of leaf 210 is revealed in combination with guide tube 220. A parylene coating is represented at 226.

FIG. 4 reveals the eyelet structure at the leading edge of capture component 200. The leading edge containing the eyelets are bent outwardly from the orientation shown prior to the attachment to and extension of cables through them. Further, the capture component 200 is weldably attached to a drive tube or drive member 236 which extends rearwardly into support housing 108 and into engagement with the drive member associated with the tabs or ears 138 and 140 (FIG. 2).

Referring to FIG. 7, the forward region 32 and tip 34 of delivery cannula 22 are revealed in sectional detail. In the figure, the delivery cannula 22 is seen extending forwardly to the earlier-described polymeric (polyetherimide) tip component 194. Delivery cannula 22 is electrically insulated with a five mil thick polyolefin shrink tube 238 extending to a border 240 at component 194. Next inboard from the internal surface of the delivery cannula 22 are the five capture component leafs in pentagonal configuration, portions of two of which being shown at 210 and 212. Note the now outwardly bent orientation of the eyelets for these leaf structures. Extending next inwardly inboard is a stainless steel support tube 242 which is mounted at the rearward portion of the support housing 108 of disposable component 16 and extends forwardly through delivery cannula 22 to a flared region 244 engaging polymeric tip component 192. This flaring is found to be helpful in permitting the support tube to overcome the rather substantial forwardly direct forces occurring during forward deployment of the capture component leafs and cables. Note, additionally, that the somewhat annular space between cannula 22 and support tube 242 provides a fluid evacuation and suction conduit which extends to the four suction or vacuum intake ports 35. Extending inside support tube 242 is an electrosurgical precursor electrode tube 246 which also extends to the rearward portion of support housing 108 for purposes of both support and receiving electrosurgical cutting energy transmitted through electrical contact 122 (FIG. 2). As the precursor electrode tube 246 extends rearwardly, it is electrically insulated from support tube 242 by a polymeric shrink wrap 248. The precursor electrodes are mounted as a subassembly of four stainless steel electrode wires having a generally elongate L-shape, two of which are shown in conjunction with the electrodes 184 and 185. In this regard, the elongate components of these electrodes 184 and 185 are shown respectively at 250 and 251 extending into a subassembly tube 252. Four such electrode assemblies are crimped inside of this tube 252 and that tube, 252, in turn, is crimped within the forward portion of the precursor electrode tube 246. It has been found that the utilization of four cutting surfaces for the electrodes, arranged in a cross-shaped pattern, provides preferable instrument positioning results. Such an arrangement of confronting electrode surfaces is revealed, for example, in connection with FIGS. 8 and 9. In general, the severing portions of the precursor electrodes will be extending normally to the longitudinal axis 24 of the instrument and will be configured to directly confront the tissue being severed during the insertion or placement of the instrument in confronting relationship to the involved tissue volume. FIG. 7 reveals an enlarged representation of the precursor electrodes in conjunction with a stylized locus of travel 254 for the pursing cable and leaf combination as they extend over and about a target tissue volume represented in phantom at 256. The configuration and relative dimensioning of the pursing cable electrodes and precursor electrodes is, for example, that involved with 10mm diameter tissue specimen capture as discussed in detail later herein. It may be observed from the shape of the cutting locus 254 that the instrument is called upon to sustain a cutting arc at the pursing cables while accommodating initially for an expanding surface area or pursing cable length and then a contracting one. Additionally, this arc must be sustainable for a variety of tissue environments. Accordingly, the electrosurgical generator will confront or "see" some variation in total electrical resistance as is established by the cuffing arc itself, the tissue with associated blood, and as discussed herein, the local anesthetic which will have been intramuscularly injected just prior to the commencement of the procedure.

As contrasted with conventional surgical procedures wherein an electrode of fixed configuration is utilized and the surgeon is called upon to manually space that electrode from tissue to be cut in order to strike an arc, with the instant procedure, both the precursor electrodes 184-187 and the arc supporting cables 230–234 at their confronting portions are initially and at any restart embedded in tissue as opposed to being spaced from the tissue surface. This necessary initial tissue engagement is ameliorated by the application of a boost voltage level to create an arc at the initiation of electrosurgical cutting, whether at the outset of the procedure or following a stop (pause) in the procedure. The boost condition (e.g., 1200–1400 volts, peak-to-peak) is present now for only a minimal boost interval sufficient to create a cutting arc. Such minimization of the boost interval is elected for the purpose of minimizing any arc induced damage (artifacts) to the captured tissue specimen. It is important that the tissue specimen be available for subsequent analysis in pathology. Accordingly, thermal injury to the biopsy specimen and surrounding healthy tissue is avoided notwithstanding the necessity of assuring the presence of a cutting arc when the system is within a capture mode.

FIG. 7 also reveals that polymeric tip component 194 functions as a guide for the leafs 210–214. Similarly, polymeric tip component 192 is configured with five ramps arranged at a 45° angle with respect to the instrument axis 24. One of those ramps is shown at 258 in conjunction with leaf 210. These ramps provide for the 45° angle of attack of leafs 210–214 as they emerge during a capture procedure.

In general, precursor electrodes 184–187 will have a tissue cutting and confronting length of about 6.5 mm to 7.0 mm for employment with a maximum effective capture diameter for the capture component 200 of 10 mm to 20 mm. Where that effective diameter expands above 20 mm up to 40 mm, the corresponding expanse of the precursor electrodes or their lengthwise confronting extent will be about 10 mm to 15 mm. When configured having one of the larger lengthwise extents, the electrodes are slightly canted forwardly and are made resilient so as to be capable of flexing forwardly as the electrosurgically excited pursing cables physically contact the precursor electrodes. During this procedure, the precursor electrodes are open-circuited and permitted to be reenergized as they are urged into alignment with the capture component leafs. This temporary reenergization of the longer precursor electrodes is found to be beneficial as the electrodes retract or bend toward the larger tissue samples being captured.

Figure 8:
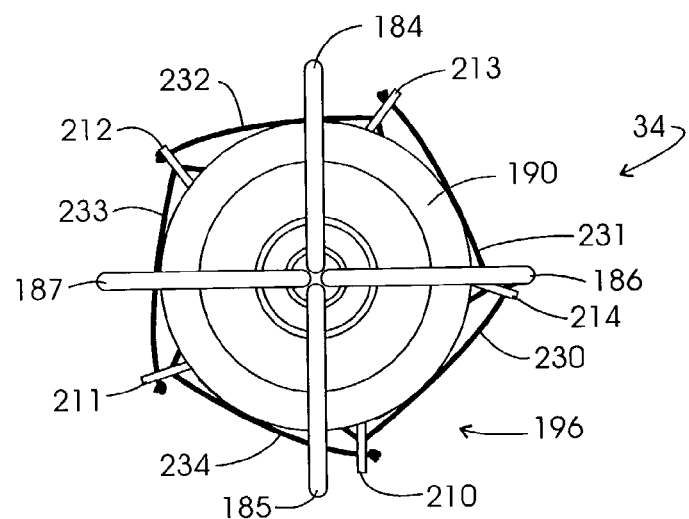
FIG. 8 is a front view of the forward portion of the instrument shown in FIG. 1 with components oriented prior to deployment of capture component leafs.
Figure 9:
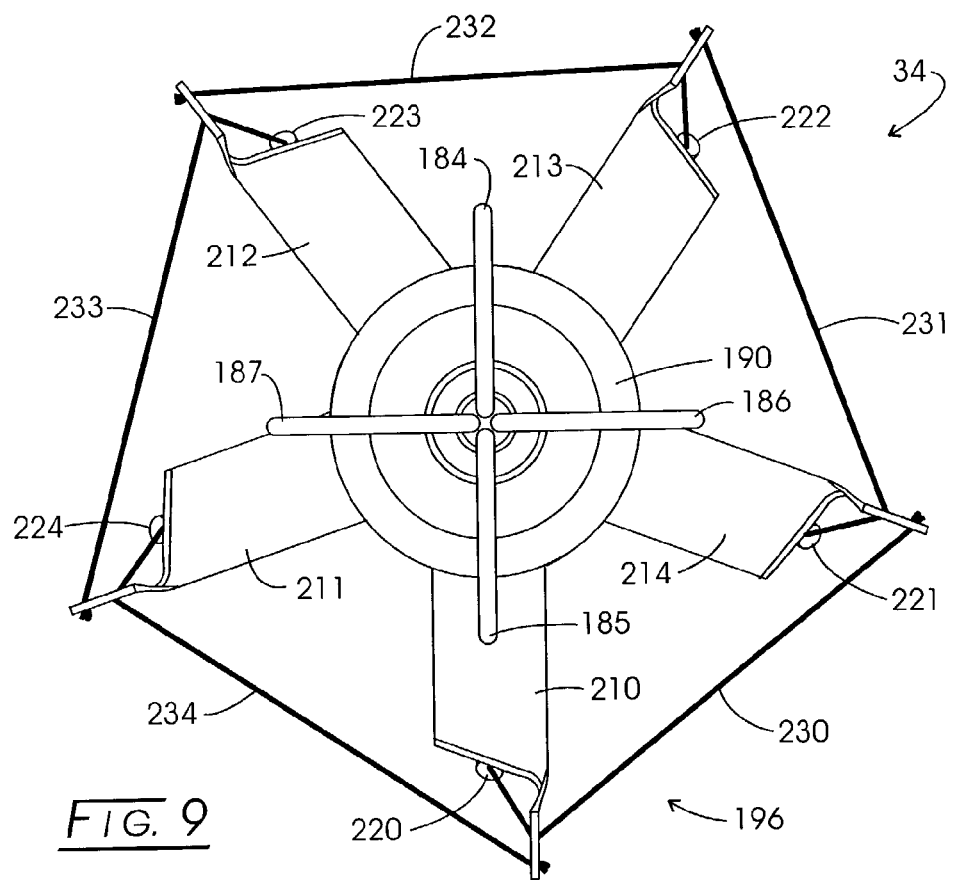
FIG. 9 is a front view of the forward portion of the instrument of FIG. 1 showing the orientation of components as the leafs of its capture component are being deployed.

FIGS. 8 and 9 present front views of the delivery cannula 22 tip 34, illustrating in particular the orientation of the precursor electrodes, as well as the leafs and cables in a retracted state in FIG. 8 and as the leafs and cables emerge in FIG. 9. In the procedure initiation orientation of FIG. 8, the active area extent exhibited by the electrosurgically cutting portions of cables 230–234 is somewhat small but slightly larger than at full pursing at the completion of the procedure. In FIG. 8, the five leaf tips of leafs 210–214 are visible in connection with portions of the pursing cables 230–234. When in this orientation, the precursor electrodes 184–187 will have been excited to form an arc while the instrument 12 is maneuvered into an orientation wherein the tip 34 is in confronting relationship with the targeted tissue volume, a geometry shown in stylized fashion in FIG. 7. The precursor electrode structure then is deactivated (open circuited) and the capture component 200 is deployed in conjunction with the arc-forming excitation of pursing cables 230–234 with electrosurgical cutting energy. However, inasmuch as the cables are embedded in tissue, a boost voltage is called for, for the noted boost interval adequate to evoke formation of a cutting arc between the active portions of cables 230–234 and confronting tissue. In general, that boost interval occurs before deployment of the leafs 210–214 commences.

FIG. 9 shows that as the leafs 210–214 are deployed, the pursing cables 230–234 are being "played out" and the effective diametric extent of the capture component is expanding to circumscribe the targeted tissue volume to be removed. To provide the expansion and subsequent pursing arrangement, note that cable 230 slides through guide tube 220 and is attached to the tip of leaf 214. Cable 231 slides through guide tube 221 and is attached to the tip of leaf 213. Cable 232 slides through guide tube 222 and is attached to the tip of leaf 212. Cable 233 slides through guide tube 223 and is attached to the tip of leaf 211; and cable 234 slides through guide tube 224 and is attached to the tip of leaf 210.

Figure 10:
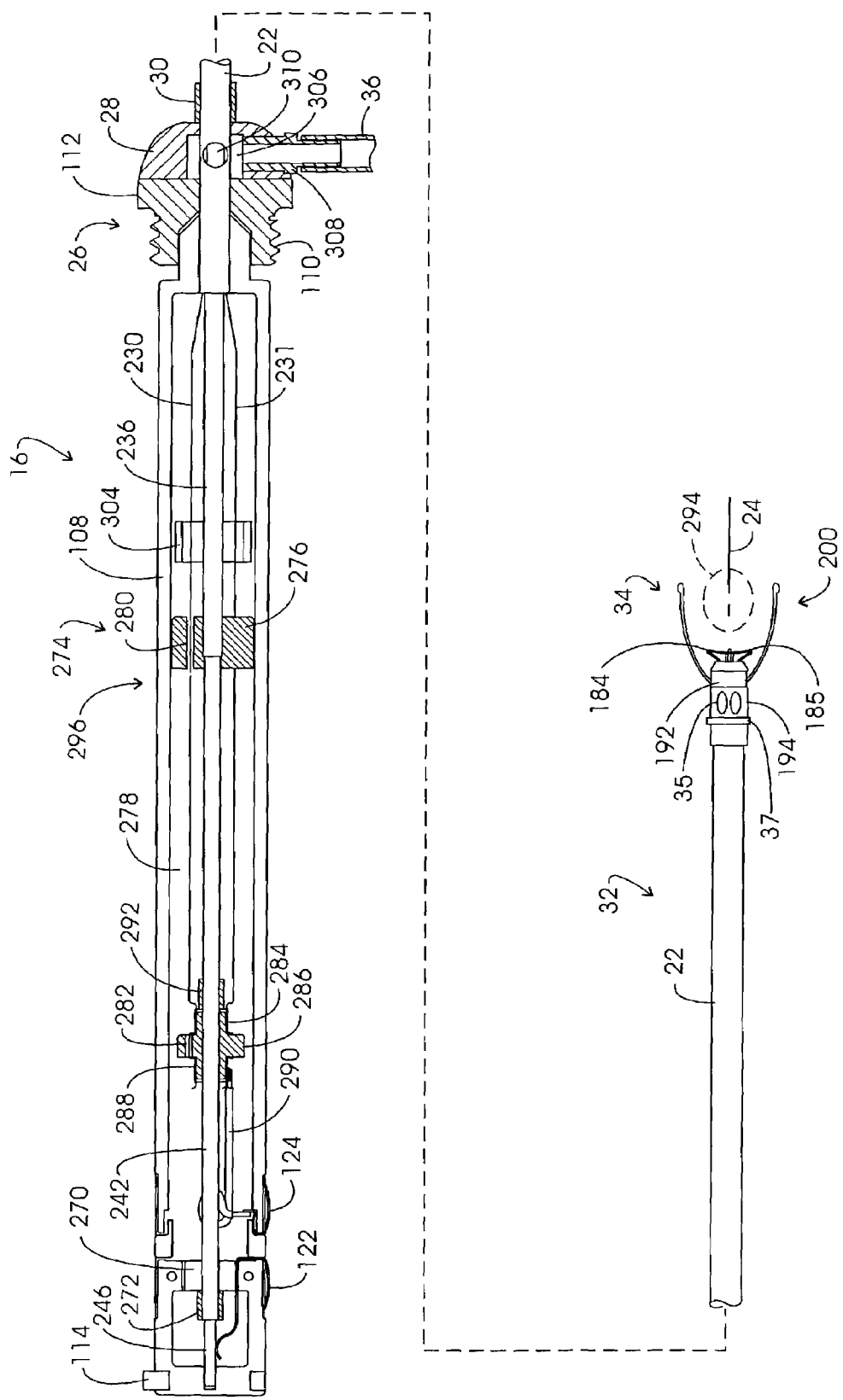
FIG. 10 is a partial sectional view of the disposable component of the instrument shown in FIG. 2 schematically showing a deployment of capture component leafs to a maximum diametric extent.

Referring to FIG. 10, a partial sectional view of the support housing 108 of disposable component 16 is provided. In the figure, the support tube 242 is seen to extend to engagement with a bulkhead 270 at the rearward portion of support housing 108. The tube 242 is retained in position by a collar 272. Extending through the support tube 242 is the earlier-described precursor tube 246 absent the insulative shrink wrap covering 248. Precursor electrode tube 246 is seen to be in abutting contact with electrical contact 122. With this arrangement, electrosurgical cutting energy can be conveyed from the contact 122 into the tube 246 and thence to the precursor electrodes 184–187. The rearward portion of the capture component drive assembly is represented generally at 274 and is seen to include the earlier-described drive tube 236 and a drive member 276. In the sectional view at hand, the integrally formed ears 138 and 140 (FIG. 2) of drive member 276 are not seen. However, note that it is coupled to the end of drive tube 236 and both that tube 236 and the drive member 276 slidably move over support tube 242 along the instrument axis 24. The yoke 180 described in connection with FIG. 3 engages the ears 138 and 140 to move drive assembly 274 forwardly by virtue of its abuttable engagement with ears or tabs 138 and 140 (FIGS. 2 and 3).

Pursing cables 230–234 extend rearwardly outboard of the drive tube 236 into the internal cavity 278 of support housing 108. Two of these pursing cables are symbolically represented at 230 and 231. These cables slidably extend through a corresponding five channels extending through drive member 276, one of which is shown at 280. The cables 220–234 extend further to a fixed connection with a polymeric cable terminator component 282. Component 282 is slidably mounted upon support tube 242 and includes a forward ferrule or collar 284 which is press-fitted over the cables 230–234. The cables then extend through a central flange portion 286 of component 282 for rigid and electrical connection with a rearward ferrule or collar 288. Collar 288, in turn, is coupled to a flexible electrical cable 290 which extends to an electrical connection with electrical connector 124. Cable 290 is of a length permitting it to follow the cable terminator component 282 as it slides forwardly. Accordingly, electrosurgical cutting energy is supplied to the cables 230–234 from connector 124, cable 290 and the ferrule 288.

Cable terminator component 282 is stabilized by two outwardly extending ears or tabs, one of which is described in connection with FIG. 2 as a tab 126 riding within stabilizer slot 130. Positioned forwardly of cable terminator component 282 is a cable stop 292. The collar-shaped stop 292 is adhesively fixed to support tube 242 at a location defining the maximum diametric extent developed by the leading edge of the capture component 200 leafs. That maximum diametric extent is represented in the instant figure in symbolic fashion as extending over a tissue volume and about halfway over a targeted tissue volume shown in dashed line fashion at 294. Note the proximity of the evacuation system vacuum intake ports 35 with respect to the cutting locus of the capture component 200. With the orientation of the capture component 200 as shown, the cable terminator component 282 will have commenced to abuttably engage the cable stop 292 to effect a tensioning of the pursing cables 230–234 as the drive assembly 274 continues to be driven forwardly by motor assembly 160, translation component 172 and transfer assembly 176 (FIG. 3). Finally, a drive safety stop mechanism comprised of stop member 304 is fixed within cavity 278 to limit the forward movement of drive assembly 274 beyond a location representing a full pursing or contracting of the capture component 200 for the elected maximum diametric extent of capture. Such unwanted movement may occur, for example, with the failure of cable stop 292 to halt forward movement of cable terminator component 282. As drive assembly 274 continues to be driven forwardly and drive member 276 approaches adjacency with safety stop member 304 the leafs of capture mechanism 200 will be pursed mutually inwardly together to define a confinement structure surrounding the tissue volume to be removed. Investigators have referred to the capture component in this fully capturing orientation as the "basket".

Referring again to FIG. 1, the procedure carried out with the system 10 initially involves the administration of a local anesthetic percutaneously at the site of an intended biopsy. Practitioners may, for example, inject an infiltration local anesthetic in about six locations spaced about 2 cm from the incisional location. The volume of the anesthetic solution which is infiltrated may, for example, be about 30 cubic centimeters (cc). Of importance, the solution constituting the local anesthetic should exhibit a resistivity or conductivity of value not reducing the amount of resistance the electrosurgical generator will confront, particularly during a capture mode. Preferably, the anesthetic agent will be combined with a diluent which will, in fact, improve, i.e., elevate the resistance "seen" by the electrosurgical system. Switch 82 is actuated to turn on the console 64 and cable 62 is attached at connector 68. Upon a successful testing of the connection, green LED 86 illuminates. The practitioner presses the start/reset button 92 on console 64, whereupon a patient safety circuit monitor test is carried out, the red LED 106 and an aural cue providing a pulsed output in the event of failure of this test. Disposable component 16 is mounted within the reusable component 14 and a skin incision using a cold scalpel to a depth of about 4 mm and a width of 2 mm, wider than the maximum width of the tissue volume to be removed is made. The evacuator or suction pump assembly 43 is turned on, for instance, from the foot switch 50 and the tip 34 of delivery cannula 22 is extended into the incision such that the precursor electrodes at its tip are at least 3 mm below the surface of the skin. Thus, these electrodes initially are embedded within tissue beneath the skin. A positioning mode then is commenced with either the depression and continued depression of energize/position foot switch 88b or housing 18 button switch 57 to effect first a boost then normal cutting energization of the precursor electrodes. LED 96 is illuminated as well as the corresponding LED at array 60. An aural cue is provided as a steady tone. The tip 34 of the delivery cannula 22 is advanced to a position of confronting adjacency with the tissue volume to be removed. Some practitioners prefer to carry out this positioning in increments by releasing and depressing foot switch 88*b* or housing 18 button switch 57 and then repressing the elected switch to continue the maneuver. When the final positioning of tip 34 is made, and the positioning mode is terminated (foot switch 88*b* is released or button switch 57 is released), the arm/disarm tissue capture switch 56 or foot switch 88*a* is depressed momentarily, the LED above switch 56 as well as LED 98 are illuminated, and system 10 enters in arm capture mode. During this mode, switches 57 and 88*b* are disabled. The start capture button switch 58 or foot switch 88*c* is then depressed and a capture mode commences. In this regard, the LED above switch 58 as well as LED 100 are illuminated and the motor 160*a* (FIG. 3) turns on to advance the yoke assembly 180 forwardly for an interval of one half second during which time motor current is monitored to assure proper operation. As the yoke 180 engages the ears 138 and 140 of drive member 276, motor assembly 160 is turned off. The electrosurgical generator applies first boost then normal cutting energy to the pursing cables 230–234 (FIG. 8) and following a one half second delay, motor assembly 160 is energized to start deployment of the capture component 200. During energization of the pursing cables 230–234 the noted steady tone is provided from console 64.

As one preferred procedure, the capture mode is carried out in an intermittent fashion. In this regard, the control assembly is actuated either automatically or by selective depression and release of either capture switch 58 or foot switch 88*c* for a capture interval. That interval may be, for example, about one second to about two seconds in duration. Release of foot switch 88*c* or switch 58 will cause the control assembly to enter a pause mode with the illumination of LED 104 and the deenergization of the pursing cables 230–234. This pause mode is continued for a pause interval which may extend from about 4 to about 6 seconds. It is during this pause interval that any pooled or accumulated local anesthetic solution which may have been encountered will be evacuated through the intake ports 35 of the evacuation system. During the pause mode, the operator observes transparent tubing 36 for detecting the presence of the clear local anesthetic solution and will retain the pause mode as long as that fluid is visually perceived. The control assembly then is again actuated, for instance, by depressing foot switch 88*c* or switch 58 and the capture mode is reentered with reassertion of boost energy for another capture interval. This intermitting procedure is repeated until full capture is effected, the capture component 200 orientation described in connection with FIG. 10 being reached. Where the capture mode is carried out in a continuous fashion, for example, with the continuous depression of foot switch 88*c* or switch 58, for a capture component 200 orientation of a maximum 10 mm diameter, a capture interval of about 6 seconds occurs. When a full capture orientation is reached, a forward stall condition is witnessed at motor 160*a*, forward energization of the motor assembly 160 is terminated and the motor is reversed to withdraw the transfer assembly 176 to its initial home position. LED 102 on console 64 as well as the corresponding LED output at array 60 are illuminated and the tone representing application of electrosurgical current is terminated. Delivery cannula 22 is removed from the patient, the vacuum pump assembly 43 is turned off and tube 36 is disconnected from hose 41. Connector 26 then is rotated to permit removal of the disposable unit 16. Upon removal of the disposable unit, ears or tabs 138 and 140 may be manually retracted to permit capture component 200 to assume an orientation, for example, represented at FIG. 10 for tissue specimen access. Alternately, the cables of the disposable component 16 may be cut to release the specimen. Looking again to FIG. 11, note that the capture component 200 is shown stylistically in a fully pursed or closed orientation having captured the target tissue volume 294. Cable terminator component 282 has remained in abutting contact with the cable stop 292 and drive member 276 is moved forwardly until the deenergization of motor 160.

Figure 11:
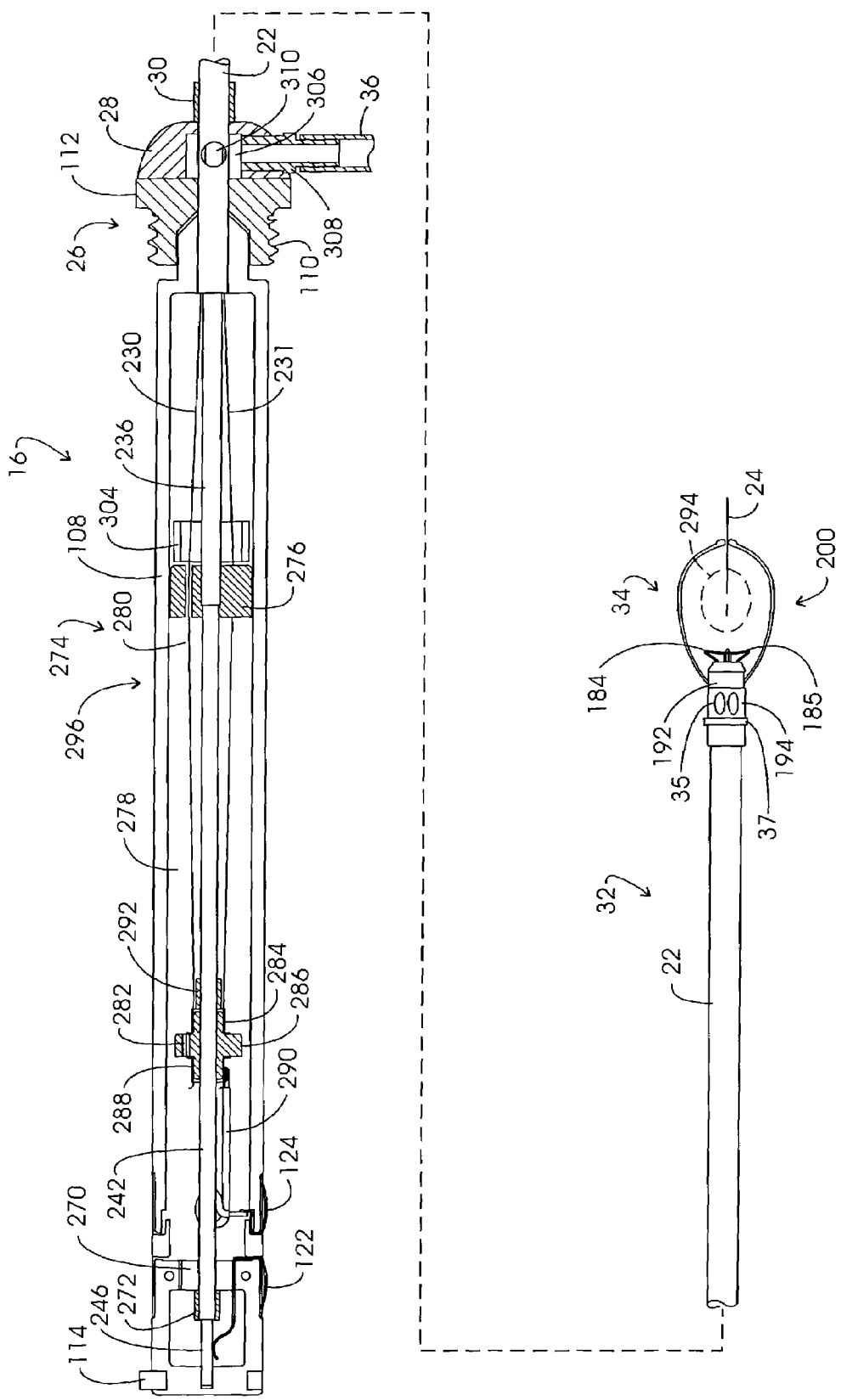
FIG. 11 is a partial sectional view of the instrument of FIG. 10 schematically showing the orientation of capture component leafs at the completion of capture of a tissue volume.

FIGS. 10 and 11 further reveal the configuration of the evacuation system at the location of suction manifold 28. In this regard, the manifold component 28 is shown having an internal manifold chamber 306 which communicates through a barb-like connector 308 with transparent tubing 36. Chamber 306 additionally communicates with the interior of delivery cannula 22 through an opening or aperture 310 extending therethrough. As described in connection with FIG. 7, the region between the interior surface of cannula 22 and support tube 242 provides fluid transfer and vacuum access to the four intake ports 35 at forward region 32.

A salient feature of the disposable component 16 of the system 10 resides in a structuring of the capture component and associated actuating system in a manner wherein the effective maximum tissue circumscribing diametric extent can be varied with the expedient of merely moving the cable stop component 284 to different locations along the longitudinal axis 24. It may be recalled that the collar-shaped cable stop component 284 is mounted upon support tube 242. This alteration of capture component diametric extent is illustrated in connection with FIGS. 12 and 13 in connection with a target tissue volume shown in phantom at 320. Comparing FIG. 12, for example, with FIG. 10, note that the cable stop member 284 now is fixedly positioned forwardly toward the latching component 296. The cable terminator component 286 is represented as having been drawn by cable 230–234 (here shown symbolically at 230 and 231) to adjacency with stop member 284. Cable 290 has been provided as being of extended length as represented at 290'. Drive member 276 and associated drive tube 236 have been moved forwardly with respect to their corresponding position shown in FIG. 10. Note that safety stop 304 has been positioned more forwardly than the arrangement shown in connection with FIGS. 10 and 11. Thus the leafs are moved mutually outwardly to a greater extent. The result is an enlarged capture diameter. For this embodiment, achieving a capture diametric extent of greater value, an expanded precursor electrode assemblage is called for to the extent that the captured or encapsulated tissue volume may be readily removed. In general, the lengthwise extent of each of the wire components of the precursor electrodes will be less than the effective maximum diametric extent of the capture component. As before, four precursor electrode components are employed, two of which are shown in solid line fashion at 322*a* and 322*b*. These precursor electrodes 322*a* and 322*b* are coplanar and arranged normally to a corresponding pair of such electrodes. With the arrangement shown, following the positioning of the tip of the delivery cannula 22 in confronting adjacency with the target tissue volume 320, electrosurgical cutting current is terminated at all precursor electrodes including those at 322*a* and 322*b*, the cutting drive circuit, in effect, being open-circuited. However, when the pursing cables commence to emerge from delivery cannula 22 in conjunction with capture component leaf movement, they will encounter the somewhat flexible electrode wires of the precursor electrodes as shown, for example, at 322a, 322b and re-excite them with electrosurgical cutting current. These electrodes then will be flexed forwardly toward the tissue sample volume as they are so re-excited to assume the orientations shown in phantom, for example, at 322a', 322b', and 322c'. In the latter case, the precursor electrode 322c' is, as noted, perpendicular to or normal to the electrodes 322a' and 322b'. A fourth such electrode (not shown) coplanar with electrode 322c' will be flexed similarly from the opposite side of the capturing region by the pursing cables. As the pursing cables continue to move forwardly under electrosurgical cutting current excitement, contact and electrical conduction with the precursor electrodes is terminated and the latter electrodes are permitted to flex rearwardly toward their original orientations in planes through the longitudinal axis of the instrument. Thus these precursor electrodes will be permitted to return through the tissue cutting paths evoked with their reengization by the pursing cables. It may be observed that the greater maximum diametric extent of the capture component 200 also will cause the creation of an area or length of pursing cable greater than in the embodiment of FIGS. 10 and 11. This will affect the total resistance confronting the electrosurgical system in terms of maintaining and developing an arc. In this regard, an increase from a 10 mm maximum diametric extent to a 15 mm diametric extent will lower the resistance exhibited by the pursing cables when at that diametric extent by a factor of about ⅓. Accordingly, the electrosurgical generator is called upon to exhibit a resistance vs. power characteristic capable of accommodating this lowered resistance effect in order to maintain a requisite cutting arc.

Figure 12:
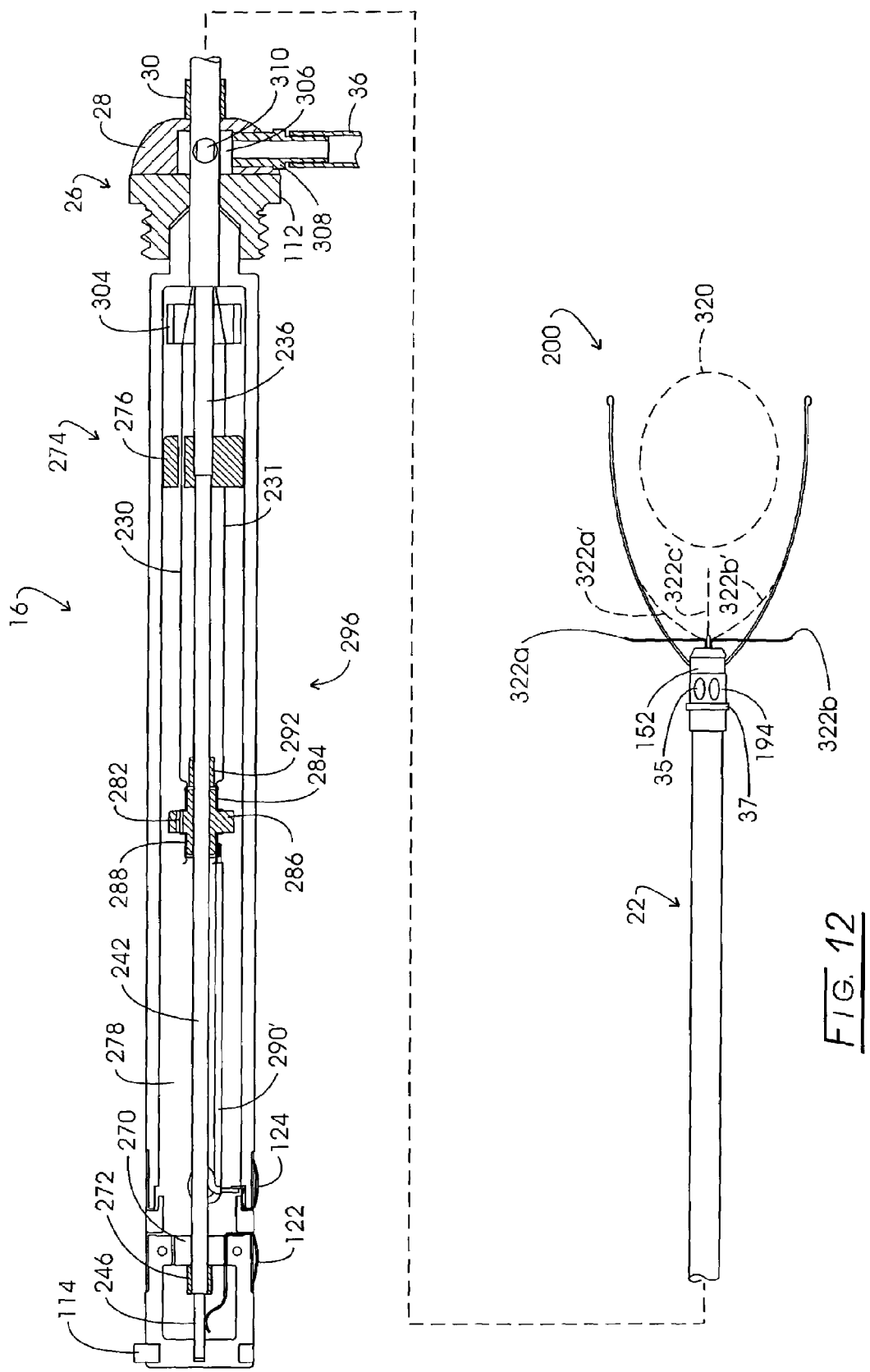
FIG. 12 is a partial sectional view of the instrument shown in FIG. 1 with the capture component leafs schematically depicted at a maximum diametric extent orientation for use with a larger tissue volume sample.
Figure 13:
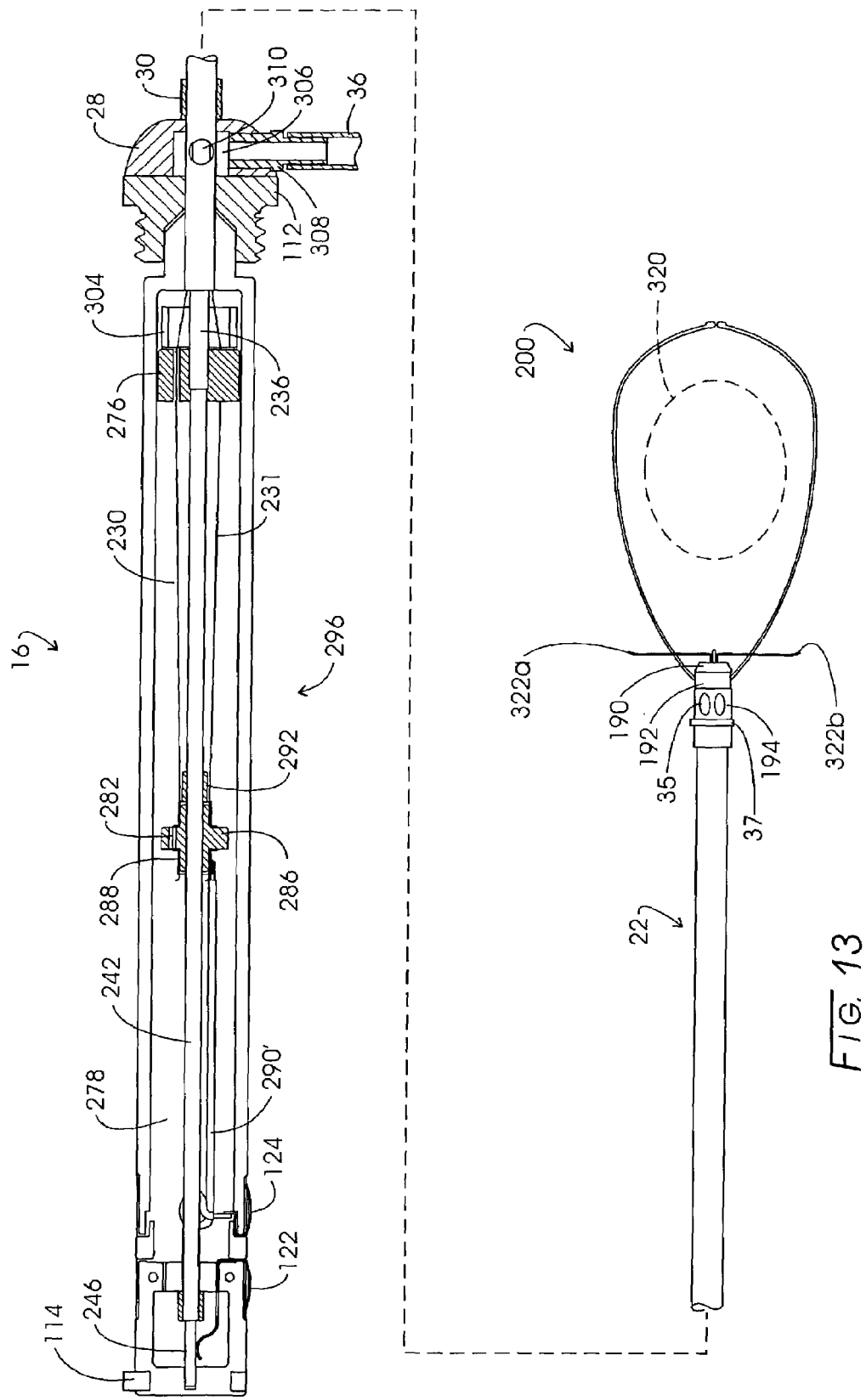
FIG. 13 is a partial sectional view of the instrument of FIG. 12 schematically showing the orientation of capture component leafs in an orientation of full capture.

Referring to FIG. 13, the orientation of the components of reusable component 16 are revealed as the drive component 276 and associated drive tube 236 have been forwardly driven along the support tube 242 into a spaced adjacency with safety stop 304 while the cable terminator 286 has remained in stationary abutting contact with cable stop 292. Accordingly, the symbolically depicted cables 230 and 231 are represented as being taut or under stress induced by the pursing action evoked by drive member 276 subsequent to its orientation as shown in FIG. 12. Note that the tips of the symbolically represented leafs have been drawn together by the pursing action of cables 230–234 and thus, a somewhat hemispheric, dome-like configuration has been evoked having the forward curvature shown. A comparison of this curvature with that represented in FIG. 11 shows them to be similar in terms of degree of curvature, a phenomenon evoked by virtue of utilization of a pursing cable in association with each of the leafs of the capture component. FIG. 13 also reveals that the precursor electrodes as at 322a and 322b have resiliently returned to an orientation normal to the longitudinal axis 24: With this arrangement, the volume of targeted tissue 320 as well as the amount of surrounding healthy tissue may be withdrawn while being protected by the structural integrity now extant at the capture component pursed together leafs. Those leafs are retained in compression by the pursing cables, a state wherein they contribute to the formation of a structurally rigid containment structure cage.

Figure 14:
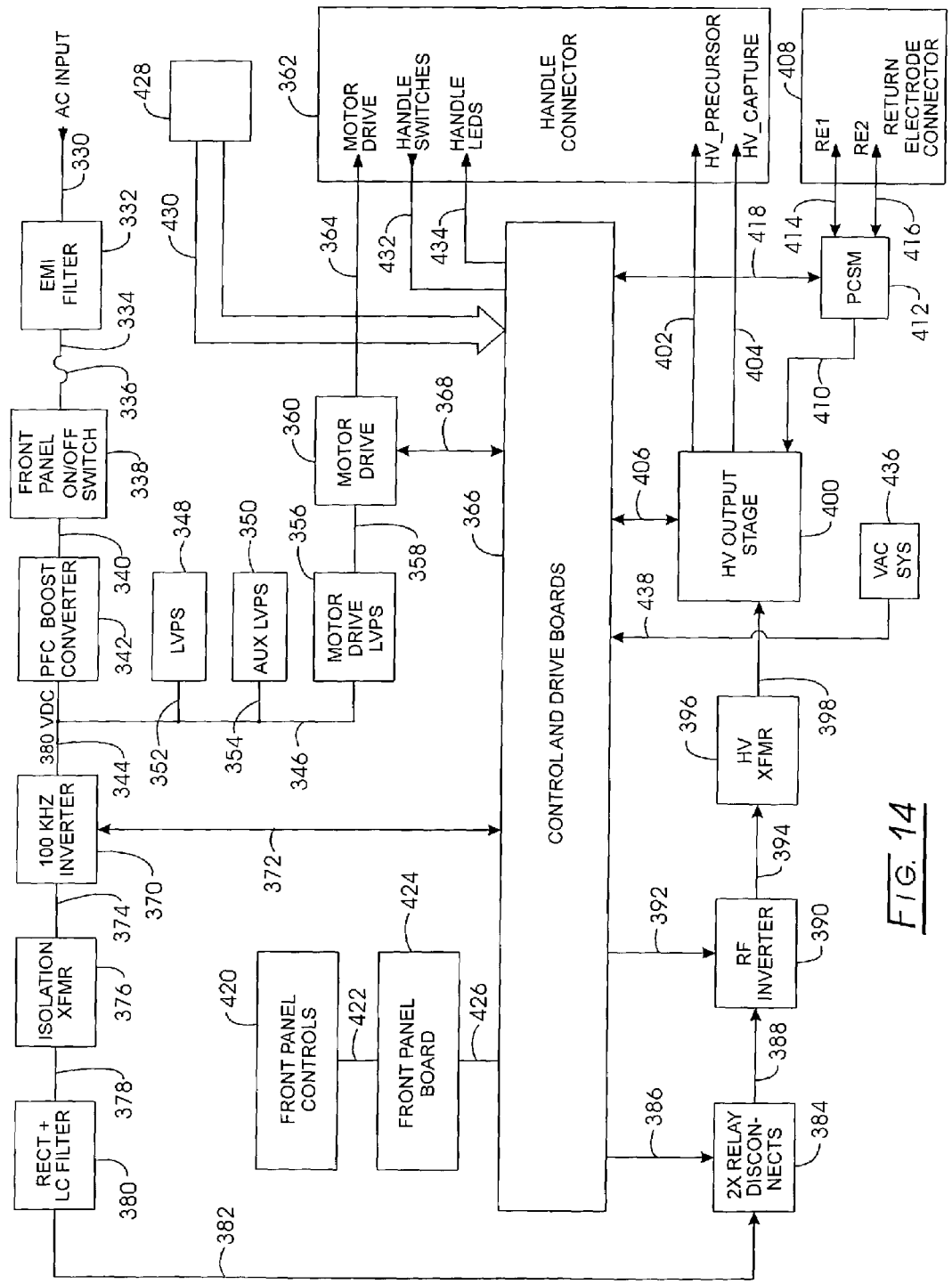
FIG. 14 is a block schematic diagram of the electrosurgical generator and control features employed with the method of the invention.

Referring to FIG. 14, a generalized block diagrammatic representation of the electrosurgical generation features and the control assembly incorporated with console 64 and instrument 12 is presented. In general, the electrosurgical inputs to the pursing cables 230–234 and to the precursor electrodes of the instrument 12 are provided at an operating frequency of about 340 KHz. However, the operating frequency may be selected to be in the range of from about 250 KHz to about 10 MHz. As noted earlier, different capture component maximum diametric values and associated lengthwise capture dimensions are based on the location of the cable stop 292 and a repositioning of the safety stop member 304. With the resulting somewhat universal structuring, motor assembly 160 may provide standardized performance in conjunction with a control which detects forward and rearward stall conditions as well as other load characteristic conditions which will represent fault states. In the figure, a conventional a. c. line input is represented at line 330 extending to an electromagnetic interference (EMI) filter represented at block 332. As represented at line 334 and symbol 336, the filtered output is passed through a fuse and into a front panel power on/off switch function represented at block 338. This switching function is described in connection with FIG. 1 at 82. Switch function 338 passes the filtered input to a power factor correcting (PFC) boost converter as represented at line 340 and block 342. Converter 342 rectifies the a. c. input to it to a d.c. current and boosts the d.c. voltage level to a regulated interim level while also creating a sinusoidal input current waveform which matches the sinusoidal input voltage waveform. This provides for a high power factor to reduce line current harmonics. Converter 342 provides the interim voltage as a 380 volt d.c. bus as represented at lines 344 and 346. The provision of the power factor correction feature at block 342 derives a variety of beneficial attributes. Less current is drawn as compared to conventional electrosurgical generators and the device may be employed universally with power utilities on a worldwide basis. Of additional importance, converter 342 derives a pre-regulated interim voltage at line 344 which permits an optimization of a next following link inverter in the electrosurgical generator function.

Line 346 functions to provide a d.c. input to a primary and auxiliary low voltage power supply (LVPS) as represented respectively at blocks 348 and 350 in connection with respective lines 352 and 354. Redundant low voltage power supplies are employed in view of the criticality of the control system associated with instrument 12. In this regard, failure of a low voltage power supply otherwise occurring without such redundancy could result in shutting down the entire control system at a point in time during critical intervals in the procedure at hand.

The regulated 380 volts d.c. at lines 344 and 346 also is directed to a low voltage power supply represented at block 356 which functions to provide a very specific motor voltage to the motor drive circuitry as represented at line 358 and block 360. Control over the motor voltage, for example, at a level of around 10 volts is important, inasmuch as it is that voltage level which provides the proper rate of forward travel of the leafs and cables of the capture component. In this regard, the deployment of the leafs and electrosurgically excited cable is measured in terms of millimeters per second. Should the drive imparted be too rapid, the excited cables will push against tissue and not cut properly which may result in both unwanted tissue necrosis and false capture stall-based response on the part of the control system. Because the control system operates the motor drive 360 on the basis of detecting, for example, forward stall currents to determine the completion of pursing activity, accommodation is made for anomalies in the motor drive caused by binding phenomena or the like wherein a forward stall would be detected by the control system before the capture component had been properly actuated. Because the rate of advance of the leafs and associated pursing cables is carefully controlled, it is known, for instance, that any excessive motor current detected before a certain initial test interval of time commencing with an initial motor activation would represent a drive malfunction. The same form of a stall-based motor response may occur in the event that the cutting arc is lost in the course of a capture mode of performance. As discussed in detail later herein, the arc may be lost if the resistance "seen" by the electrosurgical generator drops in conjunction with a power-resistance characteristic which cannot accommodate it. Animal tissue encountered in the course of operation of the device may exhibit resistivities having a wide range. Those resistivities or conductivities may have an important impact upon total resistance necessary to maintain a cutting arc. Further, such resistivity or conductivity may be severely influenced by the type of local anesthetic employed by the practitioner. Reusable component 14 connector 68, referred to as a "handle connector" is represented in the instant figure at block 362 which is shown communicating motor drive inputs to the motor assembly 160 as represented by arrow 364 extending from the motor drive function at block 356. Control to the motor drive represented at block 360 initially is provided from a control arrangement which includes control and drive boards as represented at block 366 and dual arrow 368.

Returning to line 344, the regulated 380 volts d.c. output of the converter 342 is introduced to a 100 KHz link inverter represented at block 370 which additionally is shown to be under the control of the control and drive circuit board function of block 366 as represented at dual arrow 372. That control is called upon to effect a constant voltage regulation of the electrosurgical output energy, accommodating the negative dynamic impedance of a cutting arc while achieving an arc-sustaining, non-oscillatory performance. It is at the function represented at block 366 that the requisite power-resistance characteristic of the generator function is established such that, for the range of resistances seen by the generator, sufficient power is provided to sustain or create an arc. On the other hand, the amount of power applied for normal cutting or during a boost interval to create or strike an arc cannot be excessive to the extent that the retrieved tissue specimen is damaged by arc occasioned necrosis. The a.c. (square waveform) output of link inverter 370 is presented, as represented at line 374 to one side of an isolation transformer represented at block 376. Transformer 376 provides an output, as represented at line 378 which is rectified and filtered as represented at block 380 to develop a regulated d.c. link voltage at line 382 having a value of about 100 volts. The amplitude of the link voltage at line 382 is controlled with a circuit topology incorporating a high gain or rapidly responsive internal feedback loop in conjunction with a relatively low gain or slow external feedback loop and functions to establish a constant voltage amplitude of the operating output of a system having active electrodes of varying geometry. That system further operates within tissue exhibiting a relatively wide potential range of conductivity or resistivity which will be seen to be markedly influenced by the conductivity or resistivity of an infiltrated local anesthetic. Line 382 is directed to two relay disconnects as represented at block 384. These relay disconnects are controlled from the control and drive circuit board function represented at block 366 as indicated by arrow 386. The d.c. link voltage then, as represented at line 388 is directed to an RF resonant inverter as represented at block 390. Inverter 390 operates in controlled relationship with the control and drive circuit boards represented at block 366 as indicated by arrow 392. It may be noted that by positioning the relay disconnects 384 before the RF inverter 390, in the case of a fault or other anomaly, input to the RF inverter 390 itself can be disconnected. Inverter 390 is of a conventional resonant tank circuit variety which is tuned to a particular frequency. Its output peak-to-peak voltage amplitude is controlled by the amplitude of the d.c. link voltage. Thus, the output voltage amplitude for a negative dynamic impedance arc drive is made constant for boost and normal cutting performance as is its frequency.

The output of inverter 390 is directed, as represented by arrow 394 and block 396 to one side of a high voltage transformer which steps its amplitude up to from about 800 to about 1000 volts peak-to-peak (normal cutting) from the 100 volt d.c. link voltage level. This output of the transformer stage 396 at arrow 398 is an electrosurgical cutting output which is, in effect, steered by series relays at a high voltage output stage represented at block 400 to either the precursor electrode input as represented at arrow 402 or to the capture component cables as represented at arrow 404. Control over the output stage 400 is indicated by dual arrow 406. The relay function associated with this stage 400 will be seen to create a slight delay from the initiation of a boost level control signal to the commencement of the ramping of peak-to-peak voltage up to a boost voltage level or plateau. Connector 80 of console 64 which is electrically associated with the dispersive electrode 70 is represented at block 408. The connector, in addition to providing a return to the high voltage output stage 400 as represented at arrow 410, is coupled with a patient circuit safety monitor (PCSM) which is represented at block 412. Monitor circuit 412 is coupled with each of the discrete electrodes 72 and 74 as represented at dual arrows 414 and 416 and is controlled to provide fault data to the control and drive boards at block 366 as represented by dual arrow 418. As discussed in connection with return electrode 70 as shown in FIG. 1, the present system operates in monopolar fashion and utilizes a dual component dispersive pad as a return electrode. The RE1 and RE2 leads represented at respective lines 414 and 416, in addition to providing a high voltage return, are utilized to output a high frequency current which is directed from one pad as at 72 to the other as at 74 to verify the tissue resistance between them. In this regard, the PCSM circuit 412 will apply about a 10 volt signal at 50 KHz to the two return electrode pads and verify proper resistance. Only upon such verification will the system permit the practitioner to continue the procedure by going into a ready mode. If the PCSM test is not met or passed, the system will not proceed and both visible and audible pulsed alarms are produced. PCSM circuit 412 also performs a self test at such time as the on/off switch represented at block 338 is actuated to an on state.

The front panel controls as described at console 64 in connection with FIG. 1 are represented at block 420. These controls, as represented at line 422 and block 424 are associated with a front panel circuit board which, in turn, as represented at line 426 is provided inputs and outputs from the control and drive boards represented at block 366. Both control and drive boards, additionally receive inputs from foot switch 88 as represented at block 428 and switching line bus arrow 430. Inputs from switches 56–58 at reusable component 14 are represented at arrow 432, while outputs to the LED arrays as at 60 are represented at arrow 434. Finally, as discussed in connection with FIG. 1, a vacuum switch may be incorporated within the tubing or conduit of the evacuation system providing a requirement in electronic logic that the vacuum system be turned on before commencing a procedure, a requirement somewhat similar to the PCSM test requirement. Such a vacuum switch is represented at block 436 and its association with the control is represented at arrow 438.

With the circuit arrangement thus described, a primary circuit is developed between the a.c. input at line 330 and the isolation transformer 376. From the output of isolation transformer 376, providing the noted d.c. link voltage, a secondary, lower voltage circuit is evolved. That secondary circuit extends to the high voltage transformer represented at block 396. From that circuit location, a high voltage circuit obtains with the system which develops the noted electrosurgical cutting signal. These three different regions are incorporated in console 64 with different isolation barriers of the system. In this regard, some components fall within a safety extra low voltage circuit regime (SELV) while other circuits are completely isolated from potential contact. For medical devices which are going to be attached to a patient, concerns become more stringent for assuring that no current will flow from one device, for example, to another associated with the patient. A more detailed description of the electrosurgical generator and associated control is provided in the above-identified application for United States Patent by Eggers, et al., Ser. No. 09/904,412, now U.S. Pat. No. 6,471,659, issued Oct. 29, 2002, which is incorporated herein by reference. A more detailed description of the instrument 12 is provided in the above-identified application for U.S. Pat. Ser. No. 09/904,396 by Eggers, et al., which is incorporated herein by reference.

Animal and field studies have been conducted with and concerning electrosurgical system 10. As noted above, the electrosurgical generator component of the system is called upon to accommodate not only resistance variation occasioned by the dynamic performance of the pursing cables during a capture maneuver, but also must accommodate the resistance characteristics of tissue and fluids encountered in the course of capture procedure. For example, substantial variations of electrical resistivity, or inversely, conductivity will be encountered where the system is employed for breast biopsy. Looking momentarily to FIG. 15, these substantial variations are portrayed graphically. Note that normal breast tissue exhibits a resistivity extending from about 350 ohm-cm to about 2000 ohm-cm. By contrast, the resistivity of malignant breast tissue extends from about 150 ohm-cm to about 300 ohm-cm. In further contrast, "fatty" tissue is at the upper end of the physiological resistivity range extending from about 1600 ohm-cm to 2000 ohm-cm and muscle tissue exhibits low resistivity similar to malignant breast tissue. Blood encountered in the course of the procedures is at the very lowest end of the resistivity range extending from about 150 ohm-cm to about 200 ohm-cm depending upon hematocrit. Accordingly, during the capture mode performance of system 10 the electrosurgical generator will, from patient to patient, confront what may be deemed a wide variation in resistance. In this regard, the range of resistance, not including that at the arc may extend from about 1500 ohms to about 2000 ohms. At the opposite end of this range, very dense tissue may reach as low as 150 ohms or less. Thus, in view of this range of resistances the electrosurgical system is called upon to perform in conjunction with a resistance-power characteristic which assures the creation and maintenance of a cutting arc over the extended resistance range. However, for each resistance encountered by the system the amount of power evoked cannot be too high. Where the power is excessive, thermal artifacts will be witnessed at the biopsy sample to an extent which well may be deemed unacceptable.

Over the course of testing the system 10 in conjunction with a 10 mm maximum capture diametric extent a variety of resistance-power characteristics were evolved and evaluated. Looking to FIG. 16, an initial resistance-power characteristic tested is plotted at curve or profile 450. Characteristic 450 exhibits excessive power at lower resistance load values and, correspondingly, too low a power output at higher resistance load values. Characteristic 450 is identified as a "pre-april" characteristic in associated data. In the latter regard, looking momentarily to Table 1, characteristic 450 is tabulated at column 5. A next characteristic is shown at curve 452. Curve 452 shows an improvement in power output at higher resistance values. However, at the low end of this resistance range, for example, starting at about 500 ohms the RF power output commences to drop and drop significantly at resistances below about 300 ohms. It was observed that at about a 150 ohm value of resistance the power became so low that the system was unable to sustain a cutting arc. Characteristic 452 is tabulated at column 6 of Table 1. Resistance-power characteristic curve 454 is coincident with curve 452 at higher resistance levels and, it may be observed that at lower resistance levels, higher power values are maintained, not falling below 180 watts. Curve 454 is tabulated at column 7 of Table 1. Resistance-power characteristic curve 456 is seen to be coincident with curve 452 at higher ranges of resistance and falls somewhat between curves 452 and 454 at lower resistance values. It may be noted that the curve power output falls to 100 watts at the low 100 ohm resistance value. Curve 456 is tabulated at column 9 of Table 1.

Figure 17:
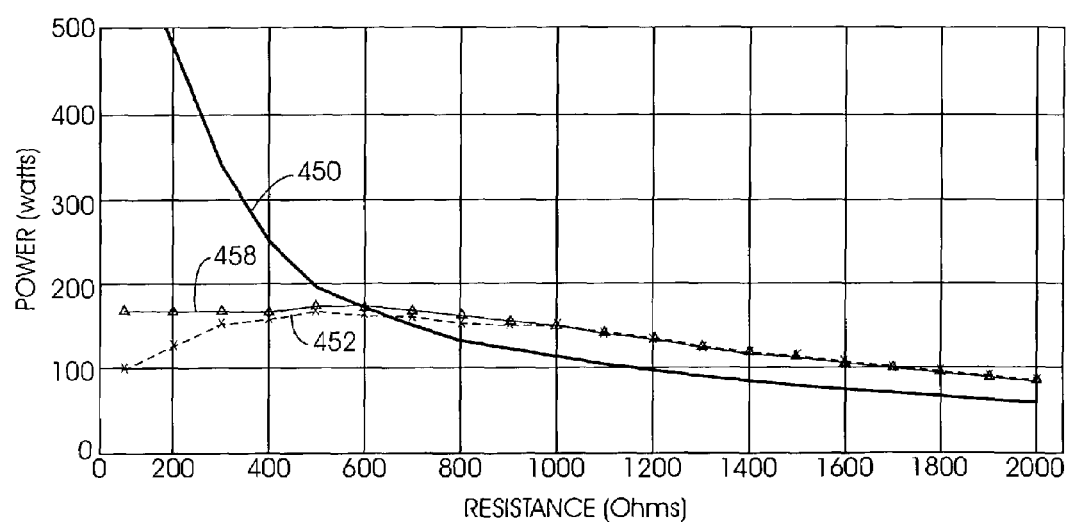
FIG. 17 is another graph displaying power verses resistance profiles for electrosurgical generators employed with the method of the invention and showing a preferred profile.

Referring to FIG. 17, characteristic curves 450 and 452 are reproduced in combination with a resistance-power characteristic curve 458. Note that curve 458 is essentially coincident with curve 452 at the higher ranges of resistance, such coincidence in those ranges representing an acceptable profile with sufficient power to create an arc and maintain an arc but not with excessive power. At lower ranges of resistance it may be observed that the curve remains at a power level above a value of about 170 watts, again a sufficient but not a excessive power level. Curve 458 is tabulated at column 12 in Table 1.

TABLE 1

| 1 Load (Ohms) | 2 Newer Voltage (Vpp) (Vref 3.23) | 3 Apr. 18, 2002 Voltage (V rms) (Vref 3.23) | 4 May 19, 2002 Current (A rms) E&A Jun. 11, 2002 | 5 Pre April Power (watts) | 6 Apr. 18, 2002 Power (watts) | 7 May 19, 2002 Power (watts) E&A Jun. 11, 2002 |
|---|---|---|---|---|---|---|
| 100 | 300 | 100 | 1.34 | 600 | 100.0 | 180 |
| 200 | 488 | 160 | 1.08 | 481 | 128.0 | 231 |
| 300 | 640 | 215 | 0.91 | 341 | 154.1 | 248 |

TABLE 1-continued

| 400 | 750 | 252 | 0.79 | 251 | 158.8 | 248 |
| 500 | 860 | 290 | 0.66 | 196 | 168.2 | 220 |
| 600 | 940 | 315 | 0.58 | 172 | 165.4 | 203 |
| 700 | 1010 | 338 | 0.51 | 151 | 163.2 | 185 |
| 800 | 1060 | 353 | 0.46 | 133 | 156.1 | 171 |
| 900 | 1100 | 368 | 0.42 | 124 | 150.5 | 160 |
| 1000 | 1150 | 384 | 0.39 | 115 | 147.5 | 151 |
| 1100 | 1160 | 390 | 0.36 | 105 | 138.3 | 143 |
| 1200 | 1180 | 401 | 0.34 | 97 | 134.0 | 136 |
| 1300 | 1200 | 412 | 0.31 | 91 | 130.6 | 127 |
| 1400 | 1215 | 410 | 0.29 | 85 | 120.1 | 119 |
| 1500 | 1230 | 412 | 0.28 | 80 | 113.2 | 114 |
| 1600 | 1232 | 413 | 0.26 | 75 | 106.6 | 108 |
| 1700 | 1236 | 414 | 0.24 | 71 | 100.8 | 102 |
| 1800 | 1238 | 413 | 0.23 | 67 | 94.6 | 97 |
| 1900 | 1239 | 413 | 0.22 | 63 | 89.8 | 92 |

| 8 May 21, 2002 Rev.A Actual Voltage* (V rms) E&A | 9 May 21, 2002-Rev.A Actual Power* (watts) E&A | 10 May 21, 2002 Voltage (V rms) Plexus | 11 May 19, 2002 Voltage (V rms) E&A Jun. 11, 2002 | 12 April, 2002 Constant Power Power (watts) New Version |
|---|---|---|---|---|
| 100 | 100.0 | 100 | 134 | 169.0 |
| 188 | 176.7 | 196 | 215 | 167.4 |
| 242 | 195.2 | 250 | 273 | 167.3 |
| 281 | 197.4 | 288 | 315 | 167.7 |
| 309 | 191.0 | 316 | 332 | 175.2 |
| 331 | 182.6 | 332 | 349 | 175.0 |
| 343 | 168.1 | 344 | 360 | 168.1 |
| 357 | 159.3 | 356 | 370 | 159.3 |
| 367 | 149.7 | 368 | 380 | 149.7 |
| 384 | 147.5 | 380 | 389 | 147.5 |
| 390 | 138.3 | 385 | 396 | 138.3 |
| 401 | 134.0 | 385 | 404 | 134.0 |
| 412 | 130.6 | 385 | 406.5 | 130.6 |
| 410 | 120.1 | 385 | 409 | 120.1 |
| 412 | 113.2 | 385 | 413.5 | 113.2 |
| 413 | 106.6 | 385 | 415 | 106.6 |
| 414 | 100.8 | 385 | 416 | 100.8 |
| 413 | 94.8 | 385 | 417 | 94.8 |
| 413 | 89.8 | 385 | 418 | 89.8 |

A next aspect of cutting arc maintenance has been discovered to be associated with the local anesthetic utilized with the procedure. While a variety of anesthetic agents have been utilized, the more commonly used anesthetic drug is the above-discussed lidocaine which is injected intramuscularly to effect a nerve block or field block using concentrations typically in the range of 0.4% to 2.0% (weight percent). The diluent currently used for intramuscular injections of local anesthetics is isotonic saline which contains 0.9% sodium chloride. Isotonic saline is used as the diluent due to the fact that its osmolarity at normal body temperature (37° C.) is 286 milliOsmolds/liter which is close to that of cellular fluids and plasma, the latter having an osmolarity of 310 milliOsmolds/liter. It is generally accepted that diluents having an osmolarity in the range of from about 240 to about 340 milliOsmolds/liter are isotonic solutions and therefore can be safely injected intramuscularly.

Returning momentarily to FIG. 15, it may be observed that the electrical resistivity of isotonic saline is 50 to 60 ohm-cm which is much lower than the bulk tissue resistivity properties of human breast tissue. As a consequence, when isotonic saline is injected intramuscularly into tissue in the course of local anesthetic administration (e.g., 1% lidocaine in 0.9% NaCl in water as the diluent), the electrical conductance of the infused tissue increases significantly. Conversely, as the isotonic saline diluents are injected intramuscularly, the tissue electrical resistance decreases significantly. With respect to the resistivity values given above, the electrical conductivity of isotonic saline is 17 milliSiemens/cm; the bulk tissue property conductivities of human tissue are about 1 to 5 milliSiemens/cm depending upon fat content and the conductivity of blood is approximately 7 milliSiemens/cm depending upon hematocrit.

Animal studies and field trials have determined that when saline is employed as the diluent of a local anesthetic its low resistivity will, in many cases, cause a drop in resistance witnessed by electrosurgical generators, for instance, driving the observed resistance down to 100 ohms and less. As this occurs, there is a drop off in power as well as voltage to an extent that an arc cannot be created or sustained. While normally, the peak-to-peak voltage creating and sustaining an arc will range generally from 600 volts to 700 volts, under the influence of the saline diluent, that potential difference may drop substantially, again rendering the system incapable of establishing or sustaining a cutting arc.

Figure 18:
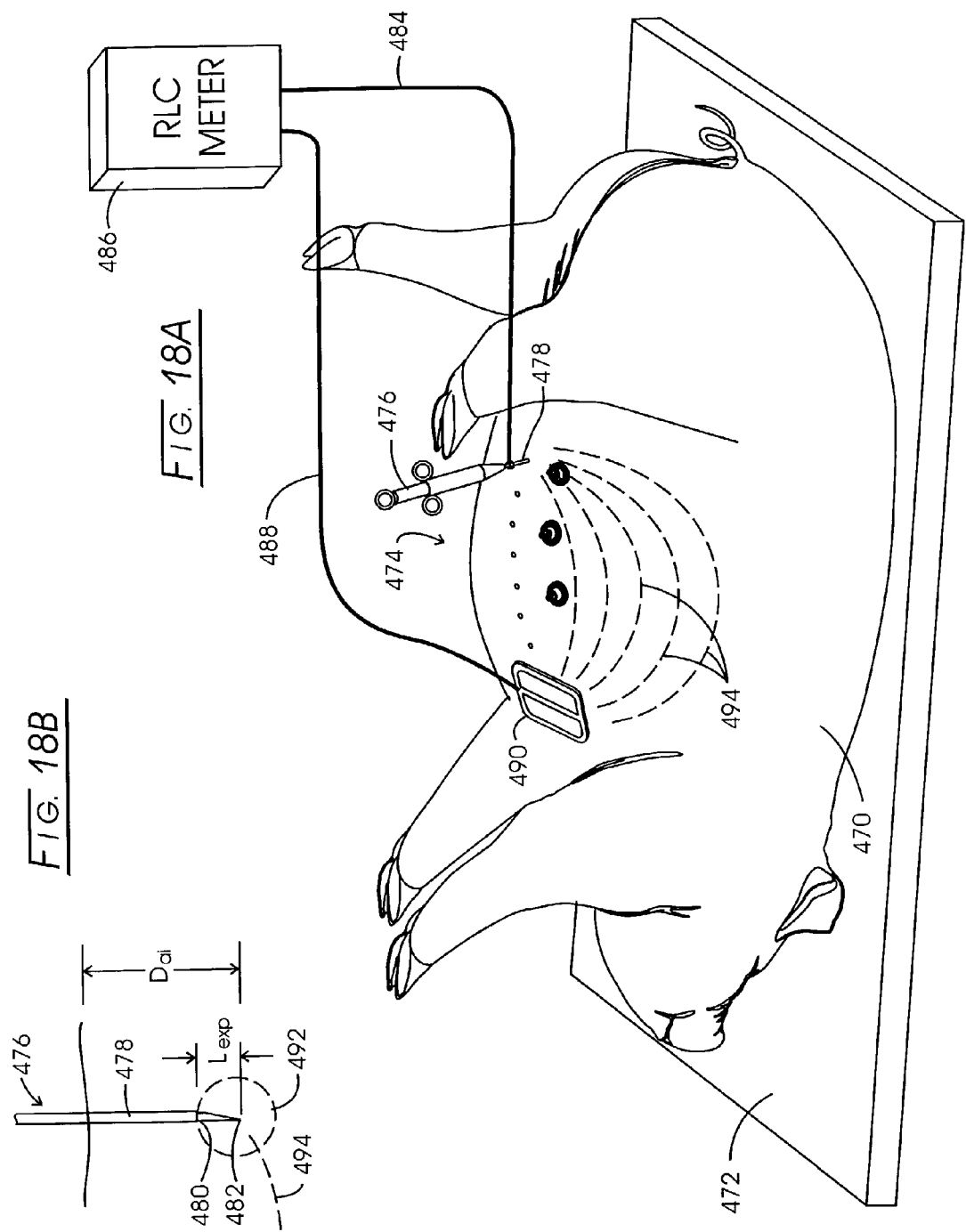
FIG. 18A is schematic representation illustrating animal studies undertaken in conjunction with the method of the invention.
FIG. 18B is a schematic representation of a resistance measuring needle employed with the studies represented at FIG. 18A.

Referring to FIG. 18A, the laboratory setup for carrying out the noted animal studies is stylistically portrayed. In the figure, a fully anesthetized female pig is shown positioned upon its back which, in turn, is supported upon a platform 472. The figure schematically illustrates the first component of a two aspect form of experiment wherein as an initial procedure, resistance values were measured for a number of locations at the breast region 474. Those locations were numbered and marked. A syringe having a resistance measuring needle was prepared, as represented in general at 476. The upper portion of the needle as represented at 478 was covered with an electrically insulative cannula. Looking to FIG. 18B, the needle 478 is shown covered with an electrically insulative sleeve or cannula formed of shrink wrap which terminates at edge 480. Disposed outwardly from the edge 480 of the cannula is a length, $L_{exp}$ of exposed stainless steel extending to the tip 482 of the needle. The exposed needle electrode length, $L_{exp}$ was generally in a range of about 1.5 to 2.5 millimeters in extent. As depicted in FIG. 18A, the electrode needle 478 was electrically coupled as represented at lead 484 to one input of a Fluke 6306 RLC (resistance, inductance, capacitance) meter represented at block 486. This RLC meter was selected inasmuch as tissue exhibits a frequency dependent resistance. Accordingly, the frequency of the measurements taken was at 340 kHz. The second terminal of RLC meter 486 was connected as represented at lead 488 to a dispersive return electrode 490. Needle 478 was injected to a depth, $D_{ai}$ of about 1.5 cm to 2.0 cm whereupon initial resistance measurements were made followed by an injection of a bolus of either an isotonic saline-based local anesthetic solution or an isotonic solution exhibiting much higher resistivity or conversely, much lower conductivity, for example, a 5% dextrose diluent with or without anesthetic agent. In general, the saline diluent was combined with 1% lidocaine with or without epinephrine and the dextrose diluent solution was combined with or without 0.8% lidocaine. The latter is referred to as "D5W based lidocaine". For the instant methodology, it should be observed that when a small electrode as represented at electrode needle 476 is employed within relatively larger medium coupled, in turn, with a large dispersive electrode as at 490, the resistance will in effect be measured within a quite limited region extending from that electrode. Shown in FIG. 18B, the zone of resistance being measured as represented in general at 492 will be quite small or localized to the extent of involving only a few millimeters. From the electrode position, the current flux lines and voltage gradients disperse rapidly in inverse square fashion toward the return electrode 490. Such dispersive lines are represented, for example, at 494. Accordingly, the electrodes employed with instrument 12 will confront resistances which may vary considerably with very small extents of movement about and around a targeted tissue volume. Thus, extensive regions of the resistance-power characteristics discussed above may be encountered by an associated electrosurgical generator. Using a Fisher Scientific Digital Conductivity Meter (model No. 09-326-2), conductivity measurements of certain of the employed solutions were made. For example, a 5% dextrose with 0.8% lidocaine solution was measured to have a conductivity of 2.07 milliSiemens/cm at 25° C. Correspondingly, an isotonic saline solution was measured to have a conductivity at 24.1° C. of 14.0 milliSiemens/cm. Returning momentarily to FIG. 15, it may be observed that the resistivity of the saline-based local anesthetic is illustrated as extending from about 50 ohm-cm to about 75 ohm-cm, while the corresponding resitivity of dextrose-based local anesthetic extends from about 500 ohm-cm to about 550 ohm-cm.

As the second aspect of animal (pig) studies which were undertaken, system 10 was employed in conjunction with select local anesthetic agent diluents to retrieve and evaluate tissue specimens. The earlier experiments carried out are summarized in Appendices A and B.

Figure 19:
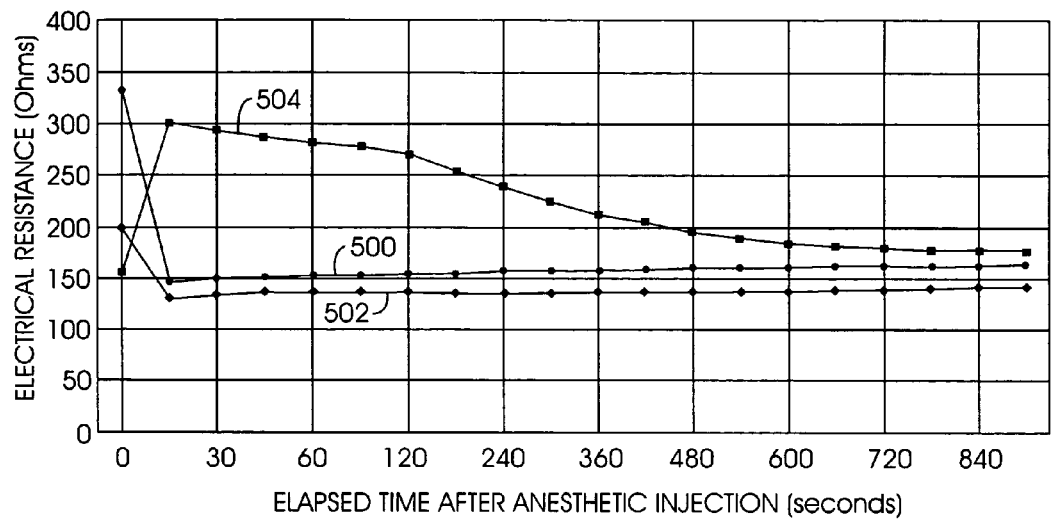
FIG. 19 is a graph plotting electrical resistance verses elapsed time following anesthetic injection with respect to animal studies carried out in connection with the method of the invention.

Turning to FIG. 19, a graphic representation of certain of the resistance measuring results obtained in conjunction with animal studies carried out as described in connection with FIGS. 18A–18B is revealed. In the figure, a curve 500 represents a test carried out in conjunction with injection of a 3 cc bolus of a local anesthetic comprised of a solution of 1% lidocaine with epinephrine in a ratio of 1:200,000 in a normal or isotonic saline diluent. Before injection of the bolus, resistance over the bolus was 332 ohms. Shortly after injection of the bolus, resistance dropped to 146 ohms and thereafter hovered around 150 to 160 ohms, where it remained for over twelve minutes. In a typical use of system 10, one to six injections of 3 cc to 10 cc each for a total of 25 cc to 30 cc of local anesthetic are made along a somewhat circular locus to effect a field block in close proximity (within 1 cm to 2 cm) to the operative site. Data represented by curve 500 is tabulated at experiment 3 in Appendix A.

Curve 502 plots the results of carrying out a resistance investigation wherein a 10 cc injection of a 1% solution of lidocaine in a normal (isotonic) saline diluent was utilized. The initial resistance measurement prior to the injection of the local anesthetic bolus shows a value of about 200 ohms. Within about 15 seconds from the injection of the bolus of normal saline-based local anesthetic, resistance decreased as low as about 130 ohms and thereupon hovered between about 130 ohms and about 144 ohms.

In contrast, where the injection and resistance measurements involved a local anesthetic agent with one of the preferred diluents of the present invention (vis., 5% Dextrose in water with 0.8% lidocaine), the initial tissue resistance as seen at curve 504 was about 160 ohms. Shortly following the injection of the bolus of this preferred diluent-based local anesthetic, resistance was observed to increase to nearly 300 ohms. The measured resistance values remained above about 280 ohms after two minutes which is the typical waiting period for the start of a subsequent surgical procedure. As may be evidenced from curve 504, this is a highly desirable resistance enhancing characteristic. As represented at experiments 3 through 7 of Appendix A tests were carried out to provide resistance measurement data for locations both over the injected bolus as well as at locations spaced from the over bolus location.

Experimentation also has been carried out with the electrosurgical system 10 to evaluate the capture performance of the system in conjunction with a local anesthetic solution incorporating a saline-based diluent.

Fourteen animal (pig) experiments are described in conjunction with Appendix B wherein a local anesthetic having a solution incorporating a saline-based diluent was tested in conjunction with an instrument 12 configured for a 10 mm maximum diameter capture configuration. The electrosurgical generators employed a resistance-power characteristic corresponding with curve 456 in FIG. 16. Those experiments indicate that there are occasions when the cutting arc cannot be sustained when saline-based lidocaine is used for infiltration anesthesia and no tissue sample is obtained. In general, capture failure is considered to include no sample or a very small sample or sample which is obtained in small pieces indicating mechanical rather than electrosurgical cutting.

A sequence of animal (pig) experiments utilizing system 10 were carried out on May 22, 2002 with purpose of evaluating operation of that system in conjunction with a saline-based local anesthetic and a dextrose-based local anesthetic. The May study, performed at The Ohio State University Medical Center, was carried out utilizing two consoles as described at 64 in conjunction with FIG. 1.

Figure 15:
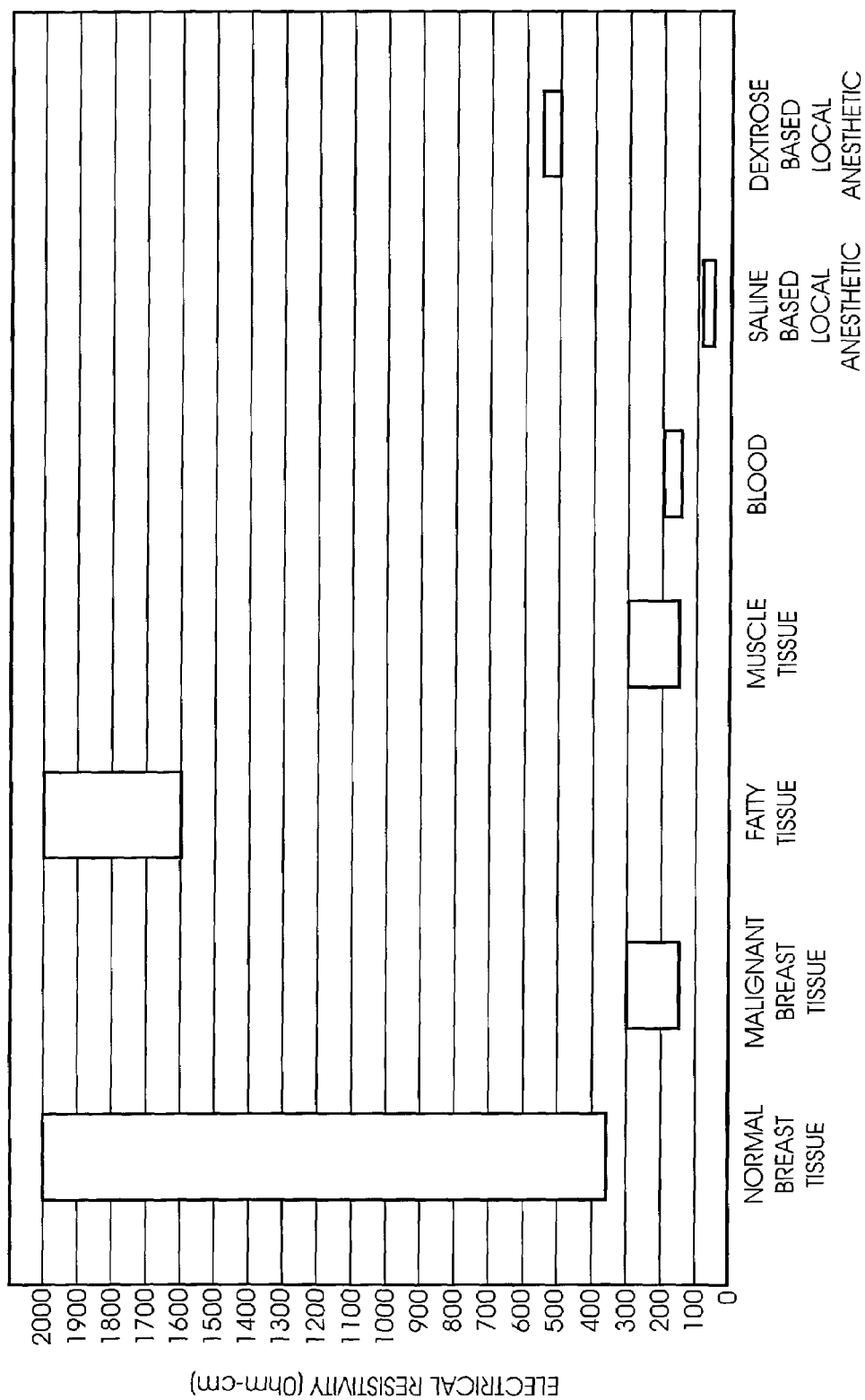
FIG. 15 is a chart plotting the range of electrical resistivities in ohm-centimeters for identified human tissues and blood as well as for saline-based local anesthetic and dextrose-based local anesthetic.
Figure 16:
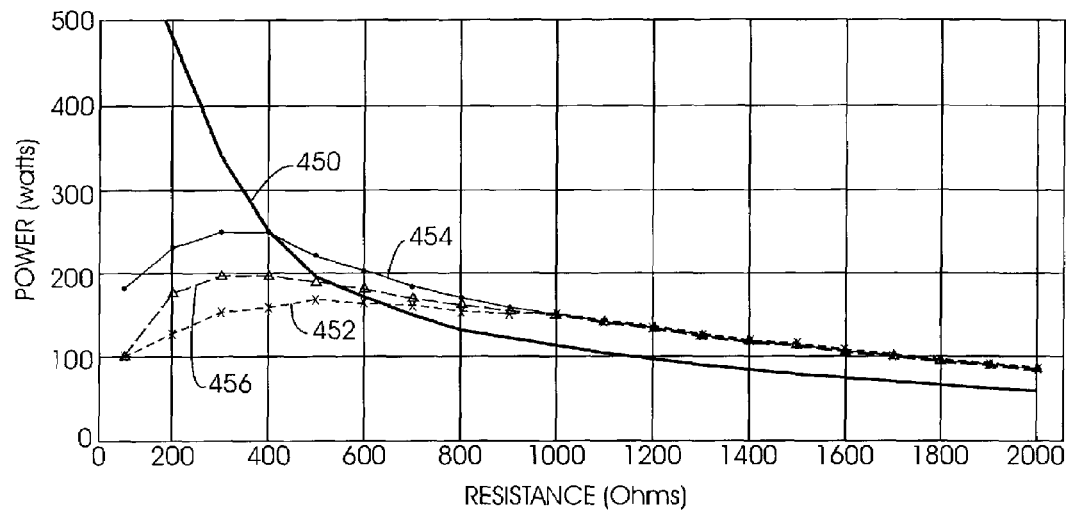
FIG. 16 is a graph showing power verses resistance profiles for electrosurgical generators employed with the method of the invention.

Looking additionally to Table 2, these consoles were identified as a "Model 3000 Controller" as described above, controller serial number 89140 of a series identified as A1708 utilized a drive board version (FIG. 15, block 366) having a resistance-power characteristic corresponding with curve 452 illustrated in FIGS. 16 and 17. A second controller identified as having serial number 89146, again identified as being of an A1708 series was configured having a drive board with a resistance-power profile or characteristic corresponding with curve 454 illustrated in conjunction with FIG. 16. A profile represented by the latter curve 454 provided 40% more power at a 200 ohm load and 26% more power at a 300 ohm load but was similar at resistances above 700 ohms to the curve 452 profile. For these tests, two types of local anesthetic were employed, viz., conventional isotonic saline-based 1% Lidocaine with epinephrine at a ratio of 1:200,000 and D5W based lidocaine which was provided as a solution incorporating 0.8% lidocaine with a diluent of 5% dextrose in water in combination with epinephrine in a ratio of 1:200,000. The test included both resistance measurements after injection of local anesthetic and system 10 tissue capture using the two versions of the drive boards as set forth above. Initial resistance measurements were performed as described in conjunction with FIGS. 18A and 18B with the needle exposure, $L_{exp}$ being 5 mm. This needle was positioned in the center of the region to be captured and resistance was measured with a Fluke 6306 RLC meter as at 486 set at a frequency of 340 kHz corresponding with the frequency of system 10. RF voltage, current and resistance was measured for each capture using a Techtronics digital storage oscilloscope. From these measurements, power and resistance (average and maximum) could be derived. Power demand by the model 3000 controller was also measured using a fast-response wattmeter marketed by Voltech, Inc.

The anesthetic protocol set forth in Table 2 represents a sequence code, the first digit of which represents the number of injections of local anesthetic. The second digit represents the volume of local anesthetic bolus injected in cubic centimeters. The third digit represents a radial distance in centimeters from the center line of the target tissue, and the fourth digit represents the amount of time in minutes ensuing or waiting before the capture procedure was started. These values are listed in the fourth rightward column of Table 2 headed "Anesthetic Protocol".

Table 2 compiles the results of the testing undertaken with respect to twenty-seven trials utilizing 27 disposable components, 16 or "probes" provided from lot 511042, manufactured by Medsource Technologies, Inc. of Newton, Mass. One of these components 16 was reused in conjunction with an instrument 14 in a manner wherein the capture cables were cut, thus preventing power from being applied to the pursing cables during deployment and the tissue capturing phase of performance. As before, a capture failure was considered to occur when no sample or a very small sample or a sample with small pieces was recovered indicating mechanical rather than electrosurgical cutting.

The data tabulated in Table 2 reveals that tissue capture failures occurred in a total of 4 out of 17 (24%) capture trials when saline-based local anesthetic was used. It is likely that the number of failures would have been even larger except for the fact that the particular pig utilized in the experimentation had an unusually heavy fat layer throughout the possible tissue capture sites, resulting in higher than normal tissue resistance levels. Recall the graphics of FIG. 15 illustrating the electrical resistivity of fatty tissue. Notwithstanding, the presence of this fatty tissue in the subject animal, some regions of it were located in which the tissue resistance was in the 200 ohm to 300 ohm range during capture when a saline-based local anesthetic was used prior to capture.

There were no tissue capture failures (10 out of 10 successes) when the 5% dextrose-based diluent local anesthetic was used following essentially the same anesthetic protocols as employed with the saline-based local anesthetic.

One of the provided 27 disposable components 16 or probes was utilized to attempt to capture the fatty tissue (typically encountered in the subject animal of Table 2) without any cutting arc (by removing the cut/capture electrode from the probe). The result of this capture procedure was a failure to capture with the capture component as at 200 fully deployed and forming a "tulip" shape with the leafs of that component otherwise being undeformed. If this attempt were made in highly dense or fibrous tissue, the reusable component would have either stalled before complete forward deployment of the leafs or the leaf members would have been significantly deformed.

TABLE 2

| Model 3000 Controller Serial Number (Type) | Power And Voltage Profile | Anesthetic | Anesthetic Protocol | Number Of Locations For Injection | Amount Injected Per Location (Cc) | Radial Distance From Center Line Of Lesion (Centimeters) | Waiting Time (Minutes) | Number Of Capture Trials | Number Of Capture Failures |
|---|---|---|---|---|---|---|---|---|---|
| 89140 (A1708) (Console 64) | 452 | Saline based 1% Lidocaine with 1:200,000 Epinephrine | 4 × 4 × 1 × 5 | 4 | 4 | 1 | 5 | 2 | 0 (0%) |
| | | | 4 × 4 × 1 × 1 | 4 | 4 | 1 | 1 | 4 | 1 (25%) |
| | | | 1 × 10 × 0 × 1 | 1 | 10 | 0 | 1 | 3 | 1 (33%) |
| | | | 6 × 5 × 1 × 2 | 6 | 5 | 1 | 2 | 1 | 1 (100%) |
| | | | 6 × 5 × 1 × 6 | 6 | 5 | 1 | 6 | 1 | 0 (0%) |
| | | 5% Destrose based 0.8% Lidocaine with 1:200,000 Epinephrine | 4 × 4 × 1 × 5 | 4 | 4 | 1 | 5 | 2 | 0 (0%) |
| | | | 4 × 4 × 1 × 1 | 4 | 4 | 1 | 1 | 3 | 0 (0%) |
| | | | 1 × 10 × 0 × 1 | 1 | 10 | 0 | 1 | 3 | 0 (0%) |
| | | | 6 × 5 × 1 × 2 | 6 | 5 | 1 | 2 | 1 | 0 (0%) |

TABLE 2-continued

| Model 3000 Controller Serial Number (Type) | Power And Voltage Profile | Anesthetic | Anesthetic Protocol | Number Of Locations For Injection | Amount Injected Per Location (Cc) | Radial Distance From Center Line Of Lesion (Centimeters) | Waiting Time (Minutes) | Number Of Capture Trials | Number Of Capture Failures |
|---|---|---|---|---|---|---|---|---|---|
| 89144 (A1708) (Console 64) | 454 | Saline based 1% Lidocaine with 1:200,000 Epinephrine | 4 × 4 × 1 × 1 | 4 | 4 | 1 | 1 | 3 | 1 (33%) |
| | | | 1 × 10 × 0 × 1 | 1 | 10 | 0 | 1 | 2 | 0 (0%) |
| | | | 6 × 5 × 1 × 2 | 6 | 5 | 1 | 2 | 1 | 0 (0%) |
| | | 5% Destrose based 0.8% Lidocaine with 1:200,000 Epinephrine | 4 × 4 × 1 × 1 | 4 | 4 | 1 | 1 | 1 | 0 (0%) |
| | | | | | | | Total= | 27 | |

As the instant investigation involving animal studies and trials progressed, inquiry as to the arc quenching phenomenon at the capture electrodes turned to the anatomical aspects of the environment of capture as an adjunct aspect of the low resistances encountered in the presence of a local anesthetic agent in combination with a saline-based diluent. The female breast represents a predominating anatomical region involved with the system and method at hand. Accordingly, its anatomical structuring was considered in conjunction with associated breast phantom experimentation.

Figure 20:
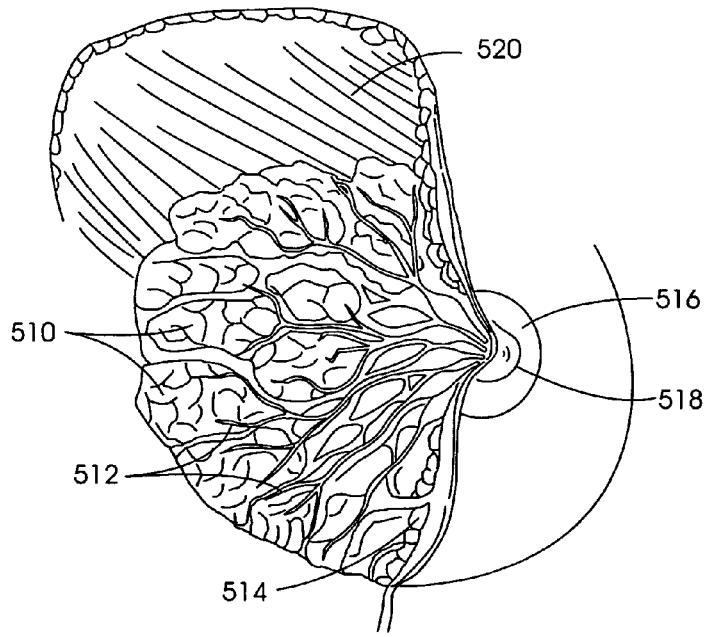
FIG. 20 is an anatomical representation of a human female breast.

Looking momentarily to FIG. 20 a human female breast is represented by way of anatomical illustration. In general female breast is a specialized accessory gland of the skin of female mammals that secretes milk. In the human female it is a compound tubuloaveolar gland composed of 15 to 25 lobes arranged radially about the nipple and separated by connective and adipose (fatty) tissue. The smallest lobules, when fully developed, consist of clusters of rounded alveoli opening into ductules which unite to form larger tributaries of the terminal lactiferous ducts; each of the latter drains a lobe and are the same in number (15–20), converging to the areola and forming beneath it variable lactiferous sinuses or cavities which may serve as reservoirs. See generally:

Gray's Anatomy, 37$^{th}$ Edition, Churchill Livingstone, New York, 1989, p1447.

Dorland's Medical Dictionary, 27$^{th}$ Edition, W. B. Saunders Company, Philadelphia, (1988).

FIG. 20 reveals a representation of exemplary glands at 510, representative ducts at 512, and fat at 514. The areola at 516 surround the papilla at 518. Musculus pectoralis major is illustrated at 520.

Experimental and trial observation indicates that when a local anesthetic solution is injected about a vector of capture component approach towards a target lesion in the breast, it well may encounter a breast gland which has filled with local anesthetic solution. Typically, the solution is percutaneously injected at a distance, for example, 1 cm, from that vector position into the breast region at two or more locations in a somewhat surrounding locus to effect an anesthetic block. The local anesthetic solution may be injected directly into a gland or migrate into the glands under the pressure of injection to create pockets or accumulations of the anesthetic solution. Where local anesthetic is comprised, for example, of lidocaine with or without epinephrine and a normal saline solution, the arc at the capture electrodes was quenched and could not be regained with a consequence of a resultant tissue capture failure. In contrast, capture is successfully completed where a local anesthetic incorporating a diluent such as dextrose exhibiting a comparatively higher resistivity has been employed.

Figure 21A:
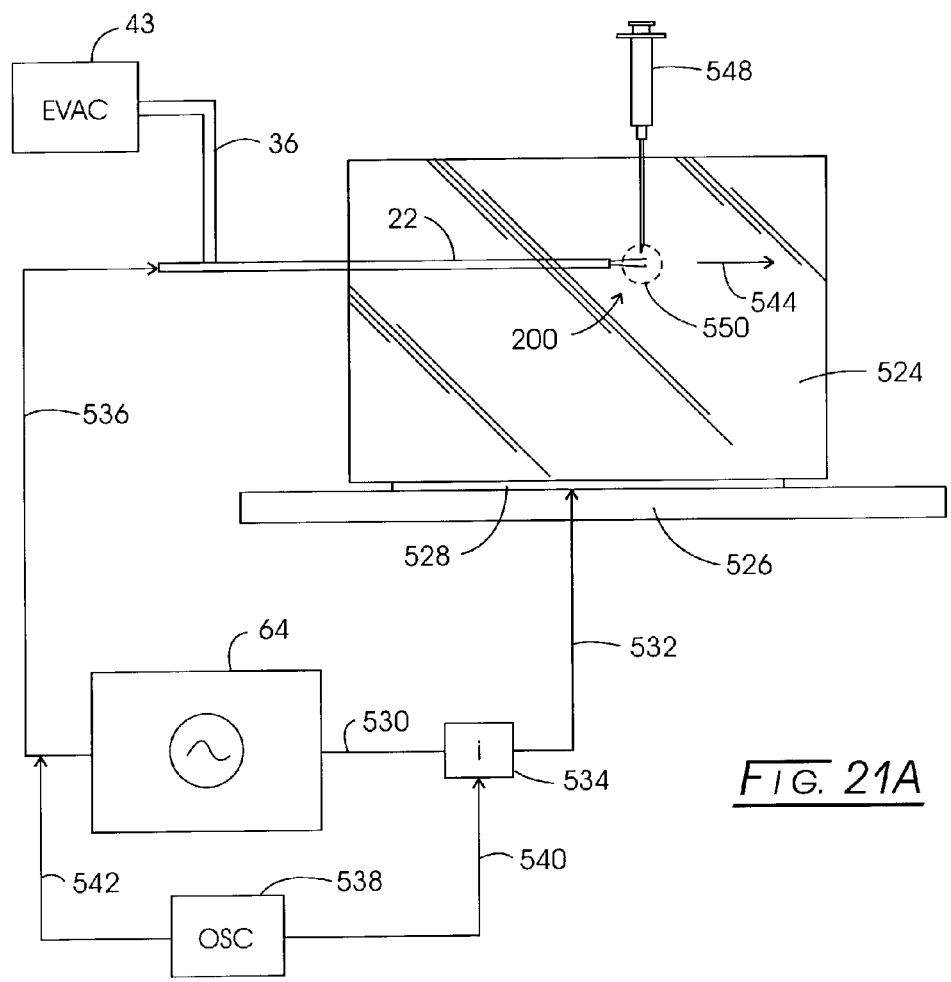
FIG. 21A is a schematic elevational view of a phantom breast study undertaken in conjunction with the method of the invention.
Figure 21B:
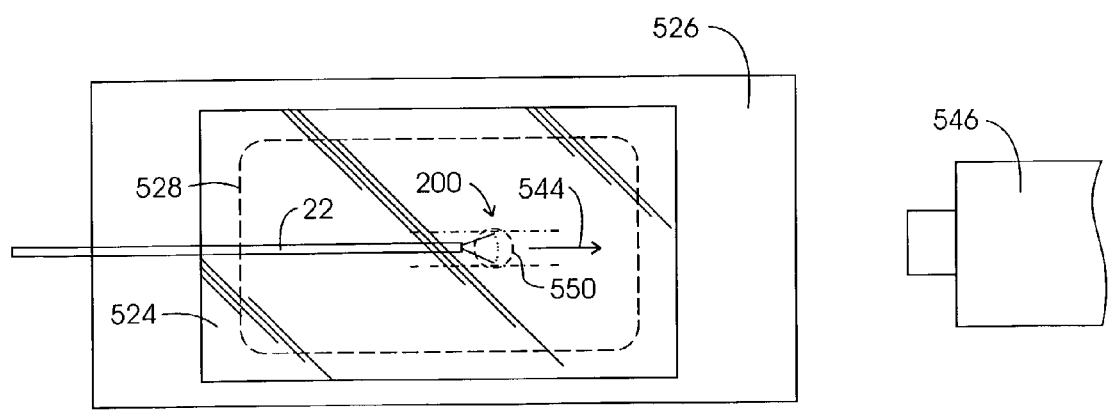
FIG. 21B is a top view of the phantom breast study undertaken in connection with FIG. 21A.

Referring to FIGS. 21A and 21B, an experimental setup is schematically illustrated wherein the effect of pockets or accumulations of local anesthetic solution upon electrosurgical capture performance was evaluated. In the figure, a breast phantom block or mass is represented at 524. The phantom 524 is a substantially transparent gel-like material which functions to emulate the physical and electrical characteristics of the human female breast and is conventionally employed for simulating clinical experience for breast biopsies. In the latter regard its resistivity is comparable to that of human breast tissue. The material is marketed under the trade designation "Ultrasonic BP Breast Phantom" by Pharmaceutical Innovations, Inc., of Newark, N.J. Block or gelatinous mass 524 is shown supported upon a support 526 and intermediate that support and the block 524 is a dispersive form of return electrode 528. A system 10 instrument 12 was employed in conjunction with a console as at 64 (FIG. 1) as shown at block 64. The delivery cannula 22 of the instrument 12 is represented in the drawings schematically. Generator and control function 64 is shown schematically as being coupled to the return electrode 528 by line 530 and arrow 532. Coupled intermediate line 530 and arrow 532 is a current detector represented at block 534. The opposite output from electrosurgical generator function 64 was supplied to the capture electrode components of the instrument 12 as represented by arrow 536 extending to electrosurgical drive functional association with delivery cannula 22 of the instrument. Note that the capture component for the instrument disposable component 16 again is represented in general at 200. An oscilloscope as represented at block 538 was coupled across outputs 530 and 536 as represented at respective arrows 540 and 542. Additionally, the evacuation system as represented at 43 (FIG. 1) was selectively employed as represented at block 43 in the instant schematic representation. The function of the suction tube 36 is represented by an arrow carrying the same numerical designation. Cannula 22 was maneuvered along linear locus represented at arrow 544 and, as seen in FIG. 21B, aligned with that linear locus 544 was the lens of a digital video camera represented at 546.

The studies at hand were carried out to illustrate and examine the effect of isolated pockets or pools of isotonic saline-based (i.e., electrically conducting) anesthetic agents and associated diluents upon the maintenance of an electrosurgical cutting arc. Studies were also performed using the much less conductive anesthetic agents with a dextrose-based diluent. In particular, the studies were performed to measure the sustainability of an electrosurgical cutting arc as the wire electrode of capture component 200 passes through the material 524 and a pocket or pool of local anesthetic. The controller or console 64 was a serial number 89140 (A1708) Model 3000 Controller as described supra which was configured with a curve 452 resistance-power profile (FIG. 16).

The testing or experimentation was commenced with the injection from a hypodermic syringe with associated needle as at 548 of a bolus of local anesthetic at an interior location within the mass 524. The bolus had a volume of 1.5 to 2.0 cc of either normal saline solution as above-described or a 5% dextrose solution as above-described. That bolus is represented in FIGS. 21A and 21B at 550. Bolus 550 had a diameter of about 1.4 cm. Testing was performed with and without the use of the evacuation system 43. Following the injection and creation of the bolus 550, the delivery cannula 22 was advanced in conjunction with a conventional capture and cutting mode of operation along the locus 544 in a manner wherein the capture cables of the capture component 200 traversed at least a portion the bolus contained pocket at 550, reentering the material 524 during the course of such cutting action as it traversed through the bolus 550. When bolus 550 contained isotonic saline diluent, i.e., when the resultant pocket was filled with isotonic saline diluent, the arc at the capture component 200 cutting cables immediately was extinguished or quenched. The arc did not return when the leading edge of capture component 200 reached and re-entered the material 524 on the opposite side of the bolus 550. It appeared that this failure to reconstitute the arc was due to an infiltration of the isotonic saline solution. That infiltration caused the solution to follow the movement of the wire electrodes of the capture component 200 to an extent lowering the resistance encountered by the generator function 64 to an extent where arc formation could not be evoked.

In contrast, when the bolus 550 contained or the corresponding pocket was filled with 1.5 cc of the 5% dextrose-based solution, then the wire electrode of the capture component 200 could traverse the pocket of bolus 550 and either sustain the arc during its traverse or resume the arc cutting mode once the pocket or bolus 550 had been traversed and the electrode wires reencountered the material 524. This reformation of the arc occurred without a boost voltage contribution.

From the foregoing, a conclusion was reached that the use of a comparatively non-conductive solution-based local anesthesia (e.g., 5% dextrose plus lidocaine and epinephrine) significantly improves the reliability of tissue capture owing to the fact that it raises the tissue electrical resistance in place of significantly lowering that tissue resistance as demonstrated in animal testing. The lowering of tissue resistance due to conventional saline-based local anesthesia is clearly one of the factors most responsible for failures to capture tissue. Although the use of saline-based local anesthesia can probably be accommodated by increasing the power profile back to the very high power levels used in the past at lower resistances (see curve 450, FIG. 16), such high power profiles result in known increased levels of thermal artifact in the recovered tissue sample having a diluent exhibiting lower condutivity. It may be observed that the use of a local anesthetic (e.g., 5% dextrose plus lidocaine with or without epinephrine) provides the following advantages:

1. Greatly increases the reliability of tissue capture.
2. Reduces the power dissipation during tissue capture (knowing the effect of increased native tissue resistance), thereby further decreasing the thermal artifact, even as compared with the curve 452 resistance-power profile (FIG. 16) which has been found to offer significantly less thermal artifact than the curve 450 profile.
3. Allows the administration of a more closely spaced "block" such as four equally spaced ("square pattern") injections of 4–5 cc each of local anesthetic at a radial distance of 1 cm. The corresponding lidocaine "block" should be sufficiently prompt to afford effective anesthesia and allow the tissue capture to proceed within 1–2 minutes after the injections are completed. In the latter regard, contrary to use of lower resistivity anesthetic solutions, if dextrose-based anesthesia is used, it is preferable to initiate tissue capture within 2 minutes to take advantage of the favorable increase in tissue resistance.
4. In view of all three benefits listed above, the most important additional benefit is that the reliability of good tissue capture with minimal thermal artifact does not depend on how much anesthesia the physician gives, where it is given or how long the physician waits before initiating the cutting/capture of tissue.
5. The dextrose-based solution infiltrates the expansible ducts or glands (FIG. 20) of the breast. It should have no effect on the ability of the system 10 to initiate or remain in the arc cutting mode whenever and wherever tissue is encountered.

It is realistic to anticipate that such pockets of local anesthetic solution will be encountered in conjunction with the use of system 10. This follows inasmuch as injections of 20 cc to about 30 cc of local anesthetic solution will be utilized by practitioners prior to carrying out a capture sequence. Thus, accommodations for fluid accumulations are to be made. Of course, where a higher resitivity diluent is utilized such as the noted dextrose-based diluents, then the fluid pocket phenomena will not defeat the necessary cutting arc formation.

Figure 22:
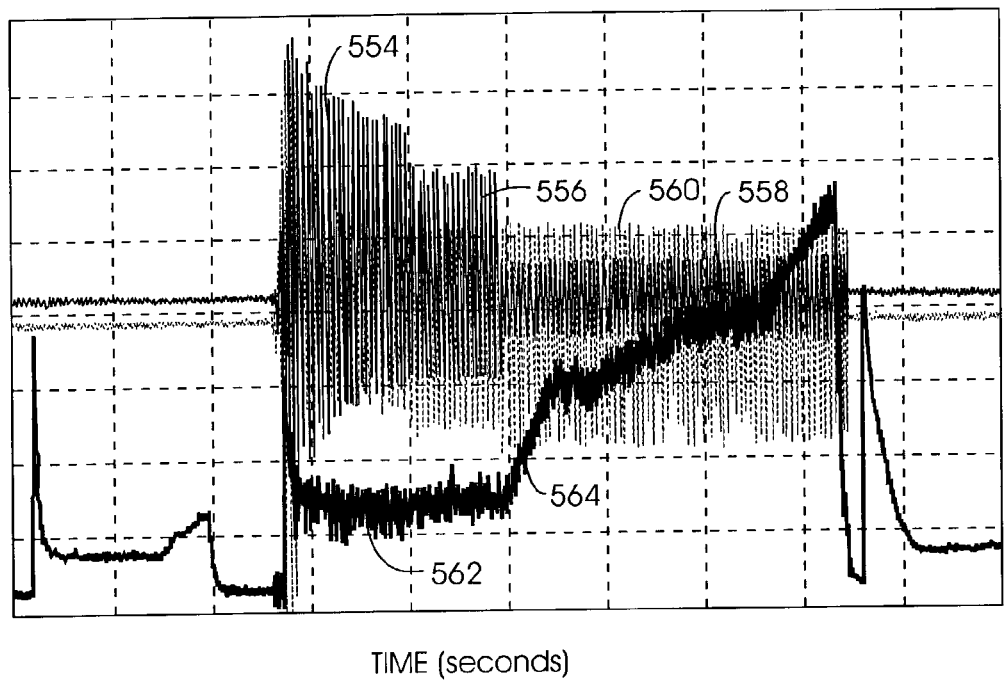
FIG. 22 is an oscillotrace of an electrosurgical generator output monitored during an animal study wherein a saline-based local anesthetic was employed.
Figure 23:
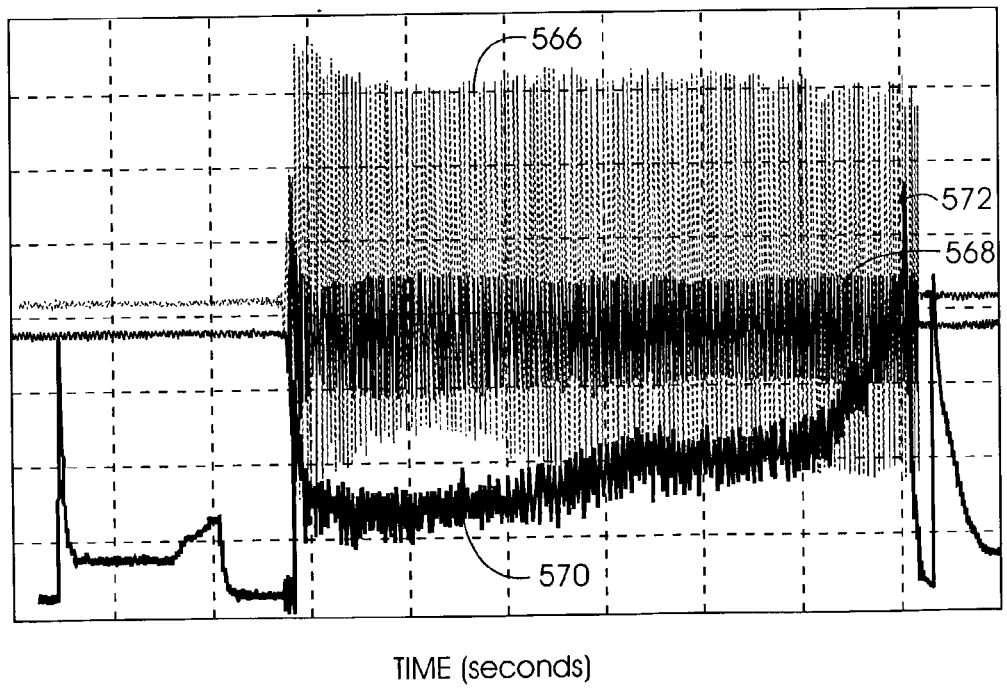
FIG. 23 is an oscillotrace of an electrosurgical generator output undertaken with the animal study of FIG. 22 but utilizing a dextrose-based local anesthetic.

Oscillotrace based outlines of the electrosurgical drive voltage and current as well as the current response of motor assembly 160 generated during animal (pig) studies carried out with system 10 are presented at FIGS. 22 and 23. Both of these oscillotrace outlines were derived in conjunction with the use of a consol 64 serial number 89140. For the trial deriving FIG. 22, a saline-based 0.5% lidocaine local antiseptic agent with epinephrine was combined in solution with a normal saline diluent. Arc voltage including the initializing boost voltage is represented at 554. Note that the arc was lost at position 556 and was not reinstituted as represented by the low voltage response at oscillotrace region 558. Electrosurgical current as represented at 560 was of relatively high amplitude reflecting a low resistance. The drive current exhibited by motor assembly 160 is represented at 562. Note that following loss of arc, at current region 564 the oscillotrace exhibits a motor current increase characteristic which indicates that arc cutting has ceased and the deployment is proceeding mechanically.

Looking to FIG. 23, a corresponding oscillotrace is provided taken in conjunction with the same system 10 and with the same animal on the same date. However, the local anesthetic employed was 0.8% lidocaine with epinephrine in solution with a 5% dextrose diluent. Note that the capture cables or pursing cable excitation voltages at 566 remain elevated following an initial boost interval. Further, the excitation current is of lower amplitude and constant as represented at 568. Note, additionally, that the motor energization current at 570 remains somewhat consistent until the completion of capture and resultant motor 160 stall as seen at 572.

The above-discussed studies and experimentation concerning the electrosurgical performance of system 10 additionally have led to a refinement of the protocol or procedure of its use. In particular, the evacuation system 43 as it extends to the intake ports 35 (FIG. 1) beneficially may carry out an evacuation of local anesthetic fluids at the situs of capture. In this regard, the capturing sequence wherein the capture component 200 is deployed may be carried out in an intermittent manner. For example, by intermittently depressing foot pedal 88c or capture switch 58 leafs 210–214 and corresponding cables 230–234 may be excited and advanced, for example 2 seconds, whereupon foot pedal 88c or switch 58 is released such that the system enters into a pause mode indicated by the illumination of LED 104(FIG. 1). The pause mode dwell then will ensue for, for example 4 seconds, whereupon foot switch 88c again is depressed or capture switch 58 is actuated for another 2 seconds. For an implementation of system 10 for capturing at a maximum diametric extent of 10 mm, the total capture sequence, if carried out continuously, would require about 6 seconds. Thus, to complete the corresponding intermittent type of capture activity a total elapsed time of about 14 seconds is called for.

Figure 24A:
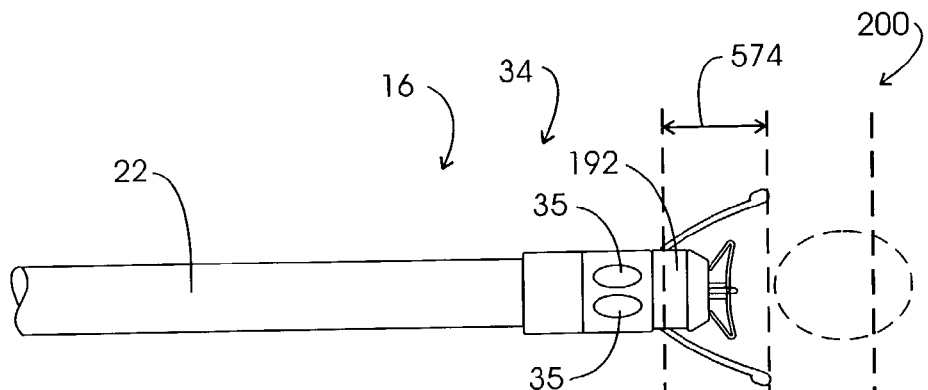
FIGS. 24A–24C combine to illustrate an intermittent actuation of the instrument of FIG. 2.
Figure 24B:
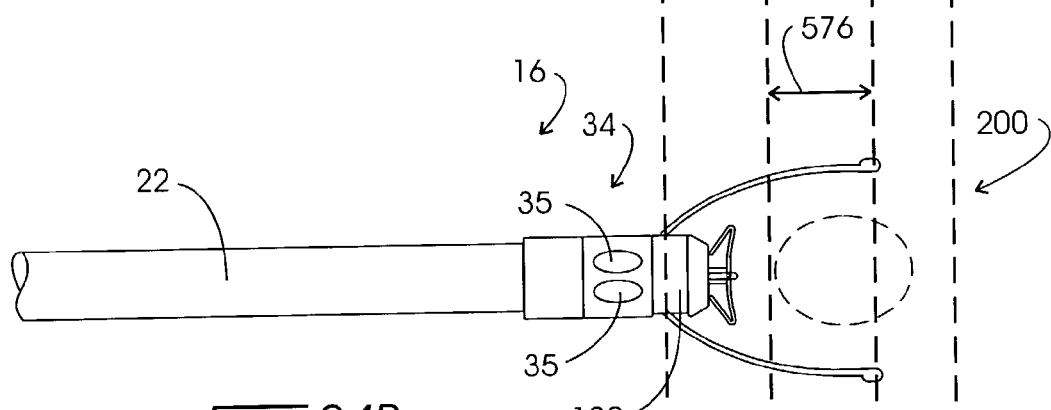
Figure 24C:
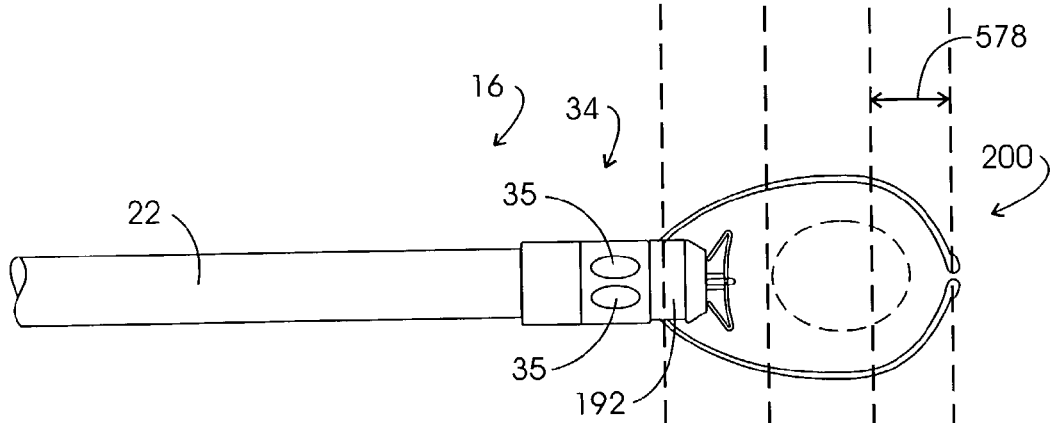

Looking to FIGS. 24A–24C this intermittent approach to capture is schematically illustrated. In FIG. 24A the capture component 200 is revealed having an orientation following the initial 2 seconds of deployment and electrosurgical cutting. That initial 2 second performance is represented at arrow 574. For the next 4 seconds, the system 10 is maintained in a pause mode during which time any accumulated local anesthetic solution is evacuated through ports 35 of the disposable component 16. During this pause interval, additionally, the practitioner may observe transparent evacuation tube 36 for the presence of clear fluids. The protocol also is beneficial where a higher level of bleeding is encountered, it being recalled from the discourse in connection with FIG. 15 that blood exhibits a comparatively low electrical resistivity which may have an adverse effect upon the electrosurgical activity of the system. In general, as long as the practitioner perceives that fluid evacuation is taking place, the pause interval will be maintained. FIG. 24B illustrates a next occurring energization of the motor assembly 160 and excitation of the capture component cables. Following this 2 second activation as represented at arrow 576, a pause interval again is entered for, for example, about 4 seconds. As before, the transparent evacuation tubing 36 is observed by the practitioner during this pause interval. FIG. 24C illustrates the completion of the procedure with the energization of the capture cables and deployment of capture component leaves 210–214 to a fully pursed orientation. Such activity is represented at arrow 578.

As discussed in connection with FIG. 14, with each activation of foot switch 88c or capture switch 58, a boost voltage is applied to the electrosurgical excitation components with a corresponding increase in power. For earlier protocols employed with system 10, this voltage was generated only at the initial excitation of the capture component electrodes as opposed to being applied an additional two times during a capture interval under the instant protocol. The initial boost interval for earlier protocols was elected as being that of sufficient duration to assure the formation of an electrosurgical cutting arc and was selected as 375 milliseconds with respect to the interval during which a signal was applied from the control system calling for a boost activity. However, with the multiple boost occurrence, of the instant protocol, it is desirable to limit the boost signal interval to avoid the formation of thermal artifacts in the recovered tissue specimen. Accordingly, the boost interval control signal now is reduced to that necessary to create a cutting arc with minimal power generation.

Figure 25:
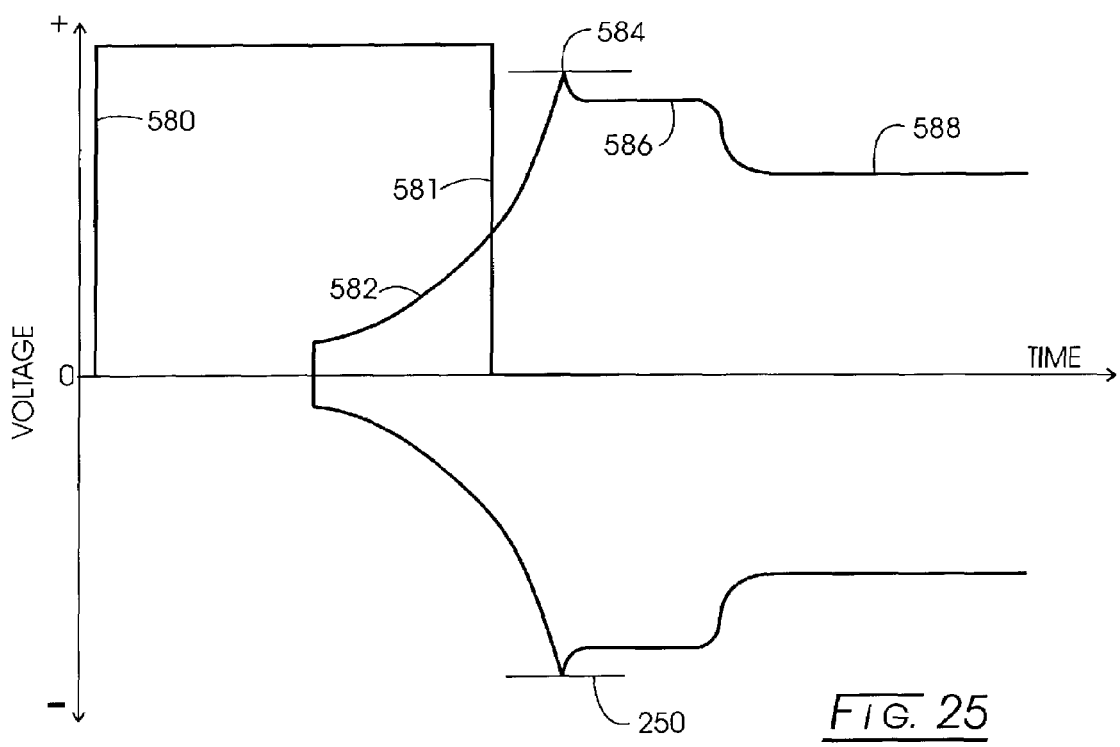
FIG. 25 is an oscillotrace outline and boost control signal representation illustrating an optimization of boost level voltages.

Referring to FIG. 25, an oscillotrace outline of the voltage output of system 10 as a boost interval is generated is set forth in conjunction with a representation of the commencement and termination of a boost control signal having a shortened duration of 250 milliseconds. In the figure, the boost control signal is represented as commencing at time, t=0 as represented at vertical line 580. The cut off for this boost control signal is represented at 250 ms shown at vertical line 581. The voltage oscillotrace shows a voltage ramp-up component 582 commencing in time after the initiation of the boost control signal as represented at line 580. This is due to delays occasion by relays employed in the high voltage output stage 400 (FIG. 14). Ramp 580 occurs for about 118 milliseconds reaching a peak level at position 584, whereupon about a 55 millisecond ramp level 586 ensues. At the termination of that ramp 586, the system ramps to the lower continuous voltage level 588 where, for the duration of the cutting maneuver the voltage is essentially maintained at a constant value. Where the boost signal otherwise extending between lines 580 and 581 are reduced to 125 milliseconds, the ramp peak 584 was not reached to the extent that the boost was ineffective. However, at 250 milliseconds duration for the boost control signal a boost activity of about 160 milliseconds is witnessed which provides adequate boost voltage assurance of cutting arc generation at a beneficially minimized energy generation. By contrast, where the full 375 millisecond boost control duration is applied, the ramp component 586 of the boost voltage is sustained for about 180 milliseconds.

Referring to Table 3 an energy balance analysis is provided in tabular form with respect to boost control signal durations of 200 milliseconds, 250 milliseconds and the basic interval of 375 milliseconds. Tabulations are set forth with respect to tissue or load resistances as seen by the system 10 as set forth in column one. Column two tabulates energy generated during the ramp-up to boost voltage as described in connection with component 582 in FIG. 25. The data in column two was calculated by numerical integration in 16 steps of 6.63 milliseconds per step over a 106 millisecond ramp up period. Looking to column three, the total energy generated for a 200 millisecond boost control signal duration is tabulated with respect to load resistance. For a boost control signal duration of 200 milliseconds, the applied voltage just reaches the boost voltage as identified at peak 584 in FIG. 25. For this signal interval, no ramp as at 586 occurs at boost voltage. The caloric values of column three may be compared with those in column seven which tabulates the total energy generated for the standard or basic boost interval signal of 375 milliseconds. As seen in column eight, the 200 millisecond boost control signal duration provides a caloric heat generation which is 17% of the caloric generation for a boost control signal duration of 375 milliseconds as set forth in column seven. As apparent, for the intermittent utilization of the system 10 this minimized duration boost control signal will substantially reduce thermal artifact at the recovered tissue sample.

Now looking to the utilization of a boost control signal of 250 millisecond duration as discussed in conjunction with FIG. 25, column four tabulates the energy derived from the plateau region 586 with respect to tissue or load resistance. As tabulated in column nine this, when combined with the energy below the ramp-up region 582 reduces the overall caloric expenditure per energization to 42% of that generated with the conventional 375 millisecond boost control signal. In the latter regard, the 180 millisecond plateau region energy for the 375 millisecond boost control signal interval is tabulated in column 6. Finally, column ten tabulates the amount of energy involved for a continuous mode of capture where a maximum diametric capture extent of 10 millimeters is achieved with the capture component 200. For the generation of the data set forth in Table three, the resistance-power profile 452 (FIG. 16) was assumed.

TABLE 3

Calculated Energy Associated With Boost Control Signal Durations Of 200, 250 And 375 Milliseconds

| Tissue Resistance (Load Resistance Seen By Controller) (ohms) | Energy Generated During Ramp Up To Boost Voltage (See Note 1) (Calories) | Total Energy Generated For 200 Msec. Boost Control Signal Duration (See Note 2) (calories) | Energy In 55 Msec. Plateau Region After Boost Voltage Reached T(Boost) = 250 Msec. (calories) | Total Energy Generated For 250 Msec. Boost Control Signal Duration (See Note 3) (calories) |
|---|---|---|---|---|
| 100 | 63.1 | 63 | 97 | 160 |
| 150 | 42.1 | 42 | 65 | 107 |
| 200 | 31.6 | 32 | 49 | 80 |
| 250 | 25.2 | 25 | 39 | 64 |
| 300 | 21.0 | 21 | 32 | 53 |
| 350 | 18.0 | 18 | 28 | 46 |
| 400 | 15.8 | 16 | 24 | 40 |
| 500 | 12.6 | 13 | 19 | 32 |
| 600 | 10.5 | 11 | 16 | 27 |
| 700 | 9.0 | 9 | 14 | 23 |
| 800 | 7.9 | 8 | 12 | 20 |
| 900 | 7.0 | 7 | 11 | 18 |
| 1000 | 6.3 | 6 | 10 | 16 |
| 1100 | 5.7 | 6 | 9 | 15 |
| 1200 | 5.3 | 5 | 8 | 13 |
| 1300 | 4.9 | 5 | 7 | 12 |
| 1400 | 4.5 | 5 | 7 | 11 |
| 1500 | 4.2 | 4 | 6 | 11 |
| 1600 | 3.9 | 4 | 6 | 10 |
| 1700 | 3.7 | 4 | 6 | 9 |
| 1800 | 3.5 | 4 | 5 | 9 |
| 1900 | 3.3 | 3 | 5 | 8 |
| 2000 | 3.2 | 3 | 5 | 8 |

| Energy In 180 Msec. Plateau Region After Boost Voltage Reached T(Boost) = 375 Msec. (calories) | Total Energy Generated FOR 375 Msec. Boost Control Signal Duration (See Note 4) (calories) | Fraction Of Boost Energy Generated With 200 Msec. Boost Duration (See Note 5) (%) | Fraction Of Boost Energy Generated With 250 Msec. Boost Duration (See Note 5) (%) | Total Energy Generated During 6 Sec. Continuous Mode Period Of 10 Mm Capture (See Note 6) "4–18 Profile" (Calories) |
|---|---|---|---|---|
| 318 | 381 | 17% | 42% | 143 |
| 212 | 254 | 17% | 42% | 163 |
| 159 | 190 | 17% | 42% | 183 |
| 127 | 152 | 17% | 42% | 202 |
| 106 | 127 | 17% | 42% | 221 |
| 91 | 109 | 17% | 42% | 224 |
| 79 | 95 | 17% | 42% | 228 |
| 64 | 76 | 17% | 42% | 240 |
| 53 | 63 | 17% | 42% | 236 |
| 45 | 54 | 17% | 42% | 234 |
| 40 | 48 | 17% | 42% | 224 |
| 35 | 42 | 17% | 42% | 216 |
| 32 | 38 | 17% | 42% | 211 |
| 29 | 35 | 17% | 42% | 198 |
| 26 | 32 | 17% | 42% | 192 |
| 24 | 29 | 17% | 42% | 187 |
| 23 | 27 | 17% | 42% | 172 |
| 21 | 25 | 17% | 42% | 162 |
| 20 | 24 | 17% | 42% | 153 |
| 19 | 22 | 17% | 42% | 144 |
| 18 | 21 | 17% | 42% | 136 |
| 17 | 20 | 17% | 42% | 129 |
| 16 | 19 | 17% | 42% | 122 |

Note 1-Energy generated during ramp up from 0 volts to Boost Voltage calculated by numerical integration in 16 steps of 6.63 msec./step over the 106 msec ramp-up period. Energy = (Summation [(Voltage rms)$^2$]* (incremental time period))/(Resistance of tissue) where the summation is for j = 1 to 16.

Figure 26:
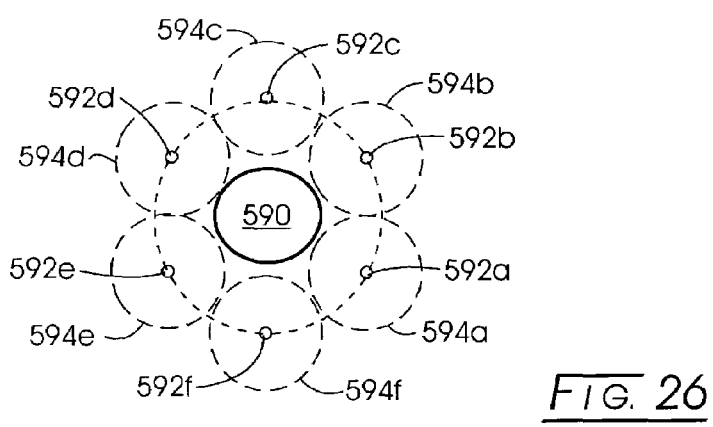
FIG. 26 is a schematic view of a local anesthetic injection protocol demonstrating an ensemble effect.

Looking to FIG. 26, a schematic representation of a local anesthetic injection protocol pattern is portrayed. For example, a target lesion is portrayed at 590 as exhibiting about a 10 millimeter maximum diametric extent. To carry out infiltration anesthesia, a sequence of 6 injections 592a–592f are provided. The sphere of fluid influence for each of these injections 592a–592f are represented respectively at 594a–594f. These spheres of influence will interact in what is referred to as an "ensemble effect" of multiple injections even though these injections are positioned about two centimeters from the center of the lesion 590. Where a singular injection is employed, as evidenced in connection with Appendix A, little influence in the region of the lesion 590 would be observed. The "ensemble effect" additionally indicates that pockets or accumulations of local anesthetic fluid or solution generally will be encountered in any given procedure. Thus the intermittent form of capture is beneficial in removing pockets of fluid anesthesia and the like.

Tables 4A and 4B should be considered together for a sequence of capture trial numbers extending from number 1 through number 25. The resultant table summarizes an animal (pig) study undertaken at the Medical Center of the Ohio State University on Jun. 12, 2002. For these trials, a lidocaine anesthetic agent was utilized in conjunction with epinephrine and a noted dextrose based diluent. Capture trial numbers 1 through 8 and 20 through 25 were carried out in a continuous mode wherein the continuous operation of the capture component 200 extended for an interval of about six seconds. Capture trial numbers 9 through 19 were carried in an intermittent fashion wherein capture component 200 was energized for 2 seconds following which a pause mode was entered for 4 seconds and so on. As before, a capture failure was considered to include no sample or a very small sample or sample which is obtained in small pieces indicating mechanical rather than electrosurgical cutting. The tabulated average resistance and minimum resistance refers to resistances calculated based upon measured RF voltage and current during the period of boost or capture. Trial number nine failed in consequence of a failure of cable stop 292 (FIG. 10) to remain in fixed position. Capture trial number seven failed to derive a sample, a 0 level of boost voltage being witnessed. Additionally, as before, the first digit of the anesthetic protocol refers to the number of injections. The second digit of this protocol refers to the volume of injection bolus in cc. The third digit of protocol refers to the spacing of the injection from the centerline of the target tissue and the fourth digit of the protocol refers to the dwell time between injection and commencement of capture in minutes. Note that the same protocol was used for all trials. Where a pulsed mode (intermittent) is at hand, then the range of powers are given corresponding to all of the periods of capture, albeit intermittent. Trial number 25 was undertaken in the liver of the animal and trial number 16 resulted in a relatively high, 128 degree F. temperature. Note that trials number 1–2 and 20–25 were undertaken with a boost control signal duration of 375 milliseconds. Capture trials 3–4 and 15–19 were undertaken with a boost control signal of 250 millisecond duration operating in a pulsed (intermittent) mode. Capture trial numbers 5 through 8 were undertaken with a boost control signal of 125 ms duration in a continuous mode of operation. Correspondingly, trials 9–14 were undertaken with a boost control signal of 125 ms duration in a pulsed (intermittent) mode. The differences in peak power during boost activity in watts may be observed for capture trials 5–8 as compared with capture trials 10–14.

Averages for average resistance of tissue; minimum resistance of tissue; peak power during boost; average power during capture; average specimen diameter; shaft temperature just after fully disposable component 16 is withdrawn and the weight of the specimen are provided below the trial tabulations. These averages are carried out in conjunction with the labeled resistance-power profile, boost control signal duration and capture mode identification.

TABLE 4A

| Model 3000 Controller Serial No. (Type) | Power & Voltage Profile | Boost Voltage Setting (Volts Rms) | Boost Duration (Msec) | Probe Size (Mm) |
|---|---|---|---|---|
| 89131 | 454 | 447 | 375 | 10 |
| 89131 | 454 | 447 | 375 | 10 |
| 89140 | 450 | 447 | 250 | 10 |
| 89140 | 450 | 447 | 250 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 125 | 10 |
| 89140 | 450 | 447 | 250 | 10 |
| 89140 | 450 | 447 | 250 | 10 |
| 89140 | 450 | 447 | 250 | 10 |
| 89140 | 450 | 447 | 250 | 10 |
| 89140 | 450 | 447 | 250 | 10 |
| 89131 | 454 | 447 | 375 | 10 |
| 89131 | 454 | 447 | 375 | 10 |
| 89131 | 454 | 447 | 375 | 10 |
| 89131 | 454 | 447 | 375 | 10 |
| 89131 | 454 | 447 | 375 | 10 |
| 89131 | 454 | 447 | 375 | 10 |

Note that these ranges do not include capture in liver

TABLE 4A-continued

| Operating Mode | Anesthetic Protocol | Probe No. | Probe Lot No. | Capture Trial No. | Sample No. | Average Resistance Of Tissue (Ohms) | Minimum Resistance Of Tissue (Ohms) | Peak Power During Boost (Watts) |
|---|---|---|---|---|---|---|---|---|
| Continuous | 4 × 5 × 1 × 1 | M6-5-06 | 515032a | 1 | 1 | 1322 | 382 | 471 |
| Continuous | 4 × 5 × 1 × 1 | M6-5-07 | 515032a | 2 | 2 | 1552 | 636 | 287 |
| Continuous | 4 × 5 × 1 × 1 | M6-5-08 | 515032a | 3 | 3 | 1176 | 526 | 342 |
| Continuous | 4 × 5 × 1 × 1 | M6-5-09 | 515032a | 4 | 4 | 1854 | 612 | 294 |
| Continuous | 4 × 5 × 1 × 1 | M6-5-10 | 515032a | 5 | 5 | 1333 | 358 | 341 |
| Continuous | 4 × 5 × 1 × 1 | M6-5-11 | 515032a | 6 | 6 | 1156 | 504 | 283 |
| Continuous | 4 × 5 × 1 × 1 | M6-5-12 | 515032a | 7 | No Sample | 580 | 265 | 319 |
| Continuous | 4 × 5 × 1 × 1 | M6-5-13 | 515032a | 8 | 7 | 750 | 159 | 364 |
| Pulsed Mode | 4 × 5 × 1 × 1 | M6-5-14 | 515032a | 9 | No Sample | Not Collected | Not Collected | — |
| Pulsed Mode | 4 × 5 × 1 × 1 | M6-5-15 | 515032a | 10 | 8 | 1487 | 615 | 163 |
| Pulsed Mode | 4 × 5 × 1 × 1 | M6-5-16 | 515032a | 11 | 9 | 628 | 236 | 246 |
| Pulsed Mode | 4 × 5 × 1 × 1 | M6-5-17 | 515032a | 12 | 10 | 873 | 560 | 174 |
| Pulsed Mode | 4 × 5 × 1 × 1 | M6-5-18 | 515032a | 13 | 11 | 532 | 194 | 243 |
| Pulsed Mode | 4 × 5 × 1 × 1 | M6-5-19 | 515032a | 14 | 12 | 1036 | 535 | 124 |
| Pulsed Mode | 4 × 5 × 1 × 1 | M6-5-20 | 515032a | 15 | 13 | 869 | 266 | 365 |
| Pulsed Mode | 4 × 5 × 1 × 1 | M6-5-21 | 515032a | 16 | 14 | 329 | 280 | 418 |
| Pulsed Mode | 4 × 5 × 1 × 1 | M6-5-22 | 515032a | 17 | 15 | 849 | 324 | 236 |
| Pulsed Mode | 4 × 5 × 1 × 1 | M6-5-23 | 515032a | 18 | 16 | 761 | 289 | 366 |
| Pulsed Mode | 4 × 5 × 1 × 1 | M6-5-25 | 515032a | 19 | 17 | 233 | 341 | 307 |
| Continuous | 4 × 5 × 1 × 1 | M6-5-27 | 515032a | 20 | 18 | 873 | 662 | 262 |
| Continuous | 4 × 5 × 1 × 1 | S/N 36 | 519042a | 21 | 19 | 808 | 413 | 422 |
| Continuous | 4 × 5 × 1 × 1 | S/N 03 | 519042a | 22 | 20 | 1326 | 461 | 384 |
| Continuous | 4 × 5 × 1 × 1 | M6-5-29a | 515032a | 23 | 21 | 699 | 462 | 403 |
| Continuous | 4 × 5 × 1 × 1 | M6-5-28 | 515032a | 24 | 22 | 991 | 301 | 390 |
| Continuous | 4 × 5 × 1 × 1 | M6-5-29b | 515032a | 25 | 23 | 284 | 91 | 540 |
| Averages For "454 Profile" With 375 Msec. Boost Duration | | | | | | 1082 | 474 | 374 |
| Averages For "450 Profile" With 250 Msec. Boost (Cont. & Pulsed) | | | | | | 867 | 377 | 333 |
| Averages For "450 Profile" With 250 Msec. Boost (Cont. & Pulsed) | | | | | | 1515 | 569 | 318 |
| Averages For "450 Profile" With 250 Msec. Boost (Cont. & Pulsed) | | | | | | 608 | 300 | 338 |
| Averages For "450 Profile" With 125 Msec. Boost (Cont. & Pulsed) | | | | | | 931 | 381 | 251 |
| Averages For "450 Profile" With 250 Msec. Boost (Cont. & Pulsed) | | | | | | 955 | 322 | 327 |
| Averages For "450 Profile" With 250 Msec. Boost (Cont. & Pulsed) | | | | | | 911 | 428 | 190 |

TABLE 4B

| Capture Trial No. | Average Power During Capture (Watts) | Average Specimen Diameter | Shaft Temperature Measured Just After Probe Withdrawn (Degree F.) | Weight Of Specimen (or Failure) (Grams) | Type of Tissue Being Captured | Damage To Parylene & Polyimide | Damage To Plastic Components At Probe Tip | Stimulation Level During Capture? | Additional Comments |
|---|---|---|---|---|---|---|---|---|---|
| 1 | 134 | 10.5 | 103 | 0.480 | fibrous | Heavy-1 leaf only | Very Minor | Yes | Time to form cutting arc = 70 msec. |
| 2 | 112 | 11.5 | 93 | 0.708 | fatty | Minor | None | Yes | Time to form cutting arc = 118 msec. |
| 3 | 153 | 9.5 | 94 | 0.458 | ? | Minor | None | Low | Time to form cutting arc = 78 msec. |
| 4 | 89 | 9.0 | 114 | 0.717 | ? | Medium-1leaf | None | Medium | Time to form cutting arc = 88 msec. |
| 5 | 135 | 9.3 | 95 | 0.437 | ? | Very Minor/None | None | No | |
| 6 | 150 | 7.0 | | 0.225 | ? | Very Minor/None | None | No | Time to form cutting arc = 112 msec. |
| 7 | 238 | | 95 | No sample | fibrous | Very Minor/None | None | No | Boost voltage only rose to 660 Vpp, time to form arc = 100 msec. |
| 8 | 205 | 8.5 | 100 | 0.445 | ? | Minor | None | No | |

TABLE 4B-continued

| Capture Trial No. | Average Power During Capture (Watts) | Average Specimen Diameter | Shaft Temperature Measured Just After Probe Withdrawn (Degree F.) | Weight Of Specimen (or Failure) (Grams) | Type of Tissue Being Captured | Damage To Parylene & Polyimide | Damage To Plastic Components At Probe Tip | Stimulation Level During Capture? | Additional Comments |
|---|---|---|---|---|---|---|---|---|---|
| 9 | | | | No sample | ? | Very Minor/None | None | No | Hub Stop failure |
| 10 | 73 | 7.3 | 88 | 0.446 | ? | Very Minor/None | None | No | |
| 11 | 180 | 9.5 | 105 | 0.583 | fibrous | Very Minor/None | None | No | |
| 12 | 98 | 9.0 | 93 | 0.439 | ? | Very Minor/None | None | No | |
| 13 | 192 | 11.3 | 98 | 0.587 | fibrous | Very Minor/None | None | No | |
| 14 | 92 | 8.8 | 98 | 0.433 | fibrous | Very Minor/None | None | No | |
| 15 | 184 | 10.8 | 104 | 0.597 | fibrous | Very Minor/None | None | No | |
| 16 | 178 | 9.8 | 129.000 | 0.466 | fibrous | Medium-1 leaf | None | No | |
| 17 | 104 | 8.8 | 94 | 0.574 | fatty | Very Minor/None | None | No | |
| 18 | 171 | 10.0 | 111 | 0.551 | fatty | Very Minor/None | None | No | |
| 19 | 199 | 9.3 | 96 | 0.431 | fibrous | Medium | None | No | |
| 20 | 195 | 9.5 | 101 | 0.578 | fibrous | Very Minor/None | None | No | |
| 21 | 215 | 9.5 | 103 | 0.533 | fibrous | Very Minor/None | None | No | |
| 22 | 123 | 10.3 | 102 | 0.578 | fatty | Very Minor/None | None | No | |
| 23 | 241 | 10.8 | 119 | 0.673 | very fibrous | Very Minor/None | None | No | |
| 24 | 179 | 10.0 | 119 | 0.474 | fibrous | Very Minor/None | None | No | |
| 25 | 303 | 14.5 | | 0.830 | liver | Medium | Significant | No | Capture in liver |
| | 171 | 10.3 | 106 | 0.575 | | | | | |
| | 154 | 9.6 | 106 | 0.542 | | | | | |
| | 121 | 9.3 | 104 | 0.588 | | | | | |
| | 167 | 9.7 | 107 | 0.524 | | | | | |
| | 151 | 8.8 | 97 | 0.449 | | | | | |
| | 182 | 8.3 | 97 | 0.369 | | | | | |
| | 127 | 9.2 | 96 | 0.498 | | | | | |

A local anesthetic utilizing a dextrose-based diluent may be prepared for utilization in accordance with the precepts of the instant invention utilizing a commercially available 5% dextrose intravenous (IV) solution which is available in 100 ml, 250 ml, 500 ml and 1000 ml bags. Also as a source material, two-gram vials of 20% lidocaine (for cardiac arrhythmias) are available as well as 1 mg ampules of 0.1% epinephrine. To prepare each 100 ml of local anesthetic solution, 6 ml of the above noted IV solution is removed from the IV fluid bag. To this is added 1,000 mg (5 ml of 200 mg/ml) lidocaine and 0.5 mg (0.5 ml of 1 mg/ml) epinephrine.

As another approach to formulate 0.8% lidocaine in D5W with 1:200,000 epinephrine, a 0.8% lidocaine in a pre-mixed intravenous (IV) bag is provided. These bags are available in 250 ml and 500 ml bags intended for the treatment of cardiac arrhythmias. The aqueous solutions are marketed by Abbott Laboratories, North Chicago, Ill. Additionally, provided as a source are 1 mg ampules of 0.1% epinephrine. To formulate each 250 mls of local anesthetic solution for utilization with the instant procedure, 1.5 ml of the IV solution is removed from the fluid bag. To this is added 1.25 mg (1.25 ml of 1/mg/ml) epinephrine. As indicated above, lidocaine hydrochloride with a dextrose diluent is indicated for use in conjunction with the acute management of cardiac arrhythmias and for that purpose is administered intravenously.

FIGS. 27A–27G combine as labeled thereon to provide a flow chart describing the operation of the instant system, particularly as it performs in a pulsed or intermittent mode of capture. In the discourse to follow, the term "handle" refers to reusable component 14 (FIG. 1). Looking to FIG. 27A, the procedure starts as represented at block 600 and line 602 providing for the connection of connector 66 of cable 62 to console connector 68. Next, as represented at block 604 and line 606 controller 64 is turned on by actuating front panel switch 82. As this occurs, a handle interlock test is carried out. In this regard, an interlock current is caused to pass through a coding resistor present in the reusable component 14. If the test for this interlock connection is passed, then green LED 86, above console connector 68 will be illuminated. As represented by the query posed at block 608, where LED 86 is not energized, then the procedure reverts as indicated at line 610 and block 612, the practitioner being pre-instructed to check for a proper handle (component 14) connection and if that connection is proper, the component 14 is replaced. For either of these improper conditions, the procedure loops to commencement block 600 as represented at line 614 and 616. Where the query posed at block 608 indicates that proper handle (component 14) connection is present and the green LED 86 is illuminated, then the procedure continues as represented at line 618 and block 620. Turning on the switch 82 also causes the carrying out of the self-test features of POSM system 412 as described in connection with FIG. 14. Block 620 calls for an actuation of the console mounted start/reset switch 92. This causes the motor assembly 160 to be energized in a reverse sense to cause the rotation of translation component 172 (FIG. 3) and the driving of transfer assembly 176 rearwardly until the nut 178 engages a bulkhead surface (not shown) adjacent seal chamber 170. This creates a motor stall condition and in response thereto the motor assembly 160 is energized in a forward sense for 0.125 second to relax the thus caused axial load. This dual energization procedure is monitored. As represented at line 622 and block 624, a determination is made as to whether the green LED below the start/reset icon on reusuable component 14 as well as the corresponding green LED 94 at console 64 is illuminated. Where those LEDs are not illuminated, the activity described at block 620 failed and the procedure reverts as represented at line 626 and block 628, the practitioner having been pre-instructed that a faulty cable or "handle" is at hand and the procedure returns to starting block 600 as represented at lines 630 and 616. Actuation of switch 92 also causes the carrying out of the test for proper connection of dispersive return electrode 70 by the PCSM system 412. A failure to pass this test results in the flashing of red LED 106, a generation of a pulsing sound output, and the procedure is halted.

Where the query posed at block 624 results in an affirmative determination with the illumination of the noted green LEDs, then as represented at line 632 and block 634 the practitioner inserts the disposable probe component 16 into the reuseable component 14 or "handle". The program then continues as represented at line 636 and block 638 (FIG. 27B), providing for the administration of a local anesthetic at the skin level in the region of the intended biopsy. In accordance with the precepts of the invention this local anesthetic will be provided as a solution of anesthetic agent and a biocompatible diluent which exhibits an electrical conductivity or resistivity of value which is effective for sustaining a tissue cutting arc when the solution is infiltrated within tissue in the region of the intended biopsy. In general, the solution of local anesthetic agent and diluent will exhibit a reisistivity corresponding with or greater than the lowest value of resistivity anticipated to be encountered in the tissue of the anticipated capture region. The solution will exhibit an electrical resistivity of about 100 ohm-cm or greater and preferably about 200 ohm-cm or greater. The solution further should exhibit an osmolarity between about 240 and about 340 milliOsmold/liter. The electrical conductivity of the solution should be low enough to permit the sustaining of a cutting arc even though temporary quenching of the arc may be encountered in pockets of the solution. Preferably the electrical conductivity of the anesthetic solution should be less than 5 milliSiemens/cm. In this regard, the arc should be reconstituted as soon as the capture component traverses such solution-filled pockets or accumulations of solution.

Dextrose in water having dextrose concentrations between about 3.75% dextrose and less than about 10% dextrose, where dextrose is D-glucose monohydrate ($C_6H_{16}O_6 \cdot H_2O$), a hexose sugar freely soluble in water, meet the criteria of sustaining a cutting arc. The dextrose-based local anesthetic for infiltration anesthesia also can include other additives such as epinephrine in a ratio of 1 part epinephrine and 200,000 parts anesthetic solution. Epinephrine often is added to infiltration anesthetics since it is a vasoconstrictor which slows the vascular uptake of the anesthetic agent, thereby prolonging the duration of the anesthesia and reducing bleeding. Other active anesthetic agents that may be combined with the diluent for use in infiltration anesthesia include bupivacaine, ropivicaine, etidocaine, procaine, chloroprocaine, tetracaine, prilocaine and mepivicaine.

As indicated by the resistance measuring data, for example, as set forth in Appendix A, it is desirable to carry out the capture procedure soon after the administration of local anesthetic exhibiting the noted low conductivity. Resistance encountered early following the administration of the local anesthetic will be advantageously at higher values. Accordingly, following the administration of local anesthetic, as represented at line 640 and block 642 a cold scalpel is employed to make a skin incision to a depth of about 4 mm and a length approximately 2 mm wider than the maximum width of the precursor electrode. Then, as represented at line 644 and block 646 the vacuum or evacuator assembly 43 is turned on, for example, at switch 50 and the transparent evacuation tubing 36 is coupled to the disposable component probe 16. As discussed at block 436 in connection with FIG. 14, the control system at console 64 may be configured to mandate this turning on of the evacuation assembly 43 before the system can continue in its control sequence. Next, as represented at line 648 and block 650, the tip of the delivery cannula 22 of the instrument 12 is positioned within the incision made in conjunction with block 642 at a location wherein the forward facing precursor electrodes are at least about 3 mm below the surface of the skin.

Figure 27A:
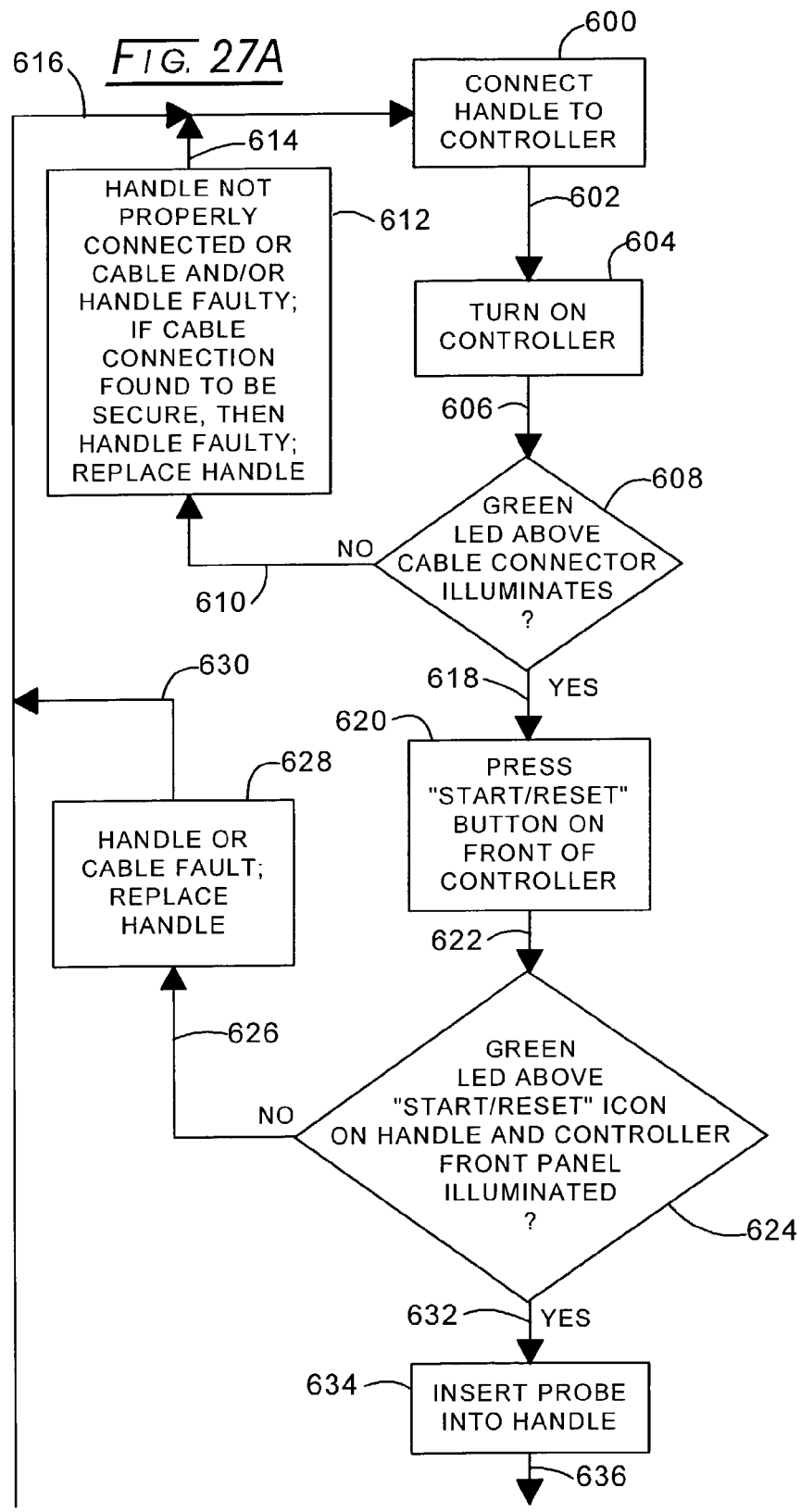
Figure 27C:
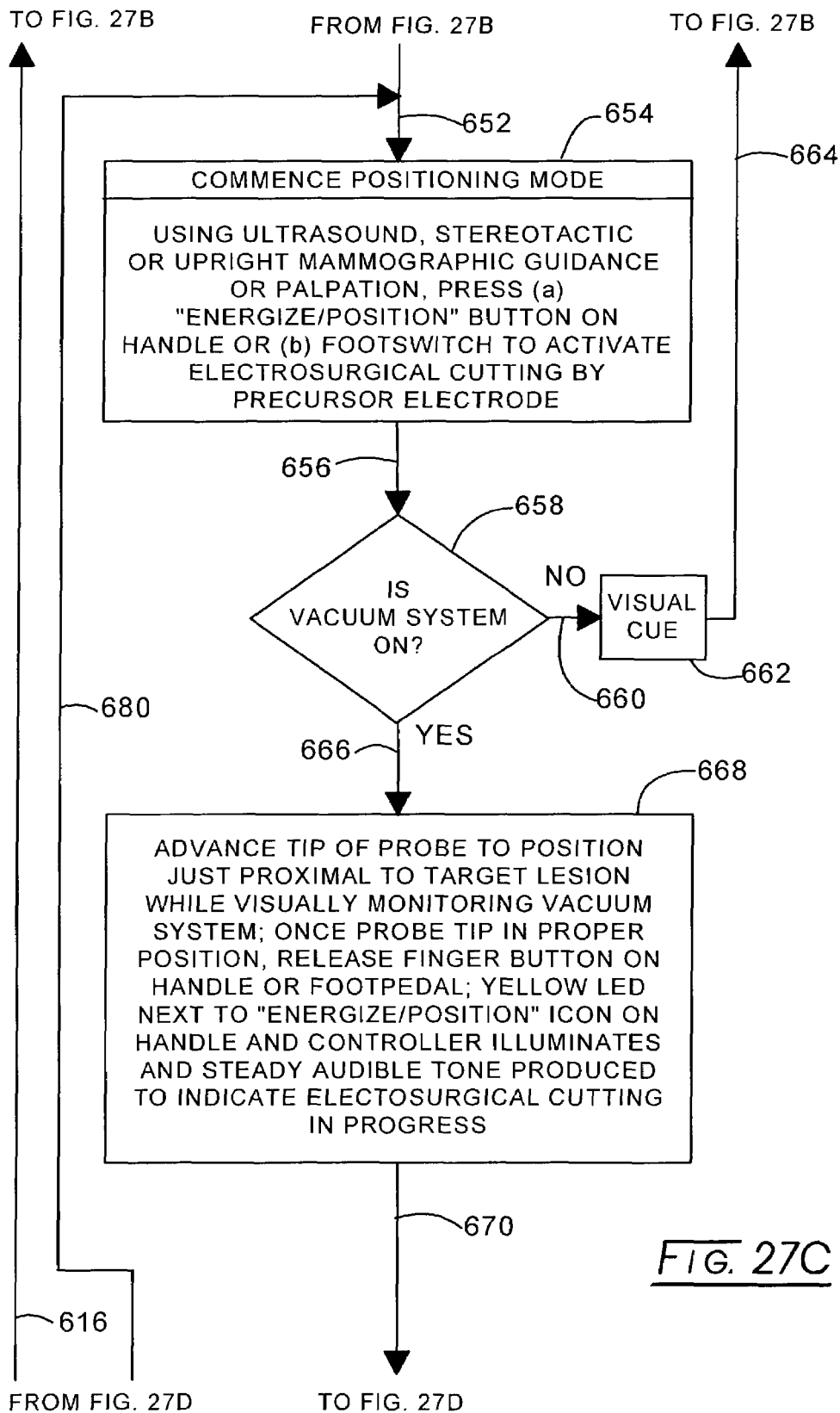

The procedure then commences a positioning mode as represented at line 652 and block 654 (FIG. 27C). During this mode, the practitioner, using ultrasound, sterotactic, upright mammography guidance or palpation, presses the energize/position switch button 57 on component 14 or actuates footswitch 88b to cause the application of electrosurgical current to the precursor electrodes at the tip 32.

As noted above, at this juncture in the procedure, the control assembly may carry out an interlock form of test to assure that the vacuum system turned on earlier is indeed on and working. This test provides an assurance that any accumulated local anesthetic fluids will be evacuated as the system is intermittently paused for evacuation purposes. Accordingly, as represented at line 656 and block 658 a query is made as to whether the vacuum system is on. Where no vacuum is sensed, as represented at line 660 and 662 the system turns on all cueing LEDs and the procedure dwells as represented by line 664 until the vacuum system is activated. Where the vacuum is in proper order and activated, then as represented at line 666 and block 668, the practitioner advances the tip 32 of the probe to a position just proximal of the target lesion. Yellow LED outputs adjacent switch 57 will be illuminated as well as yellow LED 96 at console 64. Additionally, a steady, audible tone is produced while the precursor electrodes are energized.

The procedure then continues as represented at line 670 and block 672 (FIG. 27D). At this juncture of the procedure, the practitioner must be assured that the tip 32 of the delivery cannula 22 is in proper position and in proper orientation for carrying out a specimen capture. Accordingly, as represented at line 674 at block 676, a determination is made as to whether the probe tip 32 is in correct position. If it is not, then as represented at lines 678 and 680, the procedure reverts to line 652 and the positioning mode represented at block 654.

Where the delivery cannula tip 32 is in proper confronting adjacency with the involved tissue volume at this juncture in the procedure, then as represented at line 682 and block 684, an arm capture mode is entered as the practitioner momentarily presses the arm/disarm switch at footswitch 88a or button switch 56 on the reusable component 14. As this occurs, the green LED outputs positioned adjacent switch 56 and at 98 on console 64 are illuminated. Actuation of button switch 56 or footswitch 88a is a prerequisite step before starting tissue capture. Should the practitioner wish to return to the positioning mode of block 654 following the actuation of switch 56, as represented at line 690 and block 692, upon making a determination that tip 32 is not in proper position but the arm capture mode is at hand, then as represented at line 690 and block 692 the practitioner presses the arm/disarm footswitch 88a or handle button 56 again. Then as represented at lines 680 and 652 the positioning mode is reentered and both the footswitch 88b and energize/position switch button 57 again are active.

If the delivery cannula 32 is in a correct position for entering the capture mode from the arm capture mode, then as represented at line 694 and block 696, the capture mode may be entered. Note, for the instant description, the capture mode now is a pulsed or intermittent capture mode wherein the capture component 200 is activated for, for example, two seconds, whereupon a pause mode is entered for the purpose of assuring the evacuation of any pockets or accumulation of fluids, particularly local anesthetic. For example, there will be two four second pauses for a 10 mm capture diameter, the practitioner observing the transparent evacuation tube 236 for the presence of fluids. If the fluid evacuation persists beyond, for example, the four seconds allotted to a pause mode, then the pause mode is continued until the fluid appears to be cleared from tube 36. Initial entry into the capture mode starts a three stage automated sequence. As a stage one, the motor assembly 160 is test energized for about ½ second. The yoke 180 will not have engaged ears 138 and 140 (FIGS. 2, 3) of drive member 276 for this initial ½ second by virtue of the initial spacing between them when the yoke is at its home position. As a stage two, while the motor is deenergized at this juncture, the boost interval occurs with the application of a boost level voltage signal functioning to assure the creation of a cutting arc at the pursing cables of capture component 200. As discussed in connection with FIG. 25, it is desirable that the boost control signal be of minimal duration effective to create an arc. The control system for the instant version of system 10 is one which is driven by a programmable logic device (PLD) which has a controlling clock rate with respect to available time increments for developing the boost control signal. In this regard, the increments are of a 125 millisecond duration. For that minimal duration, the boost voltage will not reach peak 580 as shown in FIG. 25. Accordingly, for the instant demonstration a 250 millisecond signal is employed which will cause the boost voltage to reach its peak 580 and sustain at the ramp level 582 for about 55 milliseconds. This is sufficient to avoid excessive artifact at the captured tissue sample where pulse or intermittent capture technique is employed. Following the boost voltage elevation, as a third stage, the lower normal cut voltage ensues, an arc having been developed at that point in time. At the commencement of the pulse capture mode, as represented at block 696, the start tissue capture button 58 may be pressed or foot pedal 86c may be depressed. This causes a yellow LED adjacent to switch 58 to be illuminated as well as LED 100 on console 64.

Figure 27E:
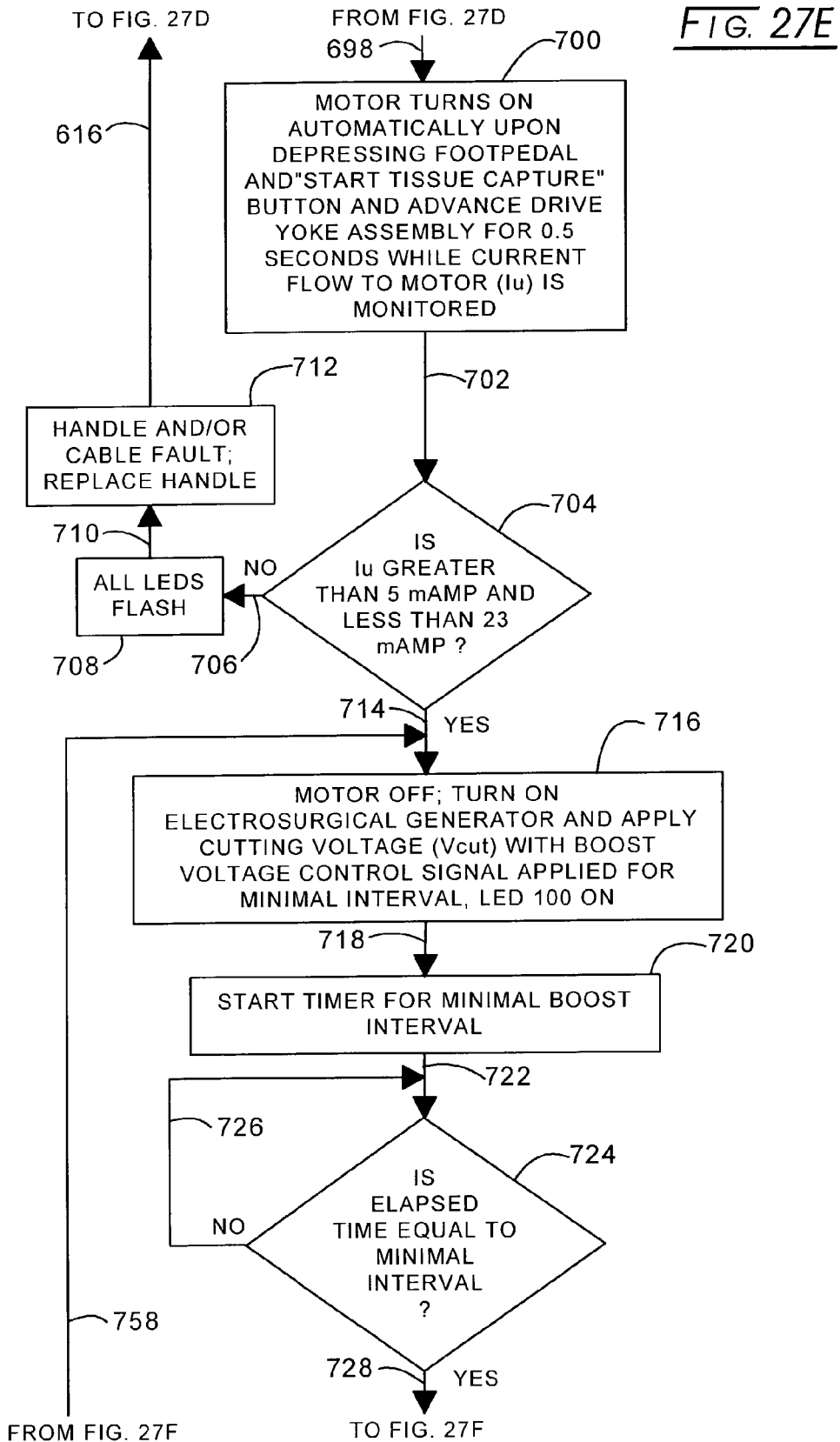

The initial motor performance evaluation as above discussed is summarized in conjunction with lines 698 and block 700 (FIG. 27E). In the latter block, the motor assembly 160 is described as being turned on automatically upon actuation of the start tissue capture switch to provide for a ½ second application of drive current. Then, as represented at line 702 and block 704 a current monitoring test is carried out wherein the motor drive current is called upon to fall within a predetermined window of performance. Where that test fails, then as represented at line 706 and block 708, a visual cue is provided wherein all LEDs are caused to flash and, as represented at line 710 and block 712 the practitioner will have been advised to replace the reusable component 14 referred to as the "handle". The program then reverts as represented at line 616 extending to block 600 (FIG. 27A).

Where the initial motor performance test is passed, then as represented at line 714 and block 716 the initial step in a capture activity is described wherein the motor is off and the boost voltage control signal is applied, for a minimum interval effective to avoid creation of thermal artifacts at the ultimately captured tissue specimen. The sequence of events providing for an initial boost voltage followed by normal cutting voltage levels and deployment of the capture component 200 electrodes will be reiterated.

The number of generations of the capture mode involving excited capture component 200 cables will depend upon the evaluation made by the practitioner, the size of capture involved and the amount of local anesthetic fluid pockets or accumulations which are encountered. LED 100 now is on at console 64 as is the LED above button switch 58 on disposable component 14. As represented at line 718 and block 720, the boost interval control signal is timed for the noted minimal boost interval. In this regard, as represented at line 722 and block 724, a query is posed as to whether the elapsed time for assertion of the boost control signal has reached the minimum interval desired. In the event that it has not, then as represented at loop line 726 the system dwells. In the event that the boost signal has terminated, then as represented at line 728 and block 730 (FIG. 27F), cutting voltage is applied and the motor assembly 160 is turned on to commence deployment of the capture component 200. For the intermittent operation at hand, the procedure continues as represented at line 732 and block 734 determining whether the capture time increment at hand has been completed. In this regard, for example, a capture maximum diametric extent of 10 mm, a capture time increment may be two seconds. In the event that the interval has not been concluded, then the procedure loops as represented at line 736 extending to line 728. Where the capture time increment at hand has been completed, then as represented at line 738 and block 740 the pause mode is entered. A pause mode is derived by releasing either footswitch 88c or corresponding housing button switch 58. As this occurs, LED 104 illuminates and LED 100 turns off. Evacuation system 43 being energized, the practitioner observes transparent tubing 36 during this pause interval to detect the presence of any fluids. The fluid will be clear where local anesthetic solution is being evacuated. Timing of the pause interval will depend upon an evaluation on a preliminary basis on the part of the practitioner. For a 10 mm maximum capture diameter, a pause interval of about four seconds is recommended. Accordingly, as represented at line 742 and block 744, an inquiry is made as to whether the evacuation dwell interval has been completed. In the event that it has not, then the procedure loops as represented at line 746 extending to line 738.

As represented at line 748 and block 750 the practitioner usually monitors the transparent evacuation tube 36 for the presence of fluid. Where that fluid is observed even though the evacuation dwell interval has been completed, the pause interval is maintained as represented at line 752 extending to line 738. Where no fluid is observed following the evacuation dwell interval, as represented at line 754 and block 756 a determination is made as to whether the next capture mode actuation, for example, at footswitch 88c or button switch 58, will be the last iteration. Where the final iteration of capture is not at hand, then as represented at line 758, the program reiterates the capture and pause sequence, line 758 extending to line 714. On the other hand, where an affirmative determination is made with respect to the query at block 756, then as represented at line 760, the capture activity is carried out through capture completion with the full pursing of the cables of capture component 200.

Looking to FIG. 27G as represented at block 762, capture is completed when a forward stall condition is detected at the motor assembly 160. Upon such detection of this forward stall condition, the capture complete mode is entered, the capture of target tissue being completed and, accordingly, electrosurgical cutting voltage is terminated.

Motor assembly 160 then automatically reverses to return to the yoke 180 (FIG. 3) to its home position. Additionally, a green LED positioned forwardly of switch 58 on component 14 is illuminated as well as green LED 102 on console 64. Next, as represented at line 764 and block 766 a query is posed as to whether a reverse stall current threshold limit has been reached. Accordingly, as the motor is energized in reverse, the system awaits that stall condition as represented at loop line 768. Upon an affirmative determination that the reverse stall condition is at hand, as represented at line 770 and block 772, the practitioner removes the delivery cannula 22 from the patient by appropriate manipulation of instrument 12. During this removal, some stretching of the tissue typically will be encountered with little or no disfigurement ensuing.

Next, as represented at line 774 and block 776 the vacuum system or assembly is disconnected and the locking nut 26 is unscrewed. Then, as represented at line 778 and block 780 the practitioner retracts ears 138 and 140 (FIG. 2) to a convenient position to establish a specimen access orientation with the leafs of the capture component. That containment orientation resembles a cup or basket. Then as represented at line 782 and block 784, the tissue specimen is placed in a container with appropriate solution for transport and storage in preparation for examination by a pathologist. As represented at line 786 and block 788, the specimen is transported to a pathology laboratory.

An optional arrangement is represented at line 790 and block 792. The latter block provides for placing a radioopaque and/or echogenic marker in the tissue at the site of the biopsy and verifying the position thereof using radiography or ultrasonography. Then, as represented at line 794 and block 796, the skin incision is closed using appropriate conventional closure technique. The specimen also may be simply removed from the basked-like encagement of capture component 200 by the simple expedience of severing the cables with scissors or the like.

Since certain changes may be made in the above method without departing from the scope of the invention herein involved, it is intended that all matter contained in the above description or shown in the accompanying drawings shall be interpreted as illustrative and not in limiting sense.

APPENDIX A

Anesthesia Effect on Resistance vs Time

May 10, 2002

Location: The Ohio State University Medical Center

Acute Animal Study

Experiment 1

For the resistance measurements carried out in connection with experiments 1–7 a resistance measuring needle was, prepared. The needle was formed of type 304 stainless steel, 24 gauge and 1½ inches in length. An electrically insulative cannula was positioned over the shank of the needle to the vicinity of the commencement of the point. The cannula was formed of 0.6 mil shrink tubing and the arrangement provided for a 3–4 millimeter exposed steel tip for resistance evaluation. The needle was coupled with a syringe for the injection of local anesthesia, and the animal employed was a fully anesthetized 366 pound female pig positioned on its back. This testing needle was electrically coupled with a Fluke-type PM6306RLC meter, the adjustable frequency of which was established at 34.0 kHz. The meter was additionally attached to a return provided as a Erbe Nessy Plate-type 170 having an area of 168 square centimeters. This dispersive return was positioned upon the chest of the pig. Test locations were marked at the nipple region of the supinate pig and the depth of local anesthetic injection, $D_{ai}$ was established as being within a range from about 1.5 cm to 2.0 cm. For each test or experiment, an initial resistance reading was made prior to injection of the elected local anesthetic and the value of pre-infection resistance was recorded adjacent a tabular zero value for the time from injection of anesthetic in seconds or minutes. During the first 15 seconds subsequent to the injection of a bolus of local anesthetic, the meter was watched and minimum resistance in ohms was recorded.

| | |
|---|---|
| M.W.J. | 5:40 pm |
| Local anesthesia: | (1%) in normal saline |
| Volume: | 3 cc |
| Minimum resistance | 219 ohms |

TABLE 1

| Time from injection of anesthetic in seconds | Resistance in ohms |
|---|---|
| 0 | 690 |
| 15 | 277 |
| 30 | 346 |
| 45 | 259 |
| 60 (1 min) | 260 |
| 90 | 273 |
| 120 (2 min) | 293 |
| 180 (3 min) | 283 |
| 240 (4 min) | 291 |
| 300 (5 min) | 286 |
| 360 (6 min) | 284 |
| 420 (7 min) | 282 |
| 480 (8 min) | 283 |
| 540 (9 min) | 285 |
| 600 (10 min) | 293 |
| 11 min | 299 |
| 12 min | 290 |
| 13 min | 288 |
| 14 min | 439 |
| 38 min | 278 |

Experiment 2

| M.W.J. | 5:55 pm |
|---|---|
| Local anesthesia: | (1%) with Epinephrine 1:200,000 in normal saline |
| Volume: | 3.5 cc |
| Minimum resistance: | 149 ohms |

TABLE 2

| Time from injection of anesthetic in seconds | Resistance in ohms |
|---|---|
| 0 | 304 |
| 15 | 172 |
| 30 | 177 |
| 45 | 181 |
| 60 (1 min) | 184 |
| 90 | 188 |
| 120 (2 min) | 190 |
| 180 (3 min) | 197 |
| 240 (4 min) | 202 |
| 300 (5 min) | 207 |
| 360 (6 min) | 212 |
| 420 (7 min) | 216 |
| 480 (8 min) | 219 |
| 540 (9 min) | 221 |
| 600 (10 min) | 224 |
| 11 min | 225 |
| 12 min | 226 |

Experiment 3

In addition to carrying out resistance measurements with the anesthetic injecting needle referred to as "over bolus" a second resistance measuring needle was injected at a position 2 cm spaced from the bolus injecting needle.

Readings at the second needle as tabulated below were made following about a five second delay from the readings made with the first fluid injecting needle to permit appropriate electrical connection with the Fluke meter.

| M.W.J. | 6:23 pm |
|---|---|
| Local anesthesia: | (1%) with Epinephrine 1:200,000 in normal saline |
| Volume: | 3 cc |
| Minimum resistance | (over bolus) 135 ohms |

TABLE 3

| Time from injection of anesthetic in seconds | Resistance over bolus in ohms | Resistance at 2 cm in ohms |
|---|---|---|
| 0 | 332 | 304 |
| 15 | 146 | 288 |
| 30 | 149 | 287 |
| 60 (1 min) | 152 | 287 |
| 90 | 153 | 286 |
| 120 (2 min) | 154 | 284 |
| 180 (3 min) | 155 | 283 |
| 240 (4 min) | 157 | 281 |
| 300 (5 min) | 157 | 279 |
| 360 (6 min) | 159 | 279 |
| 420 (7 min) | 160 | 278 |
| 480 (8 min) | 160 | 278 |
| 540 (9 min) | 161.6 | 276.6 |
| 600 (10 min) | 160.8 | 279.8 |

TABLE 3-continued

| Time from injection of anesthetic in seconds | Resistance over bolus in ohms | Resistance at 2 cm in ohms |
|---|---|---|
| 12 min | 162 | 276 |
| 30 min | 168 | 265 |

Experiment 4

In this experiment, two additional resistance measuring needles were employed, the first of these additional needles was spaced 1 cm from the over bolus syringe and the second needle was spaced 2 cm from it. The locations of these three needles were respectively marked with green, yellow and white markers. Minimum resistance was observed at the over bolus needle.

| M.W.J. | 7:07 pm |
|---|---|
| Local anesthesia: | (1%) with Epinephrine 1:200,000 in normal saline |
| Volume: | 3 cc |
| Minimum resistance | 109 ohms |

TABLE 4

| Time from injection of anesthetic in seconds | Over bolus Resistance in ohms (green) | Resistance at 1 cm in ohms (yellow) | Resistance at 2 cm in ohms (white) |
|---|---|---|---|
| 0 | 380 | 407 | 255 |
| 15 | 194 | 188 | 250 |
| 30 | 203 | 192 | 252 |
| 60 (1 min) | 206 | 189 | 252 |
| 90 | 204 | 184 | 251 |
| 120 (2 min) | 206 | 192 | 253 |
| 180 (3 min) | 210 | 192 | 251 |
| 240 (4 min) | 212 | 192 | 250 |
| 300 (5 min) | 212 | 191 | 250 |
| 360 (6 min) | 210 | 192 | 251 |

Experiment 5

In addition to an over bolus measurement of resistance, two additional resistance measurements were made with two additional needles orthogonally arranged with respect to the over bolus needle and spaced from it 2 cm. The green, white and yellow coding as described in connection with Experiment 4 were employed. Minimum resistance was measured with respect to the over bolus needle.

| M.W.J. | 8:13 pm |
|---|---|
| Local anesthesia: | (1%) with Epinephrine 1:200,000 in normal saline |
| Volume: | 5 cc |
| Minimum resistance | over bolus 205 ohms |

TABLE 5

| Time from injection of anesthetic in seconds | Over Bolus Green | Yellow 2 cm | White 2 cm |
|---|---|---|---|
| 0 | 539 | 582 | 446 |
| 15 | 217 | 587 | 427 |

TABLE 5-continued

| Time from injection of anesthetic in seconds | Over Bolus Green | Yellow 2 cm | White 2 cm |
|---|---|---|---|
| 30 | 216 | 590 | 426 |
| 60 (1 min) | 215 | 588 | 423 |
| 90 | 215 | 589 | 421 |
| 120 (2 min) | 216 | 590 | 421 |
| 180 (3 min) | 221 | 594 | 418 |
| 240 (4 min) | 224 | 595 | 417 |
| 300 (5 min) | 227 | 594 | 421 |
| 360 (6 min) | 231 | 592 | 420 |

Experiment 6

For experiments 6 and 7 no local anesthesia was utilized and a 5% dextrose solution identified as "D5-W" was employed as the injected bolus. For the instant experiment, a maximum resistance reading of 670 ohms was observed during the injection of the D5-W.

| M.W.J. | |
|---|---|
| Injectate: | 10:55 pm D5-W |
| Volume: | 5 cc |

TABLE 6

| Time from injection of injectate in seconds | Resistance in ohms |
|---|---|
| 0 | 404 |
| 15 | 630 |
| 60 (1 min) | 574 |
| 120 (2 min) | 549 |

Experiment 7

| M.W.J. | |
|---|---|
| Injectate: | D5-W |
| Volume: | 5 cc |

TABLE 7

| Time from injection of injectate in seconds | Resistance in ohms |
|---|---|
| 0 | 211 |
| 15 | 347 |
| 30 | 289 |
| 45 | 276 |
| 60 (1 min) | 303 |
| 90 | 281 |
| 120 (2 min) | 317 to 279 |

APPENDIX B

Anesthesia Effect on Resistance vs Time and Corresponding Tissue Capture Data

May 10, 2002

Location: The Ohio State University Medical Center

Acute Animal Study

For experiments 1–14 as set forth in this Exhibit B the same animal as described in Appendix A was employed at the same location. The experiments in general were carried out in two steps. The initial step was to measure resistance in the manner described in connection with Appendix A. This initial step was followed by the carrying out of a tissue capture procedure utilizing a capture instrument and associated disposable probe as well as a controller/electrosurgical generator, all marketed under the trade designation "Model 3000", by Neothermia Corporation of Natick, Mass. For all tests, the controller/electrosurgical generator had either a serial No. 90392 or where indicated, serial No 89139 and a power profile corresponding with curve 456 of FIG. 16. The capture component of the disposable probe is referred to as the "basket". The term "plastic damage" refers to thermal damage to polymeric tip components 192 and 194 described in FIG. 7. In general such thermal damage is a consequence of the arc-based cutting action being intensified by initial contact with saline fluid influenced tissue. The term "Parylene" refers to a conformal electrically insulative coating described in conjunction with FIG. 6. The dimension $L_B$ refers to basket length of the capture component in millimeters. The dimension $D_B$ refers to the diametric-like dimensions in millimeters of the capture component or basket. The dimension $L_S$ refers to the length of the capture tissue specimen in millimeters. The dimension $D_s$ refers to the diametric-like dimensions of the capture tissue specimen in millimeters. The term "cables" refers to the cutting cables 230 through 234 described, for instance in FIG. 5. The term "leafs" refer to the leaf components as described at 210 through 214 in FIG. 9. The term "eyelets" refers to the leaf tip eyelet components described, for instance, connection with FIG. B. The initials "P.E" refer to the precursor electrodes identified, for instance, at 184 through 187 in FIG. 8. The terms "start capture" refer to the dwell interval extending from the time of injection of injectate to the commencement of the start of a capture procedure with the deployment of capture leafs and cables.

Experiment 1

| M.W.J. | |
|---|---|
| Local anesthesia: | (1%) with Epinephrine 1:200,000 in normal saline |
| Volume: | 3 cc |
| Minimum resistance | 146 ohms |

TABLE 1

| Time from injection of anesthetic in seconds | Resistance in ohms |
|---|---|
| 0 | 221 |
| 15 | 153 |
| 30 | 154 |
| 60 (1 min) | 155 |
| 90 | 156 |
| 120 (2 min) | 157 |
| 180 (3 min) | 159 |
| 240 (4 min) | 160 |
| 300 (5 min) | 154 |

Start capture: 7 minutes

Probe: M5-10-04

Cable status: All intact

Sample weight: 0.804 gram

Comment: Good capture

Experiment 2

| M. W. J. | 8:28 pm |
|---|---|
| Local anesthesia: | (1%) with Epinephrine 1:200,000 in normal saline |
| Volume: | 8 cc |
| Minimum resistance | 101 ohms |

TABLE 2

| Time from injection of anesthetic in seconds | Resistance in ohms |
|---|---|
| 0 | 128 |
| 15 | 107 |
| 30 | 108 |

Start P.E. advancement: 1 minute
Start capture: 2 minutes
Probe: M5-10-03
Cable status: Some fraying in 4 cables
Parylene: Light damage (I leaf medium), underside of leafs good
Plastic damage: Light amount
$L_B$=18 mm, $D_B$=9.0 mm×9.0 mm
$L_S$=15 mm, $D_S$=10.5 mm×8.0 mm
Sample weight: 0.589 gram
Basket filling: 95%
Sample condition: contiguous
Comment: Capture in center of bolus. Eyelets bent over in normal fashion.

Experiment 3

| M. W. J. | 8:45 pm |
|---|---|
| Local anesthesia: | (1%) with Epinephrine 1:200,000 in normal saline |
| Volume: | 3 cc |
| Minimum resistance | 103 ohms |

TABLE 3

| Time from injection of anesthetic in seconds | Resistance in ohms |
|---|---|
| 0 | 189 |
| 15 | 108 |
| 30 | 110 |

Start capture: 2 minutes
Probe: M5-10-05
Cable status: Ok, no frays or breaks
Plastic damage: None
$L_B$=14 mm, $D_S$=11 mm×10 mm
Sample weight: 0.599 gram
Basket filling: 80%
Comments: Very fibrous tissue. Small amount of smoke and bleeding.

Experiment 4

| M. W. J. | 9:07 pm |
|---|---|
| Local anesthesia: | (1%) with Epinephrine 1:200,000 in normal saline |
| Volume: | 12 cc |
| Start capture: | 1 minute |
| Probe: | M5-10-2 |
| Cable status: | Two cables broken |
| Plastic damage: | Much more damage |
| Sample weight: | 0.534 gram |

Experiment 5

| M. W. J. | 9:15 pm |
|---|---|
| Local anesthesia: | (1%) with Epinephrine 1:200,000 in normal saline |
| Volume: | 10 cc |
| Start P.E. advancement: | Energize but do not advance |
| Start capture: | 1 minute |
| Cable status: | Ok - minimal damage |
| Plastic damage: | none |
| $L_S$ = 17 mm, | |
| $D_S$ = 11.5 mm × 10.0 mm | |
| Basket filling: | 95% |
| Sample condition: | Single piece. Fold on one side |
| Sample weight: | 0.814 gram |
| Comments: | Fibrous tissue under nipple. Some blackening near tip of eyelets. |

Experiment 6

| M. W. J. | 9:30 pm |
|---|---|
| Local anesthesia: | (1%) with Epinephrine 1:200,000 in normal saline |
| Volume: | 5 cc at each of six radial sites spaced 1 cm from capture line for a total of 30 cc |
| Start capture: | 1 minute |
| Probe: | M5-10-6 |
| Cable status: | Wires intact |
| Plastic damage: | None |
| Comments: | Eyelets ok, one leaf slightly deformed. |

Experiment 7

| M. W. J. | |
|---|---|
| Local anesthesia: | (1%) with Epinephrine 1:200,000 in normal saline |
| Volume: | 10 cc |
| Start capture: | 1 minute |
| Probe: | M5-10-7 |
| Cable status: | Ok |
| Plastic damage: | None |
| Parylene: | Ok |
| Sample weight: | 0.644 gram |
| Comments: | Eyelets bent over. Smoke observed. Region of capture was compressed in a yellow vice. |

Experiment 8

| M. W. J. | |
|---|---|
| Local anesthesia: | (1%) with Epinephrine 1:200,000 in normal saline |
| Volume: | 12 cc |
| Start capture: | less than 1 minute |
| Probe: | M5-10-8 |
| Comments: | injected into basket region. No capture. Eyelets bent inward. |

Experiment 9

| M. W. J. | |
|---|---|
| Local anesthesia: | (1%) with Epinephrine 1:200,000 in normal saline |
| Probe: | M5-10-9 |
| Parylene: | Blackened at tip of leafs |
| Comments: | No capture. Eyelets bent outward. Evidence of electrosurgical action on necks, tails and eyelets of leafs. |

Experiment 10

| M. W. J. | |
|---|---|
| Local anesthesia: | (1%) with Epinephrine 1:200,000 in normal saline |
| Volume: | 10 cc injected 2 full seconds after start of capture |
| Probe: | M5-10-10 |
| Cable status: | Evidence of electrosurgery cutting on wires |
| Comments: | No capture. All eyelets folded back. |

Experiment 11

| M. W. J. | |
|---|---|
| Local anesthesia: | (1%) with Epinephrine 1:200,000 in normal saline |
| Probe: | M5-10-11 |
| P.E. resistance: | 348 ohms |
| P.E. resistance after injection: | 238 ohms |
| Cable resistance: | 188 ohms |
| Cable status: | No wires broken |
| Comments: | Good capture. Moderate damage to probe. |

Experiment 12

| M. W. J. | 10:02 pm |
|---|---|
| Local anesthesia: | (1%) with Epinephrine 1:200,000 in normal saline |
| Volume: | 10 cc |
| Probe: | M5-10-12 |
| Start P.E. advancement: | 7 minutes |
| Cable status: | 4 of 5 damaged |
| Comments: | Retry with second probe. Electrosurgical action on P.E. Little or no electrosurgical action. |

Experiment 13

| M. W. J. | 10:30 pm |
|---|---|
| Local anesthesia: | (1%) with Epinephrine 1:200,000 in normal saline |
| Volume: | 8 cc injected 10 ohms in front of probe |
| Controller/Electrosurgical Generator: | SN 89139 |
| Start capture: | 30 seconds |
| P.E. resistance: | 376 ohms prior to injection of anesthetic agent |
| P.E. resistance after injection: | 220 ohms |
| Cable resistance: | 278 ohms |
| Cable status: | 3 broken wires |
| Comments: | Initial breast region incision made. No capture. |

Experiment 14

| M. W. J. | 11:00 pm |
|---|---|
| Local anesthesia: | (1%) with Epinephrine 1:200,000 in normal saline |
| Volume: | 3 cc at six radial locations spaced 2 cm from capture line |
| Controller/Electrosurgical Generator: | SN 89139 |
| Start capture: | 5 minutes |
| Sample size 10 mm × 9.5 mm | |
| Sample weight: | 0.693 gram |
| Plastic damage: | Little |
| Parylene: | Damage on inside and outside of one leaf |
| Comments: | Good sample. One leaf eyelet bent back. |

What is claimed is:

1. The method for accessing subcutaneous target tissue of an animal comprising the steps of:
   providing an electrosurgical system including an electrosurgical generator and an operatively associated cutting electrode assembly energizable to provide a tissue cutting arc;
   anesthetizing said animal by parenterally administering at the site of said tissue a solution of a local anesthetic agent and biocompatible diluent exhibiting an electrical conductivity of value effective for providing an electrical resistance at tissue confronting said electrode sustaining said tissue cutting arc when said solution is infiltrated within the tissue of said animal;
   positioning said electrode subcutaneously at said site;
   energizing said cutting electrode to provide said tissue cutting arc; and
   maneuvering said electrode with respect to said target tissue.

2. The method of claim 1 in which said step of anesthetizing said animal is carried out with a said solution exhibiting an electrical conductivity of less than about 10 milliSiemens/cm.

3. The method of claim 2 in which said step of anesthetizing said animal is carried out with a said solution exhibiting an osmolarity between about 240 and about 340 milliOsmols/liter.

4. The method of claim 1 in which said step of anesthetizing said animal is carried out with a said solution exhibiting an electrical conductivity of less than about 5 milliSiemens/cm.

5. The method of claim 1 in which said step of anesthetizing said animal is carried out with a said solution comprising D-glucose monohydrate in water as a said diluent.

6. The method of claim 1 further comprising the steps of:
   providing an evacuation system having an intake port located in adjacency with said electrode; and
   applying a vacuum at said intake port effective to evacuate accumulations of said solution encountered by said electrode assembly during said maneuvering step.

7. The method of claim 6 in which:
   said step of maneuvering said electrode is carried out by moving said electrode assembly about said target tissue in an intermittent manner wherein said electrode assembly is energized while being advanced for a cutting interval, then de-energized and maintained stationary for a pause interval while said vacuum is applied.

8. The method of claim 7 in which:
said electrode assembly is advanced for a said cutting interval of from about one second to about two seconds.

9. The method of claim 7 in which:
said electrode assembly is de-energized during said pause interval.

10. The method of claim 7 in which:
said electrode is maintained stationary for a pause interval of from about four seconds to about six seconds.

11. The method of claim 10 in which:
said electrode assembly is de-energized during said pause interval.

12. The method of claim 7 in which:
said step for providing an evacuation system provides said system as comprising a vacuum pump having a vacuum port and a transparent tube coupled in vacuum communication between said vacuum port and said intake port; and
said pause interval is maintained while said solution is visibly perceptible in said transparent tube.

13. The method for surgically accessing a target tissue volume of a patient comprising the steps of:
(a) providing an accessing instrument having an electrosurgical cutting assembly at its distal end which is energizable to form an electrosurgical cutting arc;
(b) providing a fluid evacuation assembly having a fluid intake port adjacent said electrosurgical cutting assembly and actuable to effect a fluid suction condition at said fluid intake port;
(c) anesthetizing said patient by parenterally administering a solution of a local anesthetic agent and biocompatible diluent about the site of said target tissue volume;
(d) forming an opening of limited depth in the skin of said patient using a cutting instrument;
(e) positioning said distal end of said instrument within said opening;
(f) energizing said electrosurgical cutting assembly to effect creation of said cutting arc;
(g) actuating said fluid evacuation assembly; and
(h) maneuvering said accessing instrument with respect to said target tissue volume with a motion effective to cause the aspiration through said intake port of accumulations of said solution within the tissue of said patient to an extent wherein said cutting arc is maintained effective to cut tissue.

14. The method of claim 13 in which:
said step (h) of maneuvering said electrode is carried out by moving said electrosurgical cutting assembly about said target tissue volume in an intermittent manner wherein said electrosurgical cutting assembly is energized while being advanced for a cutting interval, then is maintained stationary for a pause interval of duration to effect said aspiration of said solution.

15. The method of claim 14 in which:
said electrosurgical cutting assembly is de-energized during said pause interval.

16. The method of claim 14 in which:
said electrosurgical cutting assembly is maintained stationary for a pause interval of from about four seconds to about six seconds.

17. The method of claim 14 in which:
said step (b) for providing said fluid evacuation assembly provides said assembly as comprising a vacuum pump having a vacuum port and a transparent tube coupled in vacuum communication between said vacuum port and said intake port; and
said pause interval is maintained while said solution is visibly perceptible in said transparent tube.

18. The method for surgically accessing a target tissue volume of a patient comprising the steps of:
(a) providing an accessing instrument having an electrosurgical assembly at a distal end thereof which is energizable from an electrosurgical cutting output to form an electrosurgical cutting arc;
(b) providing an electrosurgical generator assembly controllable to provide a said electrosurgical output at a boost cutting voltage level effective to create said cutting arc, and to provide a said electrosurgical output at an arc supporting cutting voltage level less than said boost cutting voltage level;
(c) forming an opening of limited depth in the skin of said patient;
(d) positioning said distal end of said instrument within said opening;
(e) controlling said electrosurgical generator assembly to provide a said electrosurgical output at said boost cutting voltage level for a boost interval effective to create said cutting arc;
(f) then controlling said electrosurgical generator assembly to provide a said electrosurgical output at said arc supporting cutting voltage level; and
(g) maneuvering said accessing instrument to access said target tissue volume.

19. The method of claim 18 in which:
said step (e) controls said electrosurgical generator to provide a said boost cutting voltage level which is greater than said arc supporting voltage level by a factor within a range of about 1.2 to 1.5.

20. The method of claim 18 in which:
said step (e) controls said electrosurgical generator assembly to provide said electrosurgical output at said boost cutting voltage level for a boost interval of about 55 milliseconds.

21. The method of claim 18 in which:
said step (g) of maneuvering said accessing instrument is carried out in an intermittent manner wherein said electrosurgical assembly is energized while being maneuvered for a cutting interval, then is maintained substantially stationary for a pause interval during which said electrosurgical assembly is de-energized.

22. The method of claim 21 in which:
said step (a) further comprises the step: (a1) providing a fluid evacuation assembly having a fluid intake port adjacent said electrosurgical assembly and providing a fluid removal condition at said fluid intake port; and
said step (g) maintains said pause interval for a duration effective to remove cutting arc defeatable fluid from the vicinity of said electrosurgical assembly.

23. The method for accessing and isolating a target tissue volume of given peripheral extent within adjacent tissue of a patient, comprising the steps of:
(a) providing an electrosurgical generator controllable to derive an electrosurgical output;
(b) providing a tissue accessing and isolating assembly having a forwardly disposed portion with an accessing electrosurgical electrode and a deployable tissue isolating electrosurgical electrode assembly;
(c) providing a local anesthetic as a solution of local anesthetic agent and a biocompatible diluent;
(d) anesthetizing said patient by parenterally administering said local anesthetic to effect infiltration of said solution within said adjacent tissue;

(e) applying said electrosurgical output from said electrosurgical generator to said accessing electrosurgical electrode to an extent effective to derive an electrosurgical cutting arc while maneuvering said tissue accessing and isolating assembly forwardly disposed portion within said adjacent tissue into a location adjacent to said target tissue volume;

(f) terminating said step (e) application of said electrosurgical output to said accessing electrosurgical electrode when said tissue accessing and isolating forwardly disposed portion is within said adjacent tissue at said location adjacent to said target tissue volume;

(g) applying said electrosurgical output from said electrosurgical generator to said tissue isolating electrode at a voltage level effective to derive an electrosurgical cutting arc while substantially avoiding formation of caloric artifact at said target tissue volume; and (h) maneuvering said tissue isolating electrode circumscriptively within said adjacent tissue about said target tissue volume during said step (g) to effect the isolation thereof from said adjacent tissue.

24. The method of claim 23 in which said step (e) further comprises the step:

(e1) effecting removal of fluid within said patient located adjacent said accessing electrosurgical electrode in conjunction with said step (e) maneuvering of said forwardly disposed portion to an extent effective to maintain said derivation of said electrosurgical cutting arc.

25. The method of claim 23 in which:

said step (e), wherein said tissue accessing and isolating assembly forwardly disposed portion is maneuvered within said adjacent tissue, is carried out in an intermittent manner wherein said electrosurgical output is applied for a cutting interval, then said forwardly disposed portion is maintained substantially stationary for a pause interval during which said application of said electrosurgical output is terminated.

26. The method of claim 24 in which:

said step (e), wherein said tissue accessing and isolating assembly forwardly disposed portion is maneuvered within said adjacent tissue, is carried out in an intermittent manner wherein said electrosurgical output is applied for a cutting interval, then said forwardly disposed portion is maintained substantially stationary for a pause interval during which said application of said electrosurgical output is terminated.

27. The method of claim 26 in which:

said step (e) maintains said pause interval for a duration effective to remove cutting arc defeatable fluids from the vicinity of said accessing electrosurgical electrode.

28. The method of claim 18 in which:

said step (a) further comprises the step: (a1) providing a fluid evacuation assembly having a fluid intake port adjacent said electrosurgical assembly and providing a fluid removal condition at said fluid intake port; and said fluid removal condition is rovided simultaneously with said steps (e), (f), and (g).

29. The method for carrying out a surgical procedure upon a patient comprising the steps of:

(a) providing an accessing instrument having an electrosurgical cutting assembly which is energizable to form an electrosurgical cutting arc;

(b) anesthetizing said patient by parenterally administering a solution of a local anesthetic agent and biocompatible diluent into tissue of said patient;

(c) energizing said electrosurgical cutting assembly to effect creation of said cutting arc;

(d) maneuvering said accessing instrument borne electrosurgical cutting assembly to carry out a surgical procedure within the tissue of said patient; and (e) simultaneously with said step (d) evacuating fluid within the path of said maneuvering.

30. The method for surgically accessing a target tissue volume of a patient comprising the steps of:

(a) providing an accessing instrument having an electrosurgical cutting assembly at its distal end which is energizable to form an electrosurgical cutting arc;

(b) providing a fluid evacuation assembly having a fluid intake port adjacent said electrosurgical cutting assembly and actuable to effect a fluid suction condition at said fluid intake port;

(c) anesthetizing said patient by parenterally administering a solution of a local anesthetic agent and biocompatible diluent about the site of said target tissue volume;

(d) forming an opening of limited depth in the skin of said patient using a cutting instrument;

(e) positioning said distal end of said instrument within said opening;

(f) energizing said electrosurgical cutting assembly to effect creation of said cutting arc;

(g) actuating said fluid evacuation assembly; and (h) maneuvering said accessing instrument with respect to said target tissue volume while activating said fluid evacuation assembly to effect said fluid suction condition at said fluid intake port.

31. The method for accessing and isolating a target tissue volume of given peripheral extent within adjacent tissue of a patient, comprising the steps of:

(a) providing an electrosurgical generator controllable to derive an electrosurgical output;

(b) providing a tissue accessing and isolating assembly having a forwardly disposed portion with an accessing electrosurgical electrode and a deployable tissue isolating electrosurgical electrode assembly;

(c) providing a fluid evacuation assembly having a fluid intake port at said tissue accessing and isolating assembly forwardly disposed portion and actuable to effect a fluid suction condition at said fluid intake port;

(d) providing a local anesthetic as a solution of local anesthetic agent and a biocompatible diluent;

(e) anesthetizing said patient by parenterally administering said local anesthetic to effect infiltration of said solution within said adjacent tissue;

(f) applying said electrosurgical output from said electrosurgical generator to said accessing electrosurgical electrode to an extent effective to derive an electrosurgical cutting arc while maneuvering said tissue accessing and isolating assembly forwardly disposed portion within said adjacent tissue into a location adjacent to said target tissue volume (g) terminating said step (f) application of said electrosurgical output to said accessing electrosurgical electrode when said tissue accessing and isolating forwardly disposed portion is within said adjacent tissue at said location adjacent to said target tissue volume (h) applying said electrosurgical output from said electrosurgical generator to said tissue isolating electrode at a voltage level effective to derive an electrosurgical cutting arc while substantially avoiding formation of caloric artifact at said target tissue volume;

(i) maneuvering said tissue isolating electrode circumscriptively within said adjacent tissue about said target tissue volume during said step (g) to effect the isolation thereof from said adjacent tissue; and (k) actuating said fluid evacuation assembly to effect said fluid suction condition during said steps (f), (h) and (i).

* * * * *